(12) United States Patent
Mizutani et al.

(10) Patent No.: US 7,960,394 B2
(45) Date of Patent: Jun. 14, 2011

(54) QUINAZOLINE DERIVATIVE

(75) Inventors: Takashi Mizutani, Moriya (JP);
Tsuyoshi Nagase, Tsukuba (JP);
Nagaaki Sato, Tsukuba (JP); Akio Kanatani, Ushiku (JP); Shigeru Tokita, Tsukuba (JP)

(73) Assignee: Banyu Pharmaceutical Co., Ltd., Tokyo (JP)

( * ) Notice: Subject to any disclaimer, the term of this patent is extended or adjusted under 35 U.S.C. 154(b) by 1231 days.

(21) Appl. No.: 11/628,087

(22) PCT Filed: May 30, 2005

(86) PCT No.: PCT/JP2005/010291
§ 371 (c)(1),
(2), (4) Date: Nov. 27, 2006

(87) PCT Pub. No.: WO2005/115993
PCT Pub. Date: Dec. 8, 2005

(65) Prior Publication Data
US 2008/0275069 A1    Nov. 6, 2008

(30) Foreign Application Priority Data

May 31, 2004    (JP) ................ 2004-162459

(51) Int. Cl.
*A01N 43/00* (2006.01)
*C07D 239/70* (2006.01)

(52) U.S. Cl. ........... 514/258.1; 514/262.1; 514/265.1; 544/253; 544/254; 544/256; 544/257; 544/262; 544/264

(58) Field of Classification Search .......... 544/253, 544/254, 256, 257, 262, 264, 258.1, 262.1, 544/265.1
See application file for complete search history.

(56) References Cited

U.S. PATENT DOCUMENTS

| | | | |
|---|---|---|---|
| 4,154,837 A | 5/1979 | Heider et al. | |
| 4,379,788 A | 4/1983 | Heider et al. | |
| 6,072,057 A | 6/2000 | Phillips et al. | |
| 7,521,455 B2 | 4/2009 | Nagase et al. | |
| 2008/0139589 A1 | 6/2008 | Kanatani et al. | |
| 2009/0209562 A1 | 8/2009 | Nagase et al. | |

FOREIGN PATENT DOCUMENTS

| | | |
|---|---|---|
| DE | 3220898 | 3/1982 |
| JP | 2004-131497 | 4/2004 |
| WO | WO 03/042359 | 11/2002 |

*Primary Examiner* — Paul V. Ward
(74) *Attorney, Agent, or Firm* — J. Eric Thies; Gerard M. Devlin

(57) ABSTRACT

This invention provides a compound or its pharmaceutically-acceptable salt of formula (I)

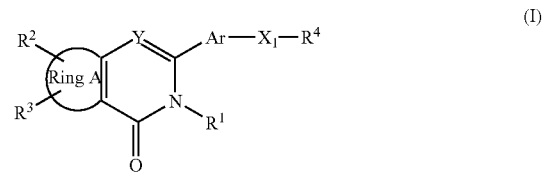

wherein $R^1$ represents a lower alkyl group et al; $R^2$ and $R^3$ are same and different and represents hydrogen atm et al; $R^4$ represents the substituent of the formula (II) et al;

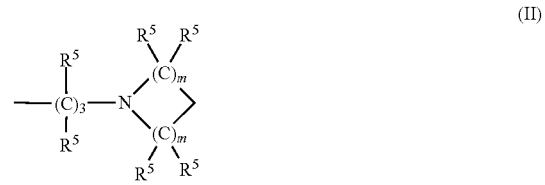

$X_1$ represents NH, O or S; Y represents N or C; Ar is a divalent substituent derived from aryl et al, by removing two hydrogen atoms therefrom; the ring A represents a 5- or 6-membered heteroaryl group; this compounds has a histamine-H3 receptor antagonistic effect or a histamine-H3 receptor inverse-agonistic effect and is useful for preventive or remedy of metabolic system diseases, circulatory system diseases or nervous system diseases.

17 Claims, No Drawings

QUINAZOLINE DERIVATIVE

TECHNICAL FIELD

The present invention relates to quinazoline derivatives.

It has been known that, in organisms such as typically mammals, histamine that is a physiologically-active endogenous factor functions as a neurotransmitter and has extensive pharmacological activities (for example, see *Life Science*, Vol. 17, p. 503 (1975)).

Immunohistochemical studies have made it clear that a histamine-agonistic (producing) cell body exists in the nodal papillary nucleus in a posterior hypothalamic region and that histamine-agonistic nerve fibers project histamine in an extremely broad range in the brain, which supports various pharmacological effects of histamine (for example, see *Journal of Comparative Neurology*, Vol. 273, p. 283).

The existence of histamine-agonistic nerves in the nodal papillary nucleus in a posterior hypothalamic region suggests that histamine may have an important role in control of physiological functions relating to brain functions, especially to hypothalamic functions (sleep, vigilance rhythm, incretion, eating and drinking action, sexual action, etc.) (for example, see *Progress in Neurobiology*, Vol. 63, p. 637 (2001)).

The projection of histamine-agonistic nerve fibers to the brain region that relates to vigilance sustenance (e.g., cerebral cortex) suggests the role of histamine in control of vigilance or vigilance-sleep cycle. The projection of histamine-agonistic nerve fibers to many peripheral structures such as hippocampus and amygdaloid complex suggests the role of histamine in control of autonomic nerves, emotion, control of motivated action and learning/memory process.

When released from producing cells, histamine acts with a specific polymer that is referred to as a receptor on the surface of a cell membrane or inside a target cell, therefore exhibiting its pharmacological effects for control of various body functions. Heretofore, four types of histamine receptors have been found. In particular, the presence of a histamine receptor that participates in the central and peripheral nervous functions, a histamine-H3 receptor, has been shown by various pharmacological and physiological studies (for example, see *Trends in Pharmacological Science*, Vol. 8, p. 24 (1986)). Recently, human and rodent histamine-H3 receptor genes have been identified and their existence has been revealed (for example, see *Molecular Pharmacology*, Vol. 55, p. 1101 (1999)).

The histamine-H3 receptor exists in the presynaptic membrane of central or peripheral neurocytes and functions as a self-receptor, therefore controlling the release of histamine and controlling even the release of other neurotransmitters. Specifically, a histamine-H3 receptor agonist, or its antagonist or inverse-agonist controls the release of histamine, noradrenaline, serotonin, acetylcholine or dopamine from nerve ending. The release of these neurotransmitters is inhibited by a histamine-H3 receptor agonist such as (R)-(α)-methylhistamine, and is promoted by a histamine-H3 receptor antagonist or inverse-agonist such as thioperamide (for example, see *Trends in Pharmacological Science*, Vol. 19, p. 177 (1998)).

DISCLOSURE OF THE INVENTION

An object of the invention is to provide a novel substance having a histamine-H3 receptor antagonistic effect (an effect of inhibiting histamine from binding to a histamine-H3 receptor) or a histamine-H3 receptor inverse-agonistic effect (an effect of inhibiting the homeostatic activity that a histamine-H3 receptor has), or that is, a novel substance that acts as a histamine-H3 receptor agonist or antagonist in living bodies.

We, the present inventors have found that a specific quinazoline derivative acts as a histamine-H3 receptor antagonist or inverse-agonist, and have completed the invention.

Accordingly, for attaining the above object, the invention provides compounds or salts of the following (1) to (32):

(1) A compound or its pharmaceutically-acceptable salt of a formula (I):

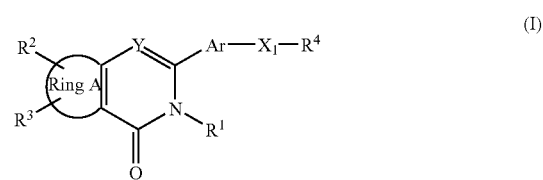

wherein $R^1$ represents an aryl group; a 5- or 6-membered heteroaryl group having, in the ring, from 1 to 4 hetero atoms selected from a group consisting of a nitrogen atom, a sulfur atom and an oxygen atom; a heteroarylalkyl group; a linear or branched lower alkyl group; an aralkyl group; an alkoxy group; an alkoxycarbonyl group; or an alkanoyl group; wherein the aryl group, the heteroaryl group, the heteroarylalkyl group or the aralkyl group may be substituted with a lower alkyl group, a halogen atom or an alkoxy group; and the lower alkyl group may be substituted with a hydroxyl group, a halogen atom or an alkoxy group;

$R^2$ and $R^3$ are the same or different, each represent a hydrogen atom; an amino group; an alkylamino group; a dialkylamino group; a nitro group; a cyano group; a hydroxyl group; a lower alkylsulfonyl group; a halogen atom; a lower alkyl group wherein the lower alkyl group may be substituted with a halogen atom; a cycloalkyl group wherein the cycloalkyl group may be substituted with a halogen atom; an alkoxy group wherein the alkoxy group may be substituted with a halogen atom or a hydroxyl group; a cycloalkoxy group wherein the cycloalkoxy group may be substituted with a halogen atom; an aryloxy group; an aralkyloxy group; a heteroaryloxy group; a heteroarylalkyloxy group; an aryl group; a heteroaryl group; an arylcarbamoyl group; a heteroarylcarbamoyl group; an arylalkylcarbamoyl group; a heteroarylalkylcarbamoyl group; a mono- or di-lower alkylcarbamoyl group; an aryloxycarbonylamino group; an arylalkyloxycarbonylamino group; a lower alkyloxycarbonylamino group; an alkylcarbonylamino group; an arylcarbonylamino group; a heteroarylcarbonylamino group; an arylalkylcarbonylamino group; a heteroarylalkylcarbonylamino group; an alkanoyl group; an arylcarbonyl group; an arylalkylcarbonyl group; a formyl group; a hydroxyl group; an alkylthio group; an alkoxycarbonylamino group; a lower alkylsulfonylamino group; an arylsulfonylamino group; an alkylaminosulfonyl group; or an arylaminosulfonyl group;

$R^4$ represents a group of a formula (II):

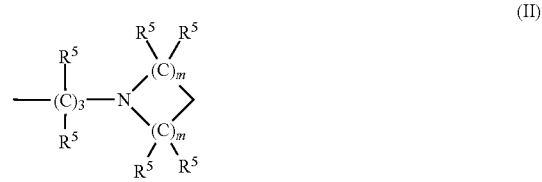

wherein $R^5$ each independently represents a hydrogen atom, a lower alkyl group, a hydroxyl group or a halogen atom; m each independently indicates from 0 to 4, provided that m's are not 0 at the same time, or a group of a formula (III):

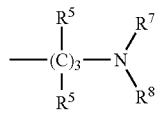

(III)

wherein $R^5$ has the same meaning as above; $R^7$ and $R^8$ each independently represent a lower alkyl group, an arylalkyl group, or a heteroarylalkyl group, excepting that $R^7$ and $R^8$ are a lower alkyl group at the same time, or
a group of a formula (IV):

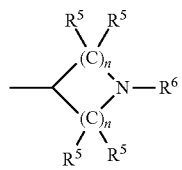

(IV)

wherein $R^5$ has the same meaning as above; $R^6$ represents a linear or branched lower alkyl group, or a cycloalkyl group, wherein 1 or 2 methylene groups in the cycloalkyl group may be substituted with O, S or N; n each independently indicates from 0 to 4, provided that n's must not be 0 at the same time, or a group of a formula (V):

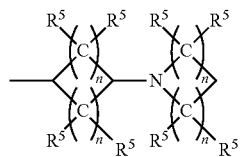

(V)

wherein $R^5$ and n have the same meanings as above;
$X_1$ represents NH, O or S;
Y represents N or C;
Ar represents an aryl group or a heteroaryl group, wherein the aryl group or the heteroaryl group may have 1 or 2 substituents of a lower alkyl group, an alkoxy group or a halogen atom on Ar;
the ring A represents a 5- or 6-membered heteroaryl group having 1 or 2 nitrogen atoms or oxygen atoms in the ring, or represents a phenyl group.

(2) The compound or its pharmaceutically-acceptable salt of above (1), wherein $X_1$ is O and Y is N.

(3) The compound or its pharmaceutically-acceptable salt of above (1), wherein $X_1$ is O; Y is N; and Ar is a divalent group derived from benzene or pyridine by removing two hydrogen atoms therefrom, which may be mono- or di-substituted with a lower alkyl group, a lower alkoxy group or a halogen atom.

(4) The compound or its pharmaceutically-acceptable salt of above (1), wherein $X_1$ is O; Y is N; Ar is a divalent group derived from benzene or pyridine by removing two hydrogen atoms therefrom, which may be mono- or di-substituted with a lower alkyl group, a lower alkoxy group or a halogen atom; and the ring A is a benzene ring or a pyridine ring.

(5) The compound or its pharmaceutically-acceptable salt of above (4), wherein the ring A is a benzene ring.

(6) The compound or its pharmaceutically-acceptable salt of above (4), wherein the ring A is a pyridine ring.

(7) The compound or its pharmaceutically-acceptable salt of above (4), (5) or (6), wherein $R^4$ is a group of a formula (II):

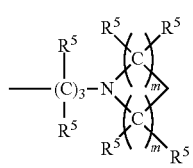

(II)

wherein the symbols have the same meanings as above.

(8) The compound or its pharmaceutically-acceptable salt of above (7), wherein m is 1 or 2.

(9) The compound or its pharmaceutically-acceptable salt of above (4), (5) or (6), wherein $R^4$ is a group of a formula (IV):

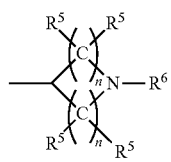

(IV)

wherein the symbols have the same meanings as above.

(10) The compound or its pharmaceutically-acceptable salt of above (9), wherein n is 2.

(11) The compound or its pharmaceutically-acceptable salt of any of above (1) to (10), wherein $R^1$ is a lower alkyl group.

(12) The compound or its pharmaceutically-acceptable salt of any of above (1) to (10), wherein $R^1$ is a methyl group.

(13) The compound or its pharmaceutically-acceptable salt of any of above (1) to (12), wherein at least one of $R^2$ and $R^3$ is a hydrogen atom.

(14) The compound or its pharmaceutically-acceptable salt of any of above (1) to (12), wherein at least one of $R^2$ and $R^3$ is a hydrogen atom, and the other is a hydrogen atom; a halogen atom; a lower alkyl group wherein the lower alkyl group may be substituted with from 1 to 3, the same or different halogen atoms; a lower alkoxy group wherein the lower alkoxy group may be substituted with from 1 to 3, the same or different halogen atoms; a nitro group; a lower alkylcarbonylamino group wherein the lower alkyl group in the lower alkylcarbonylamino group may be substituted with from 1 to 3, the same or different halogen atoms; or a lower alkylsulfonylamino group.

(15) The compound or its pharmaceutically-acceptable salt of any of above (1) to (12), wherein at least one of $R^2$ and $R^3$ is a hydrogen atom, and the other is a hydrogen atom, a lower alkoxy group, wherein the lower alkoxy group may be substituted with from 1 to 3, the same or different halogen atoms, or a lower alkyl group, wherein the lower alkyl group may be substituted with from 1 to 3, the same or different halogen atoms.

(16) The compound or its pharmaceutically-acceptable salt of above (1), wherein the compound of formula (I) is the following:

3,8-dimethyl-2-[4-(3-piperidin-1-ylpropoxy)phenyl]-4(3H)-quinazolinone;
3-methyl-2-[4-(3-piperidin-1-ylpropoxy)phenyl]-4(3H)-quinazolinone;
3-ethyl-2-[4-(3-piperidin-1-ylpropoxy)phenyl]-4(3H)-quinazolinone;
3,6-dimethyl-2-[4-(3-piperidin-1-ylpropoxy)phenyl]-4(3H)-quinazolinone;
3,5-dimethyl-2-[4-(3-piperidin-1-ylpropoxy)phenyl]-4(3H)-quinazolinone;
3-propyl-2-[4-(3-piperidin-1-ylpropoxy)phenyl]-4(3H)-quinazolinone;
3-benzyl-2-[4-(3-piperidin-1-ylpropoxy)phenyl]-4(3H)-quinazolinone;
3-ethyl-2-[3-(3-piperidin-1-ylpropoxy)phenyl]-4(3H)-quinazolinone;
3-isopropyl-2-[4-(3-piperidin-1-ylpropoxy)phenyl]-4(3H)-quinazolinone;
2-[4-(3-piperidin-1-ylpropoxy)phenyl]-3-phenyl-4(3H)-quinazolinone;
2-[4-(3-piperidin-1-ylpropoxy)phenyl]-3-(2,2,2-trifluoroethyl)₄(3H)-quinazolinone;
3,8-dimethyl-2-[4-(3-pyrrolidin-1-ylpropoxy)phenyl]-4(3H)-quinazolinone;
2-(2-methoxy-4-{3-[(3S)-3-methylpiperidin-1-yl]propoxy}phenyl)-3-methylquinazolin-4(3H)-one;
8-methoxy-2-(2-methoxy-4-{3-[(3S)-3-methylpiperidin-1-yl]propoxy}phenyl)-3-methylquinazolin-4(3H)-one;
3-methyl-2-[4-(3-piperidin-1-ylpropoxy)phenyl]pyrido[2,3-d]-pyrimidin-4(3H)-one;
3-methyl-2-[4-(3-pyrrolidin-1-ylpropoxy)phenyl]-4(3H)-quinazolinone;
3-methyl-2-[4-(1-cyclopentyl-4-piperidinyloxy)phenyl]-4(3H)-quinazolinone;
6-chloro-3-methyl-2-[4-(3-piperidin-1-ylpropoxy)phenyl]pyrido[3,4-d]-pyrimidin-4(3H)-one;
3,7-dimethyl-2-[4-(3-piperidin-1-ylpropoxy)phenyl]-4(3H)-quinazolinone;
3-methyl-2-[4-(3-pyrrolidin-1-ylpropoxy)phenyl]pyrido[2,3-d]-pyrimidin-4(3H)-one;
2-[4-(1-cyclopentyl-4-piperidinyloxy)phenyl]-3-methylpyrido[2,3-d]-pyrimidin-4(3H)-one;
2-[4-(1-cyclobutyl-4-piperidinyloxy)phenyl]-3-methylpyrido[2,3-d]-pyrimidin-4(3H)-one;
2-[4-(1-cyclobutyl-4-piperidinyloxy)phenyl]-3-(2-methoxyethyl)pyrido[2,3-d]pyrimidin-4(3H)-one;
2-{4-[(1-cyclobutylpiperidin-4-yl)oxy]phenyl}-8-methoxyquinazolin-4(3H)-one;
7-bromo-2-{4-[(1-cyclopentylpiperidin-4-yl)oxy]-2-methoxyphenyl}-3-methylpyrido[3,2-d]pyrimidin-4(3H)-one;
7-bromo-2-{4-[(1-cyclobutylpiperidin-4-yl)oxy]-2-methoxyphenyl}-3-methylpyrido[3,2-d]pyrimidin-4(3H)-one;
2-{6-[(1-cyclobutylpiperidin-4-yl)oxy]pyridin-3-yl}-8-methoxy-3-methylquinazolin-4(3H)-one;
6-chloro-2-{4-[(1-cyclopentylpiperidin-4-yl)oxy]phenyl}-3-methylpyrido[3,4-d]pyrimidin-4(3H)-one;
2-{4-[(1-cyclobutylpiperidin-4-yl)oxy]phenyl-8-methoxy-3-methylpyrido[3,4-d]pyrimidin-4(3H)-one;
6-chloro-2-{4-[(1-cyclobutylpiperidin-4-yl)oxy]phenyl}-3-methylpyrido[3,4-d]pyrimidin-4(3H)-one;
6-chloro-2-[2-methoxy-4-(3-pyrrolidin-1-ylpropoxy)phenyl]-3-methylpyrido[3,4-d]pyrimidin-4(3H)-one;
2-{4-[(1-cyclobutylpiperidin-4-yl)oxy]phenyl}-8-methylquinazolin-4(3H)-one;
8-methoxy-3-methyl-2-[4-(3-pyrrolidin-1-ylpropoxy)phenyl]pyrido[3,4-d]pyrimidin-4(3H)-one;
2-{4-[(1-cyclolopentylpiperidin-4-yl)oxy]phenyl}-8-methoxy-3-methylpyrido[3,4-d]pyrimidin-4(3H)-one;
8-chloro-2-{4-[(1-cyclobutylpiperidin-4-yl)oxy]phenyl}-3-methylquinazolin-4(3H)-one;
2-{4-[(1-cyclobutylpiperidin-4-yl)oxy]phenyl}-3-methyl-8-(trifluoromethyl)quinazolin-4(3H)-one;
2-{6-[(1-cyclobutylpiperidin-4-yl)oxy]pyridin-3-yl}-3,8-dimethylquinazolin-4(3H)-one;
6-chloro-2-{4-[(1-cyclobutylpiperidin-4-yl)oxy]-2-methoxyphenyl}-3-methylpyrido[3,4-d]pyrimidin-4(3H)-one;
6-chloro-2-{4-[(1-cyclopentylpiperidin-4-yl)oxy]-2-methoxyphenyl}-3-methylpyrido[3,4-d]pyrimidin-4(3H)-one;
2-{4-[(1-cyclobutylpiperidin-4-yl)oxy]phenyl-8-fluoro-3-methylquinazolin-4(3H)-one;
2-{4-[(1-cyclopentylpiperidin-4-yl)oxy]phenyl-8-fluoro-3-methylquinazolin-4(3H)-one;
8-fluoro-2-(2-methoxy-4-{3-[(3S)-3-methylpiperidin-1-yl]propoxy}phenyl)-3-methylquinazolin-4-(3H)-one;
5-fluoro-3-methyl-2-[4-(3-pyrrolidin-1-ylpropoxy)phenyl]quinazolin-4(3H)-one;
2-{4-[(1-cyclobutylpiperidin-4-yl)oxy]phenyl}-5-fluoro-3-methylquinazolin-4(3H)-one;
2-{4-[(1-cyclobutylpiperidin-4-yl)oxy]phenyl}-3,8-dimethylpyrido[4,3-d]pyrimidin-4(3H)-one;
2-{2-[(1-cyclobutylpiperidin-4-yl)oxy]pyrimidin-5-yl}-8-methoxy-3-methylquinazolin-4(3H)-one;
2-{2-[(1-cyclobutylpiperidin-4-yl)oxy]pyrimidin-5-yl}-8-methoxy-3-methylpyrido[3,4-d]pyrimidin-4(3H)-one;
2-{6-[(1-cyclobutylpiperidin-4-yl)oxy]pyridin-3-yl}-8-methoxy-3-methylpyrido[3,4-d]pyrimidin-4(3H)-one;
2-{4-[(1-cyclobutylpiperidin-4-yl)oxy]phenyl}-6-methoxy-3-methylpyrido[3,4-d]pyrimidin-4(3H)-one;
2-{4-[(1-cyclopentylpiperidin-4-yl)oxy]phenyl}-6-methoxy-3-methylpyrido[3,4-d]pyrimidin-4(3H)-one;
3-methyl-2-(4-{3-[(3S)-3-methylpiperidin-1-yl]propoxy}phenyl)pyrido[3,2-d]pyrimidin-4(3H)-one;
2-{4-[(1-cyclobutylpiperidin-4-yl)oxy]phenyl}-3-methylpyrido[3,2-d]pyrimidin-4(3H)-one;
2-{4-[(1-cyclopentylpiperidin-4-yl)oxy]phenyl-3-methylpyrido[3,2-d]pyrimidin-4(3H)-one;
3,8-dimethyl-2-(4-{3-[(3S)-3-methylpiperidin-1-yl]propoxy}phenyl)pyrido[4,3-d]pyrimidin-4(3H)-one;
7-bromo-3-methyl-2-(4-{3-[(3S)-3-methylpiperidin-1-yl]propoxy}phenyl)pyrido[3,2-d]pyrimidin-4(3H)-one;
7-methoxy-3-methyl-2-[4-(3-pyrrolidin-1-ylpropoxy)phenyl]quinazolin-4(3H)-one;
7-methoxy-3-methyl-2-[4-(3-[(3S)-3-methylpiperidin-1-yl]propoxy)phenyl]quinazolin-4(3H)-one;
2-{4-[(1-cyclobutylpiperidin-4-yl)oxy]phenyl}-7-methoxy-3-methylquinazolin-4(3H)-one;
2-{4-[(1-cyclobutylpiperidin-4-yl)oxy]phenyl}-8-methoxy-3-methylpyrido[3,2-d]pyrimidin-4(3H)-one;
7-bromo-2-[2-(2-fluoroethoxy)-4-(3-piperidin-1-ylpropoxy)phenyl]-3-methylquinazolin-4(3H)-one;
6-chloro-2-[2-(2-fluoroethoxy)-4-(3-pyrrolidin-1-ylpropoxy)phenyl]-3-methylpyrido[3,4-d]pyrimidin-4(3H)-one;
2-{4-[(1-cyclobutylpiperidin-4-yl)oxy]phenyl}-4-(2-fluoroethoxy)-8-methoxyquinazoline;
2-{4-[(1-cyclobutylpiperidin-4-yl)oxy]phenyl}-3-methylpyrido[3,4-d]pyrimidin-4(3H)-one;
2-{4-[(1-cyclopentylpiperidin-4-yl)oxy]phenyl}-3-methylpyrido[3,4-d]pyrimidin-4(3H)-one;
2-{4-[(1-cyclobutylpiperidin-4-yl)oxy]phenyl}-7-(2-fluoroethyl)-3-methyl-3,7-dihydropyrido[3,4-d]pyrimidine-4,8-dione;

2-{4-[(1-cyclopentylpiperidin-4-yl)oxy]phenyl}-7-(2-fluoroethyl)-3-methyl-3,7-dihydropyrido[3,4-d]pyrimidine-4,8-dione;
2-{4-[(1-cyclobutylpiperidin-4-yl)oxy]phenyl}-8-(difluoromethoxy)-3-methylpyrido[3,4-d]pyrimidin-4(3H)-one;
2-{4-[(1-cyclobutylpiperidin-4-yl)oxy]phenyl}-7-(difluoromethyl)-3-methyl-3,7-dihydropyrido[3,4-d]pyrimidine-4,8-dione;
3-methyl-2-[4-(3-piperidin-1-ylpropoxy)-phenyl]pyrido[3,4-d]pyrimidin-4(3H)-one;
3-methyl-2-[3-(3-piperidin-1-ylpropoxy)-phenyl]-6-methylsulfonylamino-4(3H)-quinazolinone;
3-methyl-2-[3-(3-piperidin-1-ylpropoxy)-phenyl]-7-methylsulfonylamino-4(3H)-quinazolinone;
3-methyl-7-nitro-2-[3-(3-piperidin-1-ylpropoxy)phenyl]-4(3H)-quinazolinone;
3-methyl-7-methylsulfonylamino-2-[4-(3-pyrrolidin-1-ylpropoxy)phenyl]-4(3H)-quinazolinone;
3-methyl-6-methylsulfonylamino-2-[4-(3-pyrrolidin-1-ylpropoxy)phenyl]-4(3H)-quinazolinone;
6-acetylamino-3-methyl-2-[4-(3-piperidin-1-ylpropoxy)phenyl]-4(3H)-quinazolinone;
3-methyl-2-[4-(3-piperidin-1-ylpropoxy)phenyl]-6-trifluoromethylcarbonylamino-4(3H)-quinazolinone;
3-methyl-2-[2-methyl-4-(3-pyrrolidin-1-ylpropoxy)phenyl]-4(3H)-quinazolinone;
3-methyl-2-[2-fluoro-4-(3-pyrrolidin-1-ylpropoxy)-phenyl]-4(3H)-quinazolinone;
6-bromo-3-methyl-2-[3-methoxy-4-(3-pyrrolidin-1-ylpropoxy)-phenyl]-4(3H)-quinazolinone;
6-bromo-3-methyl-2-[2-methoxy-4-(3-pyrrolidin-1-ylpropoxy)-phenyl]-4(3H)-quinazolinone;
2-[2-methoxy-4-(3-pyrrolidin-1-ylpropoxy)-phenyl]-3-methylpyrido[2,3-d]pyrimidin-4(3H)-one;
8-methoxy-3-methyl-2-[4-(3-pyrrolidin-1-ylpropoxy)phenyl]quinazolin-4(3H)-one;
3-allyl-2-[4-(3-pyrrolidin-ylpropoxy)phenyl]pyrido[2,3-d]pyrimidin-4(3H)-one;
2-[2-methoxy-4-(3-piperidin-1-ylpropoxy)-phenyl]-3-methylpyrido[2,3-d]pyrimidin-4(3H)-one;
3-methyl-2-[2-methyl-4-(1-cyclobutyl-4-piperidinyloxy)phenyl]-4(3H)-quinazolinone;
3-methyl-2-[2-methyl-4-(1-cyclopentyl-4-piperidinyloxy)phenyl]-4(3H)-quinazolinone;
3-methyl-2-[2-methyl-4-(1-cyclohexyl-4-piperidinyloxy)phenyl]-4(3H)-quinazolinone;
3-methyl-2-[4-(1-cyclobutyl-4-piperidinyloxy)phenyl]-4(3H)-quinazolinone;
3-methyl-2-[4-(1-cyclopropyl-4-piperidinyloxy)phenyl]-4(3H)-quinazolinone;
8-methoxy-3-methyl-2-[4-(1-cyclobutyl-4-piperidinyloxy)phenyl]-4(3H)-quinazolinone;
6-methoxy-3-methyl-2-[4-(1-cyclobutyl-4-piperidinyloxy)phenyl]-4(3H)-quinazolinone;
5-methoxy-3-methyl-2-[4-(1-cyclobutyl-4-piperidinyloxy)phenyl]-4(3H)-quinazolinone;
8-methoxy-3-methyl-2-[4-(1-cyclopropyl-4-piperidinyloxy)phenyl]-4(3H)-quinazolinone;
5-methoxy-3-methyl-2-[4-(1-cyclobutyl-4-piperidinyloxy)phenyl]-4(3H)-quinazolinone;
2-{4-[(1-cyclobutylpiperidin-4-yl)oxy]phenyl}-3,8-dimethylquinazolin-4(3H)-one;
7-bromo-2-{4-[(1-cyclobutylpiperidin-4-yl)oxy]phenyl}-3-methylpyrido[3,2-d]pyrimidin-4(3H)-one;
7-bromo-2-{4-[(1-cyclopentylpiperidin-4-yl)oxy]phenyl}-3-methylpyrido[3,2-d]pyrimidin-4(3H)-one;
2-{4-[(1-cyclobutylpiperidin-4-yl)oxy]-2-methoxyphenyl}-3-methylpyrido[2,3-d]pyrimidin-4(3H)-one;
2-{4-[(1-cyclopentylpiperidin-4-yl)oxy]-2-methoxyphenyl}-3-methylpyrido[2,3-d]pyrimidin-4(3H)-one;
2-{4-[(1-cyclopropylpiperidin-4-yl)oxy]phenyl}-3-ethyl-8-methylquinazolin-4(3H)-one;
2-{4-[(1-cyclobutylpiperidin-4-yl)oxy]phenyl}-3-ethyl-8-methylquinazolin-4(3H)-one;
2-{4-[(1-cyclopentylpiperidin-4-yl)oxy]phenyl}-3-ethyl-8-methylquinazolin-4(3H)-one;
2-{4-[(1-cyclobutylpiperidin-4-yl)oxy]-2-fluorophenyl}-3-methylquinazolin-4(3H)-one;
2-{4-[(1-cyclopentylpiperidin-4-yl)oxy]-2-fluorophenyl}-3-methylquinazolin-4(3H)-one; or
tert-butyl 4-oxo-2-[4-(3-piperidin-1-ylpropoxy)phenyl]-[3,4H]-quinazolinecarboxylate.

(17) The compound or its pharmaceutically-acceptable salt of above (1), wherein the compound of formula (I) is 3-methyl-2-[4-(3-piperidin-1-ylpropoxy)phenyl]pyrido[2,3-d]pyrimidin-4(3H)-one.

(18) The compound or its pharmaceutically-acceptable salt of above (1), wherein the compound of formula (I) is 3-methyl-2-[4-(3-pyrrolidin-1-ylpropoxy)phenyl]-4(3H)-quinazolinone.

(19) The compound or its pharmaceutically-acceptable salt of above (1), wherein the compound of formula (I) is 2-[4-(1-cyclopentyl-4-piperidinyloxy)phenyl]-3-methylpyrido[2,3-d]pyrimidin-4(3H)-one.

(20) The compound or its pharmaceutically-acceptable salt of above (1), wherein the compound of formula (I) is 2-[4-(1-cyclobutyl-4-piperidinyloxy)phenyl]-3-methylpyrido[2,3-d]-pyrimidin-4(3H)-one.

(21) The compound or its pharmaceutically-acceptable salt of above (1), wherein the compound of formula (I) is 2-{4-[(1-cyclobutylpiperidin-4-yl)oxy]phenyl}-8-methoxy-3-methylpyrido[3,4-d]pyrimidin-4(3H)-one.

(22) The compound or its pharmaceutically-acceptable salt of above (1), wherein the compound of formula (I) is 2-{6-[(1-cyclobutylpiperidin-4-yl)oxy]pyridin-3-yl}-8-methoxy-3-methylpyrido[3,4-d]pyrimidin-4(3H)-one.

(23) The compound or its pharmaceutically-acceptable salt of above (1), wherein the compound of formula (I) is 2-{4-[(1-cyclobutylpiperidin-4-yl)oxy]phenyl}-6-methoxy-3-methylpyrido[3,4-d]pyrimidin-4(3H)-one.

(24) The compound or its pharmaceutically-acceptable salt of above (1), wherein the compound of formula (I) is 3-methyl-2-(4-{3-[(3S)-3-methylpiperidin-1-yl]propoxy}phenyl)pyrido[3,2-d]pyrimidin-4(3H)-one.

(25) The compound or its pharmaceutically-acceptable salt of above (1), wherein the compound of formula (I) is 2-{4-[(1-cyclobutylpiperidin-4-yl)oxy]phenyl}-3-methylpyrido[3,2-d]pyrimidin-4(3H)-one.

(26) The compound or its pharmaceutically-acceptable salt of above (1), wherein the compound of formula (I) is 2-{4-[(1-cyclobutylpiperidin-4-yl)oxy]phenyl}-8-methoxy-3-methylpyrido[3,2-d]pyrimidin-4(3H)-one.

(27) The compound or its pharmaceutically-acceptable salt of above (1), wherein the compound of formula (I) is 2-{4-[(1-cyclobutylpiperidin-4-yl)oxy]phenyl}-3-methylpyrido[3,4-d]pyrimidin-4(3H)-one.

(28) The compound or its pharmaceutically-acceptable salt of above (1), wherein the compound of formula (I) is 3-methyl-2-[2-methyl-4-(3-pyrrolidin-1-ylpropoxy)phenyl]-4(3H)-quinazolinone.

(29) The compound or its pharmaceutically-acceptable salt of above (1), wherein the compound of formula (I) is 3-methyl-2-[2-methyl-4-(1-cyclobutyl-4-piperidinyloxy)phenyl]-4(3H)-quinazolinone.

(30) The compound or its pharmaceutically-acceptable salt of above (1), wherein the compound of formula (I) is 3-methyl-2-[4-(1-cyclobutyl-4-piperidinyloxy)phenyl]-4(3H)-quinazolinone.

(31) The compound or its pharmaceutically-acceptable salt of above (1), wherein the compound of formula (I) is 8-methoxy-3-methyl-2-[4-(1-cyclobutyl-4-piperidinyloxy)phenyl]-4(3H)-quinazolinone.

(32) The compound or its pharmaceutically-acceptable salt of above (1), wherein the compound of formula (I) is 2-{4-[(1-cyclobutylpiperidin-4-yl)oxy]phenyl}-3,8-dimethylquinazolin-4(3H)-one.

(33) A histamine H3-receptor antagonist comprising a compound or its pharmaceutically-acceptable salt of any one of claims 1 to 35.

(34) A histamine H3-receptor inverse-agonist comprising a compound or its pharmaceutically-acceptable salt of any one of claims 1 to 45.

(35) A preventive or remedy containing, as the active ingredient thereof, a compound or its pharmaceutically-acceptable salt of any of claims 1 to 45, which is for metabolic system diseases, circulatory system diseases or nervous system diseases.

(36) The preventive or remedy of above (35), wherein the metabolic system diseases are at least one selected from obesity, diabetes, hormone secretion disorder, hyperlipemia, gout and fatty liver.

(37) The preventive or remedy of above (35), wherein the circulatory system diseases are at least one selected from stenocardia, acute/congestive cardiac insufficiency, cardiac infarction, coronary arteriosclerosis, hypertension, nephropathy and electrolyte metabolism disorder.

(38) The preventive or remedy of above (35), wherein the nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

(39) The preventive or remedy of above (35), wherein the nervous system diseases are at least one selected from idiopathic hypersomnia, repetitive hypersomnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia.

(40) A preventive or remedy for metabolic system diseases, circulatory system diseases or nervous system diseases, which contains, as the active ingredients thereof, a compound or its pharmaceutically-acceptable salt of any one of (1) to (32) and an additional drug.

(41) The preventive or remedy of above (40), wherein the additional drug is a remedy for diabetes.

(42) The preventive or remedy of above (40), wherein the additional drug is a remedy for hyperlipemia.

(43) The preventive or remedy of above (40), wherein the additional drug is a remedy for hypertension.

(44) The preventive or remedy of above (40), wherein the additional drug is an anti-obesity drug.

(45) A preventive or remedy for metabolic system diseases, circulatory system diseases or nervous system diseases, which contains the following (i), (ii) and (iii):
(i) a compound or its pharmaceutically-acceptable salt of any one of above (1) to (32);
(ii) at least one selected from a group of the following (a) to (g):
(a) a histamine-H3 receptor antagonist or inverse-agonist except (i);
(b) a biguanide,
(c) a PPAR-agonist;
(d) insulin,
(e) somatostatin,
(f) an α-glucosidase inhibitor,
(g) an insulin secretion promoter;
(iii) a pharmaceutically-acceptable carrier.

The compounds or their salts of above (1) to (32) act as a histamine-H3 receptor antagonist or inverse-agonist in living bodies. Accordingly, the invention provides a histamine-H3 receptor antagonist or inverse-agonist comprising the compound or its pharmaceutically-acceptable salt of above (1) to (32).

Recent studies have shown that a histamine-H3 receptor has extremely high homeostatic activities (activities observed in the absence of an endogenous agonistic factor (e.g., histamine)) in the receptor-expressing cells/tissues or in a membrane fraction derived from the expressing cells/tissues and even in living bodies (for example, see *Nature*, Vol. 408, p. 860). It is reported that these homeostatic activities are inhibited by an inverse-agonist. For example, thioperamide or syproxyfan inhibits the homeostatic self-receptor activity of a histamine-H3 receptor, and, as a result, promotes the release of neurotransmitters (e.g., histamine) from nerve ending.

Regarding rats, a high-level selective inhibitor of histamine synthase (histidine decarboxylase) inhibits the vigilance of rats, and therefore histamine participates in controlling motive vigilance. Regarding cats, administration of a histamine-H3 receptor agonist, (R)-(α)-methylhistamine to cats increases their deep slow-wave sleep (for example, see *Brain Research*, Vol. 523, p. 325 (1990)).

Contrary to this, a histamine-H3 receptor antagonist or inverse-agonist, thioperamide dose-dependently increases vigilance, and decreases slow-wave and REM sleep (for example, see *Life Science*, Vol. 48, p. 2397 (1991)). A histamine-H3 receptor antagonist or inverse-agonist, thioperamide or GT-2331 reduces emotional cataplexy and sleep of narcoleptic dogs (for example, see *Brain Research*, Vol. 793, p. 279 (1998)).

These informations suggest that the H3 receptor may participate in control of vigilance-sleep and in sleep disorder-associated diseases, further suggesting a possibility that a selective histamine-H3 agonist, antagonist or inverse-agonist may be useful for treatment of sleep disorders or various sleep disorder-associated diseases (for example, idiopathic hypersomnnia, repetitive hypersomnnia, true hypersomnnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia). Accordingly, it may be considered that the compounds or their salts of above (1) to (32) acting as a histamine-H3 receptor antagonist or inverse-agonist may be effective for prevention and remedy of sleep disorders and various sleep disorder-associated diseases.

In rats, a histamine-H3 receptor antagonist or inverse-agonist, thioperamide or GT-2331 relieves the condition of learning disorder (LD) and attention deficit hyperactivity disorder (ADHD) (for example, see *Life Science*, Vol. 69, p. 469 (2001)). Further in rats, a histamine-H3 receptor agonist, (R)-(α)-methylhistamine lowers their object cognitive and learning effects in the object cognition test and the passive turnout test with them.

On the other hand, in a scopolamine-induced amnesia test, a histamine-H3 receptor antagonist or inverse-agonist, thioperamide dose-dependently relieves amnesia induced by the chemical (for example, see *Pharmacology, Biochemistry and Behavior*, Vol. 68, p. 735 (2001)).

These informations suggest a possibility that a histamine-H3 receptor antagonist or inverse-agonist may be useful for prevention or remedy of memory/learning disorder and various diseases accompanied by it (e.g., Alzheimer's disease, Parkinson's disease, attention deficit/hyperactivity disorder). Accordingly, it may also be considered that the compounds or their salts of above (1) to (32) may be effective for prevention or remedy of such memory/learning disorder and various diseases accompanied by it.

Regarding rats, administration of histamine to their ventricle inhibits their eating action, therefore suggesting that histamine may participate in control of eating action (for example, see *Journal of Physiology and Pharmacology*, Vol. 49, p. 191 (1998)). In fact, a histamine-H3 receptor antagonist or inverse-agonist, thioperamide dose-dependently inhibits eating action and promotes intracerebral histamine release (for example, see *Behavioral Brain Research*, Vol. 104, p. 147 (1999)).

These informations suggest that a histamine H3 receptor may participate in eating action control, further suggesting that a histamine-H3 antagonist or inverse-agonist may be useful for prevention or remedy of metabolic system diseases (metabolic syndromes) such as eating disorder, obesity, diabetes, emaciation, hyperlipemia. Accordingly, it may be considered that the compounds or their salts of above (1) to (32) may be effective also for prevention or remedy of such metabolic system diseases.

In rats, a histamine-H3 receptor agonist, (R)-(α)-methylhistamine dose-dependently lowers their basal diastolic pressure, and its action is antagonized by a histamine-H3 receptor antagonist or inverse-agonist, thioperamide (for example, see *European Journal of Pharmacology*, Vol. 234, p. 129, (1993)).

These informations suggest that a histamine-H3 receptor may participate in control of blood pressure, heart beat and cardiac output, further suggesting that a histamine-H3 receptor agonist, antagonist or inverse-agonist may be useful for prevention or remedy of circulatory system diseases such as hypertension and various cardiac disorders. Accordingly, it may be considered that the compounds or their salts of above (1) to (32) may be effective also for prevention or remedy of such circulatory system diseases.

In mice, a histamine-H3 receptor antagonist or inverse-agonist, thioperamide dose-dependently inhibits the spasm induced by electric shock or the epileptoid seizure induced by pentylene tetrazole (PTZ) (for example, see *European Journal of Pharmacology*, Vol. 234, p. 129 (1993) and *Pharmacology, Biochemistry and Behavior*, Vol. 68, p. 735 (2001)).

These informations suggest that a histamine-H3 receptor antagonist or inverse-agonist may be useful for prevention or remedy of epilepsy or central spasm. Accordingly, it may be considered that the compounds or their salts of above (1) to (32) may be effective also for prevention or remedy of such epilepsy or central spasm.

Accordingly, the invention further provides a preventive or remedy for metabolic system diseases, circulatory system diseases or nervous system diseases, which contains, as the active ingredient thereof, the compound or its pharmaceutically-acceptable salt of any one of above (1) to (32).

The metabolic system diseases are at least one selected from obesity, diabetes, hormone secretion disorder, hyperlipemia, gout and fatty liver.

The circulatory system diseases are at least one selected from stenocardia, acute/congestive cardiac insufficiency, cardiac infarction, coronary arteriosclerosis, hypertension, nephropathy and electrolyte disorder.

The nervous system diseases are at least one selected from sleep disorder, diseases accompanied by sleep disorder, bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism and tremor.

The nervous system diseases are at least one selected from idiopathic hypersomnia, repetitive hypersomnnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia.

The compounds or their pharmaceutically-acceptable salts of above (1) to (32) may be used, as combined with additional drugs. Accordingly, the invention further provides a preventive or remedy for metabolic system diseases, circulator system diseases or nervous system diseases, which contains the compound or its pharmaceutically-acceptable salt of above (1) to (32) and a additional drug, as the active ingredients thereof. The additional drug includes a remedy for diabetes, a remedy for hyperlipemia, a remedy for hypertension, an anti-obesity drug. Two or more such additional drugs may be used herein, as combined.

The preventive or remedy for metabolic system diseases, circulator system diseases or nervous system diseases, which the invention provides herein, may comprise the following (i), (ii) and (iii):

(i) a compound or its pharmaceutically-acceptable salt of any one of above (1) to (32);

(ii) at least one selected from a group of the following (a) to (g):

(a) a histamine-H3 receptor antagonist or inverse-agonist except (i);

(b) a biguanide, (c) a PPAR (peroxisome proliferator-activated receptor)-agonist;

(d) insulin, (e) somatostatin, (f) an α-glucosidase inhibitor, (g) an insulin secretion promoter;

(iii) a pharmaceutically-acceptable carrier.

BEST MODE FOR CARRYING OUT THE INVENTION

The meanings of the terms used in this description are described first, and then the compounds of the invention are described.

"Aryl group" includes a hydrocarbon-ring aryl group having from 6 to 14 carbon atoms, for example, a phenyl group, a naphthyl group, a biphenyl group, an anthryl group.

"Heteroaryl group" means a 5- or 6-membered monocyclic heteroaryl group having therein from 1 to 4 hetero atoms selected from an oxygen atom, a sulfur atom and a nitrogen atom, or a bicyclic heteroaryl group of the monocyclic heteroaryl group condensed with a benzene ring or a pyridine ring, including, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolyl group, an isoquinolyl group, a quinazolyl group, a quinolidinyl group, an quinoxalinyl group, a cinnolinyl group, a benzimidazolyl group, a imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group.

"Lower alkyl group" means a linear or branched alkyl group having from 1 to 6 carbon atoms, including, for example, a methyl group, an ethyl group, a propyl group, an isopropyl group, a butyl group, an isobutyl group, a sec-butyl group, a tert-butyl group, a pentyl group, an isoamyl group, a neopentyl group, an isopentyl group, a 1,1-dimethylpropyl group, a 1-methylbutyl group, a 2-methylbutyl group, a 1,2-dimethylpropyl group, a hexyl group, an isohexyl group, a 1-methylpentyl group, a 2-methylpentyl group, a 3-methylpentyl group, a 1,1-dimethylbutyl group, a 1,2-dimethylbutyl group, a 2,2-dimethylbutyl group, a 1,3-dimethylbutyl group, a 2,3-dimethylbutyl group, a 3,3-dimethylbutyl group, a 1-ethylbutyl group, a 2-ethylbutyl group, a 1,2,2-trimethylpropyl group, a 1-ethyl-2-methylpropyl group.

"Alkoxy group" means a hydroxyl group of which the hydrogen atom is substituted with the above-mentioned lower alkyl group, including, for example, a methoxy group, an ethoxy group, a propoxy group.

"Cycloalkyl group" is preferably a cycloalkyl group having from 3 to 9 carbon atoms, including, for example, a cyclopropyl group, a cyclobutyl group, a cyclopentyl group, a cyclohexyl group, a cycloheptyl group, a cyclooctyl group, a cyclononyl group.

"Alkylamino group" means an amino group mono-substituted with the above-mentioned lower alkyl group, including, for example, a methylamino group, an ethylamino group, a propylamino group, an isopropylamino group, a butylamino group, a sec-butylamino group, a tert-butylamino group.

"Dialkylamino group" means an amino group di-substituted with the same or different, above-mentioned lower alkyl groups, including, for example, a dimethylamino group, a diethylamino group, a dipropylamino group, a methylpropylamino group, a diisopropylamino group.

"Mono-lower alkylcarbamoyl group" means a carbamoyl group mono-substituted with the above-mentioned lower alkyl group, including, for example, a methylcarbamoyl group, an ethylcarbamoyl group, a propylcarbamoyl group, an isopropylcarbamoyl group, a butylcarbamoyl group, a sec-butylcarbamoyl group, a tert-butylcarbamoyl group.

"Di-lower alkylcarbamoyl group" means a carbamoyl group di-substituted with the same or different, above-mentioned lower alkyl groups, and the "di-lower alkylcarbamoyl group" includes, for example, a dimethylcarbamoyl group, a diethylcarbamoyl group, an ethylmethylcarbamoyl group, a dipropylcarbamoyl group, a methylpropylcarbamoyl group, a diisopropylcarbamoyl group.

"Di-lower alkylcarbamoyl group" also includes a 5- to 8-membered monocyclic group formed together by the nitrogen atom that constitutes the carbamoyl group and the same or different lower alkyl groups bonding to the nitrogen atom; or a bicyclic group formed through condensation of the monocyclic group with a benzene ring or a pyridine ring. Concretely, they include the following groups of formula (VI):

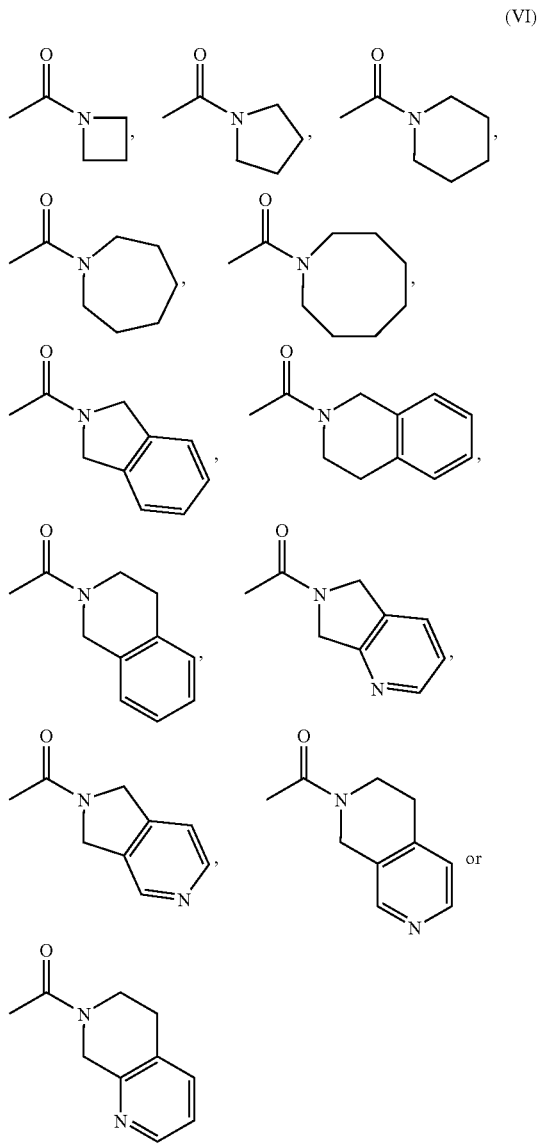

(VI)

"Heteroarylalkyl group" means a group formed by the above-mentioned heteroaryl group and the above-mentioned alkyl group bonding to each other, including, example, a furan-3-yl-methyl group, a furan-2-ylmethyl group, a furan-3-ylethyl group, a furan-2-ylethyl group, a furan-3-ylpropyl group, a furan-2-ylpropyl group, a thiophen-3-ylmethyl group, a thiophen-2-ylmethyl group, a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-pyrrol-2-ylpropyl group, a 1H-imidazol-4-ylmethyl group, a 1H-imidazol-2-ylmethyl group, a 1H-imidazol-5-ylmethyl group, a 1H-imidazol-4-ylethyl group, a 1H-imidazol-2-ylethyl group, a 1H-imidazol-5-ylethyl group, a 1H-imidazol-4-ylpropyl group, a 1H-imidazol-2-ylpropyl group, a 1H-imidazol-5-ylpropyl group, a 1H-[1,2, 3]triazol-4-ylmethyl group, a 1H-[1,2,3]triazol-5-ylmethyl group, a 1H-[1,2,3]triazol-4-ylethyl group, a 1H-[1,2,3]triazol-5-ylethyl group, a 1H-[1,2,3]triazol-4-ylpropyl group, a 1H-[1,2,3]triazol-5-ylpropyl group, a 1H-[1,2,4]triazol-3-ylmethyl group, a 1H-[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group, a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group, a thiazol-4-ylpropyl group, a thiazol-3-ylpropyl group, a thiazol-2-ylpropyl group, a [1,2,4]thiadiazol-3-ylmethyl group, a [1,2,4]thiadiazol-3-ylethyl group, a [1,2,4]thiadiazol-3-ylpropyl group, a [1,2,4]thiadiazol-5-ylmethyl group, a [1,2,4]thiadiazol-5-ylethyl group, a [1,2,4]thiadiazol-5-ylpropyl group, a [1,3,4]thiadiazol-2-2-ylmethyl group, a [1,3,4]thiadiazol-2-ylethyl group, a [1,3,4]thiadiazol-2-ylpropyl group.

"Alkylsulfonyl group" means a group of the above-mentioned alkyl group with a sulfonyl group bonding thereto, including, for example, a methylsulfonyl group, an ethylsulfonyl group, a propylsulfonyl group, an isopropylsulfonyl group, a butylsulfonyl group.

"Alkylsulfonylamino group" means an amino group of which one hydrogen atom is substituted with the above-mentioned alkylsulfonyl group, including, for example, a methylsulfonylamino group, an ethylsulfonylamino group, a propylsulfonylamino group, an isopropylsulfonylamino group, a butylsulfonylamino group, a sec-butylsulfonylamino group, a tert-butylsulfonylamino group, an N-methyl-methylsulfonylamino group, an N-methyl-ethylsulfonylamino group, an N-methyl-propylsulfonylamino group, an N-methyl-isopropylsulfonylamino group, an N-methyl-butylsulfonylamino group, an N-methyl-sec-butylsulfonylamino group, an N-methyl-tert-butylsulfonylamino group, an N-ethyl-methylsulfonylamino group, an N-ethyl-ethylsulfonylamino group, an N-ethyl-propylsulfonylamino group, an N-ethyl-isopropylsulfonylamino group, an N-ethyl-butylsulfonylamino group, an N-ethyl-sec-butylsulfonylamino group, an N-ethyl-tert-butylsulfonylamino group.

"Aralkyl group" means the above-mentioned lower alkyl group having the above-mentioned aryl group, including, for example, a benzyl group, a 1-phenylethyl group, a 2-phenylethyl group, a 1-naphthylmethyl group, a 2-naphthylmethyl group.

"Halogen atom" means, for example, a fluorine atom, a chlorine atom, a bromine atom, an iodine atom.

"Alkoxycarbonylamino group" means an amino group of which one hydrogen atom is substituted with the above-mentioned alkoxycarbonyl group, including, for example, a methoxycarbonylamino group, an ethoxycarbonylamino group, a propoxycarbonylamino group, an isopropoxycarbonylamino group, a butoxycarbonylamino group, a sec-butoxycarbonylamino group, a tert-butoxycarbonylamino group, a pentyloxycarbonylamino group, an N-methyl-methoxycarbonylamino group, an N-methyl-ethoxycarbonylamino group, an N-methyl-propoxycarbonylamino group, an N-methyl-isopropoxycarbonylamino group, an N-methyl-butoxycarbonylamino group, an N-methyl-sec-butoxycarbonylamino group, an N-methyl-tert-butoxycarbonylamino group, an N-ethyl-methoxycarbonylamino group, an N-ethyl-ethoxycarbonylamino group, an N-ethyl-propoxycarbonylamino group, an N-ethyl-isopropoxycarbonylamino group, an N-ethyl-butoxycarbonylamino group, an N-ethyl-sec-butoxycarbonylamino group, an N-ethyl-tert-butoxycarbonylamino group.

"Alkanoyl group" means a group of the above-mentioned alkyl group with a carbonyl group bonding thereto, including, for example, a methylcarbonyl group, an ethylcarbonyl group, a propylcarbonyl group, an isopropylcarbonyl group.

"Alkylthio group" means a group of the above-mentioned alkyl group with a sulfur atom bonding thereto, including, for example, a methylthio group, an ethylthio group, a propylthio group, an isopropylthio group.

"Cycloalkoxy group" means a group of the above-mentioned alkoxy group in which the alkyl group is substituted with a cycloalkyl group, including, for example, a cyclopropoxy group, a cyclobutoxy group, a cyclopentyloxy group, a cyclohexyloxy group, a cycloheptyloxy group.

"Aryloxy group" means a group of the above-mentioned aryl group with an oxygen atom bonding thereto, including, for example, a phenoxy group, a naphthalene-1-yloxy group, a naphthalene-2-yloxy group.

"Aralkyloxy group" means a group of the above-mentioned aralkyl group with an oxygen atom bonding thereto, including, for example, a benzyloxy group, a 1-phenylethyloxy group, a 2-phenylethyloxy group, a 1-naphthylmethyloxy group, a 2-naphthylmethyloxy group.

"Heteroaryloxy group" means a group of the above-defined "heteroaryl group" with an oxy group bonding thereto, including, for example, a furan-2-yloxy group, a furan-3-yloxy group, a thiophen-2-yloxy group, a thiophen-3-yloxy group, a 1H-pyrrol-2-yloxy group, a 1H-pyrrol-3-yloxy group, a 1H-imidazol-2-yloxy group, a 1H-imidazol-4-yloxy group, a 3H-imidazol-4-yloxy group, a 4H-[1,3,4]triazol-3-yloxy group, a 2H-[1,2,4]triazol-3-yloxy group, a 1H-[1,2,4]triazol-3-yloxy group, a thiazol-2-yloxy group, a thiazol-4-yloxy group, a thiazol-5-yloxy group, a pyridin-2-yloxy group, a pyridin-3-yloxy group, a pyridin-4-yloxy group, a pyrimidin-2-yloxy group, a pyrimidin-4-yloxy group, a pyrimidin-5-yloxy group, a pyridazin-3-yloxy group, a pyridazin-4-yloxy group, a 2H-pyrazol-3-yloxy group, a 1H-pyrazol-4-yloxy group, a 1H-pyrazolyl-3-oxy group, a pyrazin-3-yloxy group, a pyrazin-4-yloxy group, a quinolin-2-yloxy group, a quinolin-3-yloxy group, a quinolin-4-yloxy group, an isoquinolin-1-yloxy group, an isoquinolin-3-yloxy group, an isoquinolin-4-yloxy group, a quinazolin-2-yloxy group, a quinazolin-3-yloxy group, a quinoxalin-2-yloxy group, a quinoxalin-3-yloxy group, a cinnolin-3-yloxy group, a cinnolin-4-yloxy group, a 1H-benzimidazol-2-yloxy group, a 1H-imidazo[4,5-b]pyridin-5-yloxy group, a 1H-imidazo[4,5-b]pyridin-6-yloxy group, a 1H-imidazo[4,5-b]pyridin-7-yloxy group, a benzo[d]isoxazol-4-yloxy group, a benzo[d]isoxazol-5-yloxy group, a benzo[d]isoxazol-6-yloxy group, a benzoxazol-4-yloxy group, a benzoxazol-5-yloxy group, a benzoxazol-6-yloxy group.

"Heteroarylalkyloxy group" means the above-mentioned "heteroarylalkyl group" with an oxygen atom bonding thereto, including, for example, a furan-3-ylmethyloxy group, a furan-2-ylmethyloxy group, a furan-3-ylethyloxy group, s furan-2-ylethyloxy group, a furan-3-ylpropyloxy group, a furan-2-ylpropyloxy group, a thiophen-3-ylmethyloxy group, a thiophen-2-ylmethyloxy group, a thiophen-3-ylethyloxy group, a thiophen-2-ylethyloxy group, a thiophen-3-ylpropyloxy group, a thiophen-2-ylpropyloxy group, a 1H-pyrrol-3-ylmethyloxy group, a 1H-pyrrol-2-ylmethyloxy group, a 1H-pyrrol-3-ylethyloxy group, a 1H-pyrrol-2-ylethyloxy group, a 1H-pyrrol-3-ylpropyloxy group, a 1H-pyrrol-2-ylpropyloxy group, a 1H-imidazol-4-ylmethyloxy group, a 1H-imidazol-2-ylmethyloxy group, a 1H-imidazol-5-ylmethyloxy group, a 1H-imidazol-4-ylethyloxy group, a 1H-imidazol-2-ylethyloxy group, a 1H-imidazol-5-ylethyloxy group, a 1H-imidazol-4-ylpropyloxy group, a 1H-imidazol-2-ylpropyloxy group, a 1H-imidazol-5-ylpropyloxy group, a 1H-[1,2,3]triazol-4-ylmethyloxy group, a 1H-[1,2, 3]triazol-5-ylmethyloxy group, a 1H-[1,2,3]triazol-4-ylethyloxy group, a 1H-[1,2,3]triazol-5-ylethyloxy group, a 1H-[1,2,3]triazol-4-ylpropyloxy group, a 1H-[1,2,3]triazol-5-ylpropyloxy group, a 1H-[1,2,4]triazol-3-ylmethyloxy group, a 1H-[1,2,4]triazol-5-ylmethyloxy group, a 1H-[1,2,4]triazol-3-ylethyloxy group, a 1H-[1,2,4]triazol-5-ylethyloxy group, a 1H-[1,2,4]triazol-3-ylpropyloxy group, a 1H-[1,2,4]triazol-5-ylpropyloxy group, a thiazol-4-ylmethyloxy group, a thiazol-3-ylmethyloxy group, a thiazol-2-ylmethyloxy group, a thiazol-4-ylethyloxy group, a thiazol-3-ylethyloxy group, a thiazol-2-ylethyloxy group, a thiazol-4-ylpropyloxy group, a thiazol-3-ylpropyloxy group, a thiazol-2-ylpropyloxy group, a [1,2,4]thiadiazol-3-ylmethyloxy group, a [1,2,4]thiadiazol-3-ylethyloxy group, a [1,2,4]thiadiazol-3-ylpropyloxy group, a [1,2,4]thiadiazol-5-ylmethyloxy group, a [1,2,4]thiadiazol-5-ylethyloxy group, a [1,2,4]thiadiazol-5-ylpropyloxy group, a [1,3,4]thiadiazol-2-2-ylmethyloxy group, a [1,3,4]thiadiazol-2-ylethyloxy group, a [1,3,4]thiadiazol-2-ylpropyloxy group.

"Arylcarbamoyl group" means a carbamoyl group with the above-mentioned, one or two "aryl groups" bonding thereto, including, for example, a phenylcarbamoyl group, a naphthalene-1-ylcarbamoyl group, a naphthalene-2-ylcarbamoyl group.

"Heteroarylcarbamoyl group" means a carbamoyl group with the above-mentioned, one or two "heteroaryl groups" bonding thereto, including, for example, a furan-2-ylcarbamoyl group, a furan-3-ylcarbamoyl group, a thiophen-2-ylcarbamoyl group, a thiophen-3-ylcarbamoyl group, a 1H-pyrrol-2-ylcarbamoyl group, a 1H-pyrrol-3-ylcarbamoyl group, a 1H-imidazol-2-ylcarbamoyl group, a 1H-imidazol-4-ylcarbamoyl group, a 3H-imidazolyl-4-ylcarbamoyl group, a 4H-[1,3,4]triazol-3-ylcarbamoyl group, a 2H-[1,2,4]triazol-3-ylcarbamoyl group, a 1H-[1,2,4]triazol-3-ylcarbamoyl group, a thiazol-2-ylcarbamoyl group, a thiazol-4-ylcarbamoyl group, a thiazol-5-ylcarbamoyl group, a pyridin-2-ylcarbamoyl group, a pyridin-3-ylcarbamoyl group, a pyridin-4-ylcarbamoyl group, a pyrimidin-2-ylcarbamoyl group, a pyrimidin-4-ylcarbamoyl group, a pyrimidin-5-ylcarbamoyl group, a pyridazin-3-ylcarbamoyl group, a pyridazin-4-ylcarbamoyl group, a 2H-pyrazol-3-ylcarbamoyl group, a 1H-pyrazol-4-ylcarbamoyl group, a 1H-pyrazolyl-3-carbamoyl group, a pyrazin-3-ylcarbamoyl group, a pyrazin-4-ylcarbamoyl group, a quinolin-2-ylcarbamoyl group, a quinolin-3-ylcarbamoyl group, a quinolin-4-ylcarbamoyl group, an isoquinolin-1-ylcarbamoyl group, an isoquinolin-3-ylcarbamoyl group, an isoquinolin-4-ylcarbamoyl group, a quinazolin-2-ylcarbamoyl group, a quinazolin-3-ylcarbamoyl group, a quinoxalin-2-ylcarbamoyl group, a quinoxalin-3-ylcarbamoyl group, a cinnolin-3-ylcarbamoyl group, a cinnolin-4-ylcarbamoyl group, a 1H-benzimidazol-2-ylcarbamoyl group, a 1H-imidazo[4,5-b]pyridin-5-ylcarbamoyl group, a 1H-imidazo[4,5-b]pyridin-6-ylcarbamoyl group, a 1H-imidazo[4,5-b]pyridin-7-ylcarbamoyl group, a benzo[d]isoxazol-4-ylcarbamoyl group, a benzo[d]isoxazol-5-ylcarbamoyl group, a benzo[d]isoxazol-6-ylcarbamoyl group, a benzoxazol-4-ylcarbamoyl group, a benzoxazol-5-ylcarbamoyl group, a benzoxazol-6-ylcarbamoyl group.

"Arylalkylcarbamoyl group" means a carbamoyl group with the above-mentioned, one or two "aralkyl groups" bonding thereto, including, for example, a benzylcarbamoyl group, a 1-phenylethylcarbamoyl group, a 2-phenylethylcarbamoyl group, a 1-naphthylmethylcarbamoyl group, a 2-naphthylmethylcarbamoyl group.

"Heteroarylalkylcarbamoyl group" means a carbamoyl group with the above-mentioned, one or two "heteroarylalkyl groups" bonding thereto, including, for example, a furan-3-yl-methylcarbamoyl group, a furan-2-ylmethylcarbamoyl group, a furan-3-ylethylcarbamoyl group, a furan-2-ylethylcarbamoyl group, a furan-3-ylpropylcarbamoyl group, a furan-2-ylpropylcarbamoyl group, a thiophen-3-ylmethylcarbamoyl group, a thiophen-2-ylmethylcarbamoyl group, a thiophen-3-ylethylcarbamoyl group, a thiophen-2-ylethylcarbamoyl group, a thiophen-3-ylpropylcarbamoyl group, a thiophen-2-ylpropylcarbamoyl group, a 1H-pyrrol-3-ylmethylcarbamoyl group, a 1H-pyrrol-2-ylmethylcarbamoyl group, a 1H-pyrrol-3-ylethylcarbamoyl group, a 1H-pyrrol-2-ylethylcarbamoyl group, a 1H-pyrrol-3-ylpropylcarbamoyl group, a 1H-pyrrol-2-ylpropylcarbamoyl group, a 1H-imidazol-4-ylmethylcarbamoyl group, a 1H-imidazol-2-ylmethylcarbamoyl group, a 1H-imidazol-5-ylmethylcarbamoyl group, a 1H-imidazol-4-ylethylcarbamoyl group, a 1H-imidazol-2-ylethylcarbamoyl group, a 1H-imidazol-5-ylethylcarbamoyl group, a 1H-imidazol-4-ylpropylcarbamoyl group, a 1H-imidazol-2-ylpropylcarbamoyl group, a 1H-imidazol-5-ylpropylcarbamoyl group, a 1H-[1,2,3]triazol-4-ylmethylcarbamoyl group, a 1H-[1,2,3]triazol-5-ylmethylcarbamoyl group, a 1H-[1,2,3]triazol-4-ylethylcarbamoyl group, a 1H-[1,2,3]triazol-5-ylethylcarbamoyl group, a 1H-[1,2,3]triazol-4-ylpropylcarbamoyl group, a 1H-[1,2,3]triazol-5-ylpropylcarbamoyl group, a 1H-[1,2,4]triazol-3-yl-methylcarbamoyl group, a 1H-[1,2,4]triazol-5-ylmethylcarbamoyl group, a 1H-[1,2,4]triazol-3-ylethylcarbamoyl group, a 1H-[1,2,4]triazol-5-ylethylcarbamoyl group, a 1H-[1,2,4]triazol-3-ylpropylcarbamoyl group, a 1H-[1,2,4]triazol-5-ylpropylcarbamoyl group, a thiazol-4-ylmethylcarbamoyl group, a thiazol-3-ylmethylcarbamoyl group, a thiazol-2-ylmethylcarbamoyl group, a thiazol-4-ylethylcarbamoyl group, a thiazol-3-ylethylcarbamoyl group, a thiazol-2-ylethylcarbamoyl group, a thiazol-4-ylpropylcarbamoyl group, a thiazol-3-ylpropylcarbamoyl group, a thiazol-2-ylpropylcarbamoyl group, a [1,2,4]thiadiazol-3-ylmethylcarbamoyl group, a [1,2,4]thiadiazol-3-ylethylcarbamoyl group, a [1,2,4]thiadiazol-3-ylpropylcarbamoyl group, a [1,2,4]thiadiazol-5-ylmethylcarbamoyl group, a [1,2,4]thiadiazol-5-ylethylcarbamoyl group, a [1,2,4]thiadiazol-5-ylpropylcarbamoyl group, a [1,3,4]thiadiazol-2-2-ylmethylcarbamoyl group, a [1,3,4]thiadiazol-2-ylethylcarbamoyl group, a [1,3,4]thiadiazol-2-ylpropylcarbamoyl group.

"Aryloxycarbonylamino group" means a group of the above-mentioned "aryloxy group" with a carbonyl group bonding thereto, including, for example, a phenoxycarbonylamino group, a 1-phenylethyloxycarbonylamino group, a naphthalene-2-ylethyloxycarbonylamino group, a naphthalene-1-ylmethyloxycarbonylamino group, a 2-naphthylmethyloxycarbonylamino group.

"Arylalkyloxycarbonylamino group" means a group of the above-mentioned "aralkyloxy group" with a carbonylamino group bonding thereto, including, for example, a benzyloxycarbonylamino group, a 1-phenylethyloxycarbonylamino group, a 2-phenylethyloxycarbonylamino group, a 1-naphthylmethyloxycarbonylamino group, a 2-naphthylmethyloxycarbonylamino group.

"Lower alkyloxycarbonylamino group" means a group of the above-mentioned "alkoxy group" with a carbonylamino group bonding thereto, including, for example, a methoxycarbonylamino group, an ethoxycarbonylamino group, a propoxycarbonylamino group.

"Lower alkylcarbonylamino group" means a group of the above-mentioned "lower alkyl group" with a carbonylamino group bonding thereto, including, for example, a methylcarbonylamino group, an ethylcarbonylamino group, a propylcarbonylamino group, an isopropylcarbonylamino group, an isobutylcarbonylamino group.

"Arylcarbonylamino group" means a group of the above-mentioned "aryl group" with a carbonylamino group bonding thereto, including, for example, a phenylcarbonylamino group, a naphthalene-1-ylcarbonylamino group, a naphthalene-2-ylcarbonylamino group.

"Heteroarylcarbonylamino group" means a group of the above-mentioned "heteroaryl group" with a carbonylamino group bonding thereto, including, for example, a furan-2-ylcarbonylamino group, a furan-3-ylcarbonylamino group, a thiophen-2-ylcarbonylamino group, a thiophene-3-ylcarbonylamino group, a 1H-pyrrol-2-ylcarbonylamino group, a 1H-pyrrol-3-ylcarbonylamino group, a 1H-imidazol-2-ylcarbonylamino group, a 1H-imidazol-4-ylcarbonylamino group, a 3H-imidazol-4-ylcarbonylamino group, a 4H-[1,3,4]triazol-3-ylcarbonylamino group, a 2H-[1,2,4]triazol-3-ylcarbonylamino group, a 1H-[1,2,4]triazol-3-ylcarbonylamino group, a thiazol-2-ylcarbonylamino group, a thiazol-4-ylcarbonylamino group, a thiazol-5-ylcarbonylamino group, a pyridin-2-ylcarbonylamino group, a pyridin-3-ylcarbonylamino group, a pyridin-4-ylcarbonylamino group, a pyrimidin-2-ylcarbonylamino group, a pyrimidin-4-ylcarbonylamino group, a pyrimidin-5-ylcarbonylamino group, a pyridazin-3-ylcarbonylamino group, a pyridazin-4-ylcarbonylamino group, a 2H-pyrazol-3-ylcarbonylamino group, a 1H-pyrazol-4-ylcarbonylamino group, a 1H-pyrazolyl-3-carbonylamino group, a pyrazin-3-ylcarbonylamino group, a pyrazin-4-ylcarbonylamino group, a quinolin-2-ylcarbonylamino group, a quinolin-3-ylcarbonylamino group, a quinolin-4-ylcarbonylamino group, an isoquinolin-1-ylcarbonylamino group, an isoquinolin-3-ylcarbonylamino group, an isoquinolin-4-ylcarbonylamino group, a quinazolin-2-ylcarbonylamino group, a quinazolin-3-ylcarbonylamino group, a quinoxalin-2-ylcarbonylamino group, a quinoxalin-3-ylcarbonylamino group, a cinnolin-3-ylcarbonylamino group, a cinnolin-4-ylcarbonylamino group, a 1H-benzimidazol-2-ylcarbonylamino group, a 1H-imidazo[4,5-b]pyridin-5-ylcarbonylamino group, a 1H-imidazo[4,5-b]pyridin-6-ylcarbonylamino group, a 1H-imidazo[4,5-b]pyridin-7-ylcarbonylamino group, a benzo[d]isoxazol-4-ylcarbonylamino group, a benzo[d]isoxazol-5-ylcarbonylamino group, a benzo[d]isoxazol-6-ylcarbonylamino group, a benzoxazol-4-ylcarbonylamino group, a benzoxazol-5-ylcarbonylamino group, a benzoxazol-6-yloxy group.

"Arylcarbonyl group" means a group of the above-mentioned "aryl group" with a carbonyl group bonding thereto, including, for example, a phenylcarbonyl group, a naphthalene-1-ylcarbonyl group, a naphthalene-2-ylcarbonyl group.

"Arylalkylcarbonyl group" means a group of the above-mentioned "aralkyl group" with a carbonyl group bonding thereto, including, for example, a phenylmethylcarbonyl group, a naphthalene-1-ylcarbonyl group, a naphthalene-2-ylcarbonyl group.

"Arylsulfonylamino group" means a group of the above-mentioned "aryl group" with a sulfonylamino group bonding thereto, including, for example, a phenylsulfonylamino group, a naphthalene-1-ylsulfonylamino group, a naphthalene-2-ylsulfonylamino group.

"Alkylaminosulfonyl group" means a group of the above-mentioned "alkylamino group" with a sulfonyl group bonding thereto, including, for example, a methylaminosulfonyl group, an ethylaminosulfonyl group, a propylaminosulfonyl group, an isopropylaminosulfonyl group, a butylamino group, a sec-butylamino group, a tert-butylamino group.

"Arylaminosulfonyl group" means a group of the above-mentioned "aryl group" with an aminosulfonyl group bonding thereto, including, for example, a phenylaminosulfonyl group, a naphthalene-1-ylaminosulfonyl group, a naphthalene-2-ylaminosulfonyl group.

The compounds of formula (I) of the invention are disclosed more concretely.

For further more concretely disclosing the compounds of formula (I) of the invention, the symbols used in the formula (I):

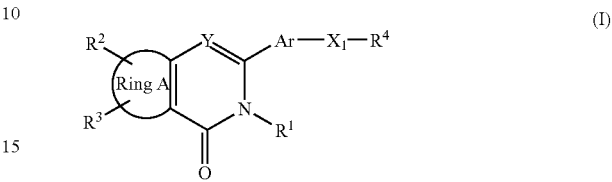

[wherein the symbols have the same meanings as above] are described below.

$R^1$ represents an aryl group, a 5- or 6-membered heteroaryl group having, in the ring, from 1 to 4 hetero atoms selected from a group consisting of a nitrogen atom, a sulfur atom and an oxygen atom, a heteroarylalkyl group, a linear or branched lower alkyl group (the lower alkyl group may be substituted with a hydroxyl group, a halogen atom or an alkoxy group), an aralkyl group, an alkoxy group, an alkoxycarbonyl group or an alkanoyl group (the aryl group, the heteroaryl group, the heteroarylalkyl group or the aralkyl group may be substituted with a hydroxyl group, a halogen atom or an alkoxy group).

"Aryl group" for $R^1$ is preferably a phenyl group of those exemplified hereinabove for the above-defined aryl group.

"5- or 6-Membered heteroaryl group" for $R^1$ includes, for example, a furyl group, a thienyl group, a pyrrolyl group, an imidazolyl group, a triazolyl group, a thiazolyl group, a thiadiazolyl group, an isothiazolyl group, an oxazolyl group, an isoxazolyl group, a pyridyl group, a pyrimidinyl group, a pyridazinyl group, a pyrazolyl group, a pyrazinyl group, a quinolinyl group, an isoquinolinyl group, a quinazolinyl group, a quinolidinyl group, a quinoxalinyl group, a cinnolinyl group, a benzimidazolyl group, an imidazopyridyl group, a benzofuranyl group, a naphthyridinyl group, a 1,2-benzisoxazolyl group, a benzoxazolyl group, a benzothiazolyl group, an oxazolopyridyl group, a pyridothiazolyl group, an isothiazolopyridyl group, a benzothienyl group.

Of those, the "5- or 6-membered heteroaryl group" is preferably a furyl group, a thienyl group, a pyrrolyl group, a triazolyl group, a thiazolyl group, an isothiazolyl group, a pyridyl group, a pyrimidinyl group, a pyridazinyl group, a pyrazolyl group or a pyrazinyl group, which may be substituted with a lower alkyl group, a halogen atom or an alkoxy group; more preferably, a thienyl group, a pyrrolyl group, a thiazolyl group, a pyridyl group, a pyrimidinyl group, a pyridazinyl group, a pyrazolyl group or a pyrazinyl group, which may be substituted with a lower alkyl group, a halogen atom or an alkoxy group.

"Heteroarylalkyl group" for $R^1$ includes a furan-3-ylmethyl group, a furan-2-ylmethyl group, a furan-3-ylethyl group, a furan-2-ylethyl group, a furan-3-ylpropyl group, a furan-2-ylpropyl group, a thiophen-3-ylmethyl group, a thiophen-2-ylmethyl group, a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-pyrrol-2-ylpropyl group, a 1H-imidazol-4-ylmethyl group, a 1H-imidazol-2-ylmethyl group, a 1H-imidazol-5- ylmethyl group, a 1H-imidazol-4-ylethyl group, a 1H-imidazol-2-ylethyl group, a 1H-imidazol-5-ylethyl group, a 1H-imidazol-4-ylpropyl group, a 1H-imidazol-2-ylpropyl group, a 1H-imidazol-5-ylpropyl group, a 1H-[1,2,3]triazol-4-ylmethyl group, a 1H-[1,2,3]triazol-5-ylmethyl group, a 1H-[1,2,3]triazol-4-ylethyl group, a 1H-[1,2,3]triazol-5-ylethyl group, a 1H-[1,2,3]triazol-4-ylpropyl group, a 1H-[1,2,3]triazol-5-ylpropyl group, a 1H-[1,2,4]triazol-3-ylmethyl group, a 1H-[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group, a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group, a thiazol-4-ylpropyl group, a thiazol-3-ylpropyl group, a thiazol-2-ylpropyl group, a [1,2,4]thiadiazol-3-ylmethyl group, a [1,2,4]thiadiazol-3-ylethyl group, a [1,2,4]thiadiazol-3-ylpropyl group, a [1,2,4]thiadiazol-5-ylmethyl group, a [1,2,4]thiadiazol-5-ylethyl group, a [1,2,4]thiadiazol-5-ylpropyl group, a [1,3,4]thiadiazol-2-2-ylmethyl group, a [1,3,4]thiadiazol-2-ylethyl group, a [1,3,4]thiadiazol-2-ylpropyl group. Of those, preferred are a thiophen-3-ylethyl group, a thiophen-2-ylethyl group, a thiophen-3-ylpropyl group, a thiophen-2-ylpropyl group, a 1H-pyrrol-3-ylmethyl group, a 1H-pyrrol-2-ylmethyl group, a 1H-pyrrol-3-ylethyl group, a 1H-pyrrol-2-ylethyl group, a 1H-pyrrol-3-ylpropyl group, a 1H-[1,2,4]triazol-3-ylmethyl group, a 1H-[1,2,4]triazol-5-ylmethyl group, a 1H-[1,2,4]triazol-3-ylethyl group, a 1H-[1,2,4]triazol-5-ylethyl group, a 1H-[1,2,4]triazol-3-ylpropyl group, a 1H-[1,2,4]triazol-5-ylpropyl group, a thiazol-4-ylmethyl group, a thiazol-3-ylmethyl group, a thiazol-2-ylmethyl group, a thiazol-4-ylethyl group, a thiazol-3-ylethyl group, a thiazol-2-ylethyl group.

"Linear or branched lower alkyl group" for $R^1$ is preferably the above-defined, linear or branched alkyl group having from 1 to 6 carbon atoms, for example, preferably a methyl group, an ethyl group, an n-propyl group, an isopropyl group, an n-butyl group.

The "linear or branched lower alkyl group" may be substituted with a hydroxyl group, a halogen atom or an alkoxy group.

Halogen atom for the substituent includes, for example, a fluorine atom, a chlorine atom, a bromine atom.

Alkoxy group for the substituent includes, for example, a methoxy group, an ethoxy group, an isopropoxy group.

From the above, "linear or branched lower alkyl group" optionally substituted with a hydroxyl group, a halogen atom or an alkoxy group is, for example, preferably a methyl group, a trifluoromethyl group, a difluoromethyl group, a fluoromethyl group, a hydroxymethyl group, a methoxymethyl group, an ethoxymethyl group, an ethyl group, a 2,2,2-trifluoroethyl group, a 2,2-difluoroethyl group, a 2-fluoroethyl group, a hydroxyethyl group, a 2-methoxyethyl group, a 2-ethoxyethyl group, an n-propyl group, a 3-fluoropropyl group, an isopropyl group; more preferably a methyl group, an ethyl group, an n-propyl group.

"Aralkyl group" for $R^1$ is preferably a benzyl group optionally substituted with a lower alkyl group or a lower alkoxy group, of those exemplified hereinabove for the above-defined aralkyl group.

"Alkoxy group" for $R^1$ is, for example, preferably a methoxy group, an ethoxy group, an n-propyloxy group or an isopropyloxy group of those exemplified hereinabove for the above-defined alkoxy group.

More preferably, $R^1$ is an aryl group, a 5- or 6-membered heteroaryl group having, in the ring, from 1 to 3 hetero atoms selected from a group consisting of a nitrogen atom, a sulfur atom and an oxygen atom, a linear or branched lower alkyl group (the lower alkyl group may be substituted with a hydroxyl group, a halogen atom or an alkoxy group), an aralkyl group or an alkoxy group; even more preferably an aryl group, a 5- or 6-membered heteroaryl group having, in the ring, from 1 to 3 hetero atoms selected from a group consisting of a nitrogen atom, a sulfur atom and an oxygen atom, a linear or branched lower alkyl group (the lower alkyl group may be substituted with a hydroxyl group, a halogen atom or an alkoxy group) or an aralkyl group; further more preferably a lower alkyl group (the lower alkyl group may be substituted with a hydroxyl group, a halogen atom or an alkoxy group).

$R^4$ represents a group of a formula (II):

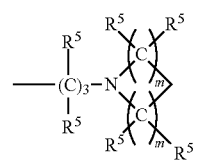

(II)

[wherein the symbols have the same meanings as above], or a group of a formula J (III):

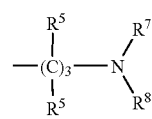

(III)

[wherein the symbols have the same meanings as above], or a group of a formula (IV):

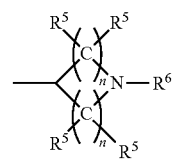

(IV)

[wherein the symbols have the same meanings as above], or a group of a formula (V):

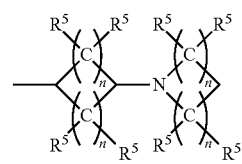

(V)

[wherein the symbols have the same meanings as above].

Formula (II) is described below.

$R^5$ each independently represents a hydrogen atom, a lower alkyl group, a hydroxyl group, a halogen atom.

"Lower alkyl group" for $R^5$ includes, for example, a methyl group, an ethyl group, an isopropyl group.

"Halogen atom" for $R^5$ includes, for example, a fluorine atom, a chlorine atom, a bromine atom.

m indicates an integer of from 0 to 4. When m is 0, then a formula (II-1):

(II-1)

in formula (II) means a single bond.

From the above, the group of formula (II) concretely includes, for example, a 3-(1-azetidinyl)-propyl group, a 3-(1-pyrrolidinyl)-propyl group, a 3-(2-methylpyrrolidinyl-1-yl)-propyl group, a 3-(3-methylpyrrolidinyl-1-yl)-propyl group, a 3-(2,5-dimethylpyrrolidin-1-yl)-propyl group, a 3-(3,4-dimethylpyrrolidin-1-yl)-propyl group, a 3-(1-piperidinyl)-propyl group, a 3-(2-methylpiperidin-1-yl)-propyl group, a 3-(3-methylpiperidin-1-yl)-propyl group, a 3-(4-methylpiperidin-1-yl)-propyl group, a 3-(2,6-dimethylpiperidin-1-yl)-propyl group, a 3-(3,5-dimethylpiperidin-1-yl)-propyl group, a 3-(1-homopiperidinyl)-propyl group, a 3-(1-azocanyl)-propyl group.

Next described is formula (III).

$R^5$ each independently represents a hydrogen atom, a lower alkyl group, a hydroxyl group, a halogen atom.

"Lower alkyl group" for $R^5$ includes, for example, a methyl group, an ethyl group, an isopropyl group.

"Halogen atom" for $R^5$ includes, for example, a fluorine atom, a chlorine atom, a bromine atom.

$R^7$ and $R^8$ each independently represent a lower alkyl group, an aralkyl group, a heteroarylalkyl group.

"Lower alkyl group" for $R^7$ and $R^8$ includes, for example, a methyl group, an ethyl group, an isopropyl group.

"Aralkyl group" for $R^7$ and $R^8$ is, for example, a benzyl group.

"Heteroarylalkyl group" for $R^7$ and $R^8$ includes, for example, a pyridin-2-ylmethyl group, a pyridin-3-ylmethyl group, a pyridin-4-ylmethyl group.

From the above, the group of formula (III) concretely includes, for example, a 3-(methyl-phenyl-amino)-propyl group, a 3-(isopropyl-phenyl-amino)propyl group, a 3-(benzyl-phenyl-amino)-propyl group, a 3-(ethyl-phenyl-amino)-propyl group, a 3-(isopropyl-phenyl-amino)-propyl group.

Next described is formula (IV).

$R^5$ each independently represents a hydrogen atom, a lower alkyl group, a hydroxyl group, a halogen atom.

"Lower alkyl group" for $R^5$ includes, for example, a methyl group, an ethyl group, an isopropyl group.

"Halogen atom" for $R^5$ includes, for example, a fluorine atom, a chlorine atom, a bromine atom.

$R^6$ represents a linear or branched lower alkyl group or a cycloalkyl group.

"Linear or branched lower alkyl group" for $R^6$ includes, for example, a methyl group, an ethyl group, an isopropyl group.

"Cycloalkyl group" for $R^5$ has the same meaning as that of the above-defined cycloalkyl group, including, for example, a cyclopropyl group, a cyclobutyl group, a cyclopentyl group, a cyclohexyl group, a cycloheptyl group.

One or two methylene groups constituting the cycloalkyl group may be substituted with a nitrogen atom, an oxygen atom or a sulfur atom.

In case where two methylene groups in the cycloalkyl group are substituted with any of a nitrogen atom, an oxygen atom or a sulfur atom, then these may be the same or different.

Cases where one or two methylene groups in the cycloalkyl group are substituted with a nitrogen atom, an oxygen atom or a sulfur atom concretely include, for example, a morpholinyl group, a thiomorpholinyl group, a piperidinyl group, a pyrimidinyl group, a pyrazinyl group.

n indicates from 0 to 4, but n's must not be 0 at the same time.

From the above, the group of formula (IV) includes, for example, a 1-methyl-4-piperidinyl group, a 1-ethyl-4-piperidinyl group, a 1-propyl-4-piperidinyl group, a 1-isopropyl-4-piperidinyl group, a 1-cyclopropyl-4-piperidinyl group, a 1-cyclobutyl-4-piperidinyl group, a 1-cyclopentyl-4-piperidinyl group, a 1-cyclohexyl-4-piperidinyl group, a 1-cycloheptyl-4-piperidinyl group, a 1-methyl-3-pyrrolidinyl group, a 1-ethyl-3-pyrrolidinyl group, a 1-propyl-3-pyrrolidinyl group, a 1-isopropyl-3-pyrrolidinyl group, a 1-cyclopropyl-3-pyrrolidinyl group, a 1-cyclobutyl-3-pyrrolidinyl group, a 1-cyclopentyl-3-pyrrolidinyl group, a 1-cyclohexyl-3-pyrrolidinyl group, a 1-cycloheptyl-3-pyrrolidinyl group, a 1-methyl-4-azepanyl group, a 1-ethyl-4-azepanyl group, a 1-propyl-4-azepanyl group, a 1-isopropyl-4-azepanyl group, a 1-cyclopropyl-4-azepanyl group, a 1-cyclobutyl-4-azepanyl group, a 1-cyclopentyl-4-azepanyl group, a 1-cyclohexyl-4-azepanyl group, a 1-cycloheptyl-4-azepanyl group, a 1-methyl-4-azocanyl group, a 1-ethyl-4-azocanyl group, a 1-propyl-4-azocanyl group, a 1-isopropyl-4-azocanyl group, a 1-cyclopropyl-4-azocanyl group, a 1-cyclobutyl-4-azocanyl group, a 1-cyclopentyl-4-azocanyl group, a 1-cyclohexyl-4-azocanyl group, a 1-cycloheptyl-4-azocanyl group, a 4-{1-(3-oxetanyl)}piperidinyl group, a 4-(1-tetrahydro-2H-pyran-4-yl)piperidinyl group, a 4-(1-tetrahydro-2H-thiopyran-4-yl)piperidinyl group, a 4-[1-(1,4-dioxan-2-yl)]piperidinyl group, a 4-[1-(1-methyl-3-pyrrolidinyl)]piperidinyl group, a 4-(1-tetrahydro-3-furanyl)piperidinyl group, a 4-(1-tetrahydro-3-thiofuranyl)piperidinyl group, a 4-{1-(2-methylcyclopentyl)}piperidinyl group, a 4-{1-(3-methylcyclopentyl)}piperidinyl group, a 4-{1-(2-cyclopenten-1-yl)}piperidinyl group, a 3-{1-(3-oxetanyl)}pyrrolidinyl group, a 3-(1-tetrahydro-2H-pyran-4-yl)pyrrolidinyl group, a 3-(1-tetrahydro-2H-thiopyran-4-yl)pyrrolidinyl group, a 3-[1-(1,4-dioxan-2-yl)]pyrrolidinyl group, a 3-[1-(1-methyl-3-pyrrolidinyl)]pyrrolidinyl group, a 3-(1-tetrahydro-3-furanyl)pyrrolidinyl group, a 3-(1-tetrahydro-3-thiofuranyl)pyrrolidinyl group, a 3-{1-(2-methylcyclopentyl)}pyrrolidinyl group, a 3-{1-(3-methylcyclopentyl)}pyrrolidinyl group, a 3-{1-(2-cyclopenten-1-yl)}pyrrolidinyl group, a 4-{1-(3-oxetanyl)}azepanyl group, a 4-(1-tetrahydro-2H-pyran-4-yl)azepanyl group, a 4-(1-tetrahydro-2H-thiopyran-4-yl)azepanyl group, a 4-[1-(1,4-dioxan-2-yl)]azepanyl group, a 4-[1-(1-methyl-3-pyrrolidinyl)]azepanyl group, a 4-(1-tetrahydro-3-furanyl)azepanyl group, a 4-(1-tetrahydro-3-thiofuranyl)azepanyl group, a 4-{1-(2-methylcyclopentyl)}azepanyl group, a 4-{1-(3-methylcyclopentyl)}azepanyl group, a 4-{1-(2-cyclopenten-1-yl)}azepanyl group, a 5-{1-(3-oxetanyl)}azocanyl group, a 5-(1-tetrahydro-2H-pyran-4-yl)azocanyl group, a 5-(1-tetrahydro-2H-thiopyran-4-yl)azocanyl group, a 5-[1-(1,4-dioxan-2-yl)]azocanyl group, a 5-[1-(1-methyl-3-pyrrolidinyl)]azocanyl group, a 5-(1-tetrahydro-3-furanyl)azocanyl group, a 5-(1-tetrahydro-3-thiofuranyl)azocanyl group, a 5-{1-(2-methylcyclopentyl)}azocanyl group, a 5-{1-(3-methylcyclopentyl)}azocanyl group, a 5-{1-(2-cyclopenten-1-yl)}azocanyl group, a 1-methyl-3-piperidinyl group, a 1-ethyl-3-piperidinyl group, a 1-propyl-3-piperidinyl group, a 1-(2-propyl)-3-piperidinyl group, a 1-cyclopropyl-3-piperidinyl group, a 1-cyclobutyl-3-piperidinyl group, a 1-cyclopentyl-3-piperidinyl group, a 1-cyclohexyl-3-piperidinyl group, a 1-cycloheptyl-3-piperidinyl group, a 1-methyl-4-azocanyl group, a 1-ethyl-4-azocanyl group, a 1-propyl-4-azocanyl group, a 1-(2-propyl)-4-azocanyl group, a 1-cyclopropyl-4-azocanyl group, a 1-cyclobutyl-4-azocanyl group, a 1-cyclopentyl-4-azocanyl group, a 1-cyclohexyl-4-azocanyl group, a 1-cycloheptyl-4-azocanyl group, a 5-{1-(3-oxetanyl)}piperidinyl group, a 5-(1-tetrahydro-2H-pyran-4-yl)piperidinyl group, a 5-(1-tetrahydro-2H-thiopyran-4-yl)piperidinyl group, a 5-[1-(1,4-dioxan-2-yl)]piperidinyl group, a 5-[1-(1-methyl-3-pyrrolidinyl)]piperidinyl group, a 5-(1-tetrahydro-3-furanyl)piperidinyl group, a 5-(1-tetrahydro-3-thiofuranyl)piperidinyl group, a 5-{1-(2-methylcyclopentyl)}piperidinyl group, a 5-{1-(2,5-dimethylcyclopentyl)}piperidinyl group, a 5-{1-(3-methylcyclopentyl)}piperidinyl group, a 5-{1-(2-cyclopenten-1-yl)}piperidinyl group, a 5-(2-methyl)-1,2-oxazinyl group, a 5-(2-methyl)-1,2-thiazinyl group, a 5-(2-ethyl)-1,2-oxazinyl group, a 5-(2-ethyl)-1,2-thiazinyl group, a 5-(2-cyclopropyl)-1,2-oxazinyl group, a 5-(2-cyclopropyl)-1,2-thiazinyl group, a 5-(2-cyclobutyl)-1,2-oxazinyl group, a 5-(2-cyclobutyl)-1,2-thiazinyl group, a 5-(2-cyclopentyl)-1,2-oxazinyl group, a 5-(2-cyclopentyl)-1,2-thiazinyl group, a 5-(2-cyclohexyl)-1,2-oxazinyl group, a 5-(2-cyclohexyl)-1,2-thiazinyl group, a 5-(2-cycloheptyl)-1,2-oxazinyl group, a 5-(2-cycloheptyl)-1,2-thiazinyl group, a 4-(2-methyl)-tetrahydroisoxazolyl group, a 4-(2-ethyl)-tetrahydroisoxazolyl group, a 4-(2-propyl)tetrahydroisoxazolyl group, a 4-(2-cyclopropyl)-tetrahydroisoxazolyl group, a 4-(2-cyclobutyl)-tetrahydroisoxazolyl group, a 4-(2-cyclopentyl)-tetrahydroisoxazolyl group, a 4-(2-cyclohexyl)-tetrahydroisoxazolyl group, a 4-(2-cycloheptyl)-tetrahydroisoxazolyl group. Of those, preferred are a 1-isopropyl-4-piperidinyl group, a 1-cyclopropyl-4-piperidinyl group, a 1-cyclobutyl-4-piperidinyl group, a 1-cyclopentyl-4-piperidinyl group, a 1-cyclohexyl-4-piperidinyl group, a 1-cycloheptyl-4-piperidinyl group, a 1-isopropyl-4-pyrrolidinyl group, a 1-cyclopropyl-3-pyrrolidinyl group, a 1-cyclobutyl-3-pyrrolidinyl group, a 1-cyclopentyl-3-pyrrolidinyl group, a 1-cyclohexyl-3-pyrrolidinyl group, a 1-cycloheptyl-3-pyrrolidinyl group, a 1-isopropyl-4-azepanyl group, a 1-cyclopropyl-4-azepanyl group, a 1-cyclobutyl-4-azepanyl group, a 1-cyclopentyl-4-azepanyl group, a 1-cyclohexyl-4-azepanyl group, a 1-cycloheptyl-4-azepanyl group, a 4-{1-(2-methylcyclopentyl)}piperidinyl group, a 4-{1-(3-methylcyclopentyl)}piperidinyl group, a 5-(2-methyl)-1,2-oxazinyl group, a 5-(2-methyl)-1,2-thiazinyl group, a 5-(2-ethyl)-1,2-oxazinyl group, a 5-(2-ethyl)-1,2-thiazinyl group, a 5-(2-cyclopropyl)-1,2-oxazinyl group, a 5-(2-cyclopropyl)-1,2-thiazinyl group, a 5-(2-cyclobutyl)-1,2-oxazinyl group, a 5-(2-cyclobutyl)-1,2-thiazinyl group, a 5-(2-cyclohexyl)-1,2-oxazinyl group, a 5-(2-cyclohexyl)-1,2-thiazinyl group, a 4-(2-methyl)-tetrahydroisoxazolyl group, a 4-(2-ethyl)-tetrahydroisoxazolyl group, a 4-(2-propyl)-tetrahydroisoxazolyl group, a 4-(2-cyclopropyl)-tetrahydroisoxazolyl group, a 4-(2-cyclobutyl)-tetrahydroisoxazolyl group, a 4-(2-cyclopropyl)-tetrahydroisoxazolyl group; and more preferred are a 1-isopropyl-4-piperidinyl group, a 1-cyclopropyl-4-piperidinyl group, a 1-cyclobutyl-4-piperidinyl group, a 1-cyclopentyl-4-piperidinyl group, a 1-cyclohexyl-4-piperidinyl group, a 1-cycloheptyl-4-piperidinyl group, a 4-{1-(2-methylcyclopentyl)}piperidinyl group, a 4-{1-(3-methylcyclopentyl)}piperidinyl group, a 1-isopropyl-3-pyrrolidinyl group, a 1-cyclopropyl-3-pyrrolidinyl group, a 1-cyclobutyl-3-pyrrolidinyl group, a 1-cyclopentyl-3-pyrrolidinyl group, a 1-cyclohexyl-3-pyrrolidinyl group, a 1-cycloheptyl-3-pyrrolidinyl group, a 1-cyclopropyl-4-azepanyl group, a 1-cyclobutyl-4-azepanyl group, or a 1-cyclopentyl-4-azepanyl group.

Formula (V):

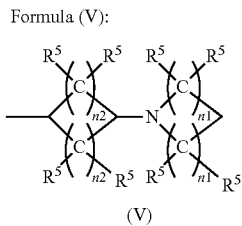

(V)

is described.

$R^5$ each independently represents a hydrogen atom, a lower alkyl group, a hydroxyl group or a halogen atom.

n1 each independently indicates from 0 to 4. (However, n1's must not be 0 at the same time.)

n2 each independently indicates from 0 to 4. (However, n2's must not be 0 at the same time.)

From the above, the group of formula (V) includes, for example, a 1-cyclopropyl-azetan-2-yl group, a 1-cyclobutyl-azetan-3-yl group, a 1-cyclobutyl-azetan-2-yl group, a 1-cyclopentyl-azetan-3-yl group, a 1-cyclopentyl-azetan-2-yl group, a 1-cyclohexyl-azetan-4-yl group, a 1-cyclohexyl-azetan-3-yl group, a 1-cyclohexyl-azetan-2-yl group, a 1-cycloheptyl-azetan-4-yl group, a 1-cycloheptyl-azetan-3-yl group, a 1-cycloheptyl-azetan-2-yl group, a 1-cyclopropyl-piperidin-2-yl group, a 1-cyclobutyl-piperidin-3-yl group, a 1-cyclobutyl-piperidin-2-yl group, a 1-cyclopentyl-piperidin-3-yl group, a 1-cyclopentyl-piperidin-2-yl group, a 1-cyclohexyl-piperidin-4-yl group, a 1-cyclohexyl-piperidin-3-yl group, a 1-cyclohexyl-piperidin-2-yl group, a 1-cycloheptyl-piperidin-4-yl group, a 1-cycloheptyl-piperidin-3-yl group, a 1-cycloheptyl-piperidin-2-yl group, a 1-cyclopropyl-pyrrolidin-2-yl group, a 1-cyclobutyl-pyrrolidin-3-yl group, a 1-cyclobutyl-pyrrolidin-2-yl group, a 1-cyclopentyl-pyrrolidin-3-yl group, a 1-cyclopentyl-pyrrolidin-2-yl group, a 1-cyclohexyl-pyrrolidin-4-yl group, a 1-cyclohexyl-pyrrolidin-3-yl group, a 1-cyclohexyl-pyrrolidin-2-yl group, a 1-cycloheptyl-pyrrolidin-3-yl group, a 1-cycloheptyl-pyrrolidin-2-yl group, a 1-cycloheptyl-pyrrolidin-4-yl group, a 1-cyclopropyl-hexamethyleneiminyl-2-yl group, a 1-cyclobutyl-hexamethyleneiminyl-3-yl group, a 1-cyclobutyl-hexamethyleneiminyl-2-yl group, a 1-cyclopentyl-hexamethyleneiminyl-3-yl group, a 1-cyclopentyl-hexamethyleneiminyl-2-yl group, a 1-cyclohexyl-hexamethyleneiminyl-4-yl group, a 1-cyclohexyl-hexamethyleneiminyl-3-yl group, a 1-cyclohexyl-hexamethyleneiminyl-2-yl group, a 1-cycloheptyl-hexamethyleneiminyl-4-yl group, a 1-cycloheptyl-hexamethyleneiminyl-3-yl group, a 1-cycloheptyl-hexamethyleneiminyl-2-yl group; preferably a 1-cyclobutyl-azetan-3-yl group, a 1-cyclopentyl-azetan-3-yl group, a 1-cyclohexyl-azetan-4-yl group, a 1-cycloheptyl-azetan-4-yl group, a 1-cyclopentyl-piperidin-3-yl group, a 1-cyclohexyl-piperidin-4-yl group, a 1-cycloheptyl-piperidin-4-yl group, a 1-cyclobutyl-pyrrolidin-3-yl group, a 1-cyclopentyl-pyrrolidin-3-yl group, a 1-cyclohexyl-pyrrolidin-4-yl group, a 1-cycloheptyl-pyrrolidin-4-yl group.

Of the above-mentioned formulae (II) to (V), preferred are formulae (II), (IV) and (V); more preferred are formulae (II) and (IV); and even more preferred is formula (IV).

$X_1$ represents NH, an oxygen atom or a sulfur atom.

$X_1$ is preferably an oxygen atom or sulfur atom, more preferably an oxygen atom.

Ar is an aryl group or a heteroaryl group, which may have 1 or 2 substituents of a lower alkyl group, an alkoxy group or a halogen atom.

"Aryl group" for Ar is, for example, preferably a phenyl group.

"Heteroaryl group" for Ar has the same meaning as that of the above-defined "heteroaryl group", more concretely, for example, it is preferably a pyridinyl group, a pyrimidinyl group or a pyrazinyl group. Even more preferably, Ar is a phenyl group, a pyrazinyl group or a pyrimidinyl group.

"Lower alkyl group" for the substituent is, for example, preferably a methyl group, an ethyl group, an n-propyl group, an isopropyl group, a 2-fluoroethyl group, a 3-fluoropropyl group, a methoxymethyl group, a 2-methoxyethyl group.

"Alkoxy group" for the substituent is, for example, preferably a methoxy group, an ethoxy group, an isopropoxy group, a benzyloxy group, a 2-fluoroethoxy group, a 3-fluoropropoxy group, a methoxymethoxy group, a 2-methoxyethoxy group.

"Halogen atom" for the substituent is, for example, preferably a fluorine atom, a chlorine atom, a bromine atom.

When Ar has two such substituents, then they may be the same or different.

From the above, more concretely, Ar is, for example, preferably a phenyl group, a methylphenyl group, a methoxyphenyl group, an ethoxyphenyl group, an isopropyloxyphenyl group, a 2-fluoroethoxyphenyl group, a 2-methoxyethoxyphenyl group, a chlorophenyl group, a fluorophenyl group, a pyridyl group, a pyrazinyl group, a pyrimidinyl group. Of those, preferred are a phenyl group, a methylphenyl group, a methoxyphenyl group, a 2-fluoroethoxyphenyl group, a chlorophenyl group, a fluorophenyl group, a pyridyl group, a pyrazinyl group, a pyrimidinyl group.

When Ar is a 6-membered aryl or heteroaryl group, then the bonding mode of the 6-membered Ar to $X_1$ and to the group of the following formula (VII):

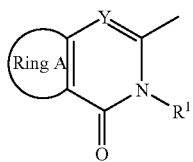

(VII)

[wherein the symbols have the same meanings as above] is, for example, preferably any of the following formula (VII-1):

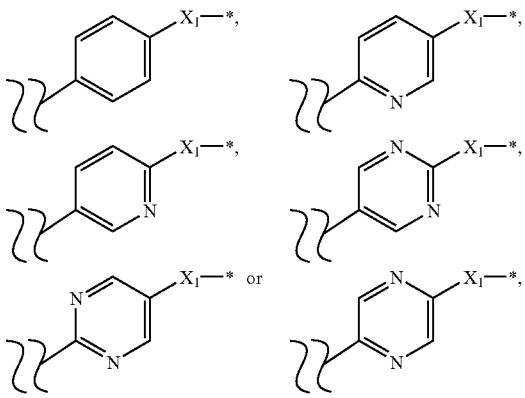

(VII-1)

[wherein * indicates the bonding position to $R^4$, and the following formula (VIII):

(VIII)

indicates the bonding position to the above formula (VII)].

When Ar is a 5-membered heteroaryl group, then its bonding mode corresponding to the above formula (VII-1) may be such that the 5-membered heteroaryl group of the above-defined "heteroaryl group" bonds to $X_1$ and to the formula (VII) and that the compound having the bonding mode may have a histamine receptor H3 antagonistic or inverse-agonistic effect to the same level as that of the compound or its pharmaceutically-acceptable salt of formula (I) where Ar is a 6-membered aryl or heteroaryl group.

Y is a nitrogen atom or CH, preferably a nitrogen atom.

Ring A is a 5- or 6-membered heteroaryl group having, in the ring, 1 or 2 hetero atoms of a nitrogen atom or a sulfur atom, or is a phenyl group.

"Heteroaryl group" for the ring A is, for example, preferably a thienyl group, a pyridinyl group, a pyrimidinyl group or a pyrazinyl group, more preferably a pyrimidinyl group or a thienyl group.

The ring A may have from 1 to 4, the same or different groups of $R^2$ and $R^3$ at the bondable position of the ring A.

$R^2$ and $R^3$ are the same or different, each representing a hydrogen atom, an amino group, an alkylamino group, a dialkylamino group, a nitro group, a cyano group, a hydroxyl group, a lower alkylsulfonyl group, a halogen atom, a lower alkyl group (the lower alkyl group may be substituted with a halogen atom), a cycloalkyl group (the cycloalkyl group may be substituted with a halogen atom), an alkoxy group (the alkoxy group may be substituted with a halogen atom or a hydroxyl group), a cycloalkoxy group (the cycloalkoxy group may be substituted with a halogen atom), an aryloxy group, an aralkyloxy group, a heteroaryloxy group, a heteroarylalkyloxy group, an aryl group, a heteroaryl group, an arylcarbamoyl group, a heteroarylcarbamoyl group, an arylalkylcarbamoyl group, a heteroarylalkylcarbamoyl group, a mono- or di-lower alkylcarbamoyl group, an aryloxycarbonylamino group, an arylalkyloxycarbonylamino group, a lower alkyloxycarbonylamino group, an alkylcarbonylamino group, an arylcarbonylamino group, a heteroarylcarbonylamino group, an arylalkylcarbonylamino group, a heteroarylalkylcarbonylamino group, an alkanoyl group, an arylcarbonyl group, an arylalkylcarbonyl group, a formyl group, a hydroxyl group, an alkylthio group, an alkoxycarbonylamino group, a lower alkylsulfonylamino group, an arylsulfonylamino group, an alkylaminosulfonyl group, or an arylaminosulfonyl group.

$R^2$ and $R^3$ are preferably a hydrogen atom, a lower alkyl group (the lower alkyl group may be substituted with a halogen atom), an alkoxy group (the alkoxy group may be substituted with a halogen atom or a hydroxyl group), an aryl group, a heteroaryl group, an alkylcarbonylamino group or an arylcarbonylamino group.

From the above, the ring A is, for example, a phenyl group, a thienyl group, a pyridinyl group, a pyrimidinyl group or a pyrazinyl group, preferably a phenyl group, a pyridinyl group, a pyrimidinyl group or a pyrazinyl group, more preferably a phenyl group, a pyridinyl group or a pyrimidinyl group, even more preferably a phenyl group or a pyridinyl group.

Accordingly, the group of the following formula (VII-2):

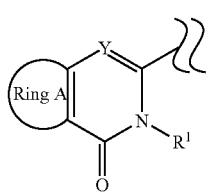

(VII-2)

[wherein the following formula (IX):

(IX)

indicates the bonding portion to Ar in formula (I); and the other symbols have the same meanings as above] includes, for example, those of the following formula (VII-3):

(VII-3)

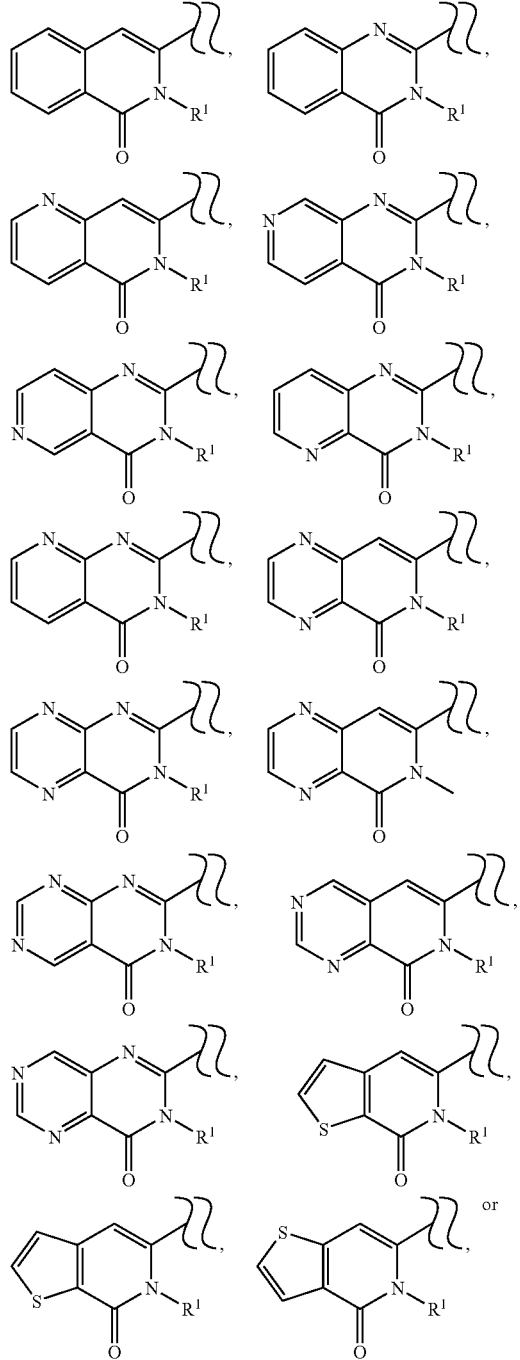

or

-continued

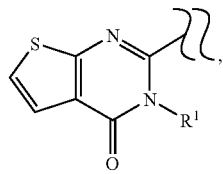

[wherein the symbols have the same meanings as above]. Of those, more preferred are the groups of the following formula (VII-4):

(VII-4)

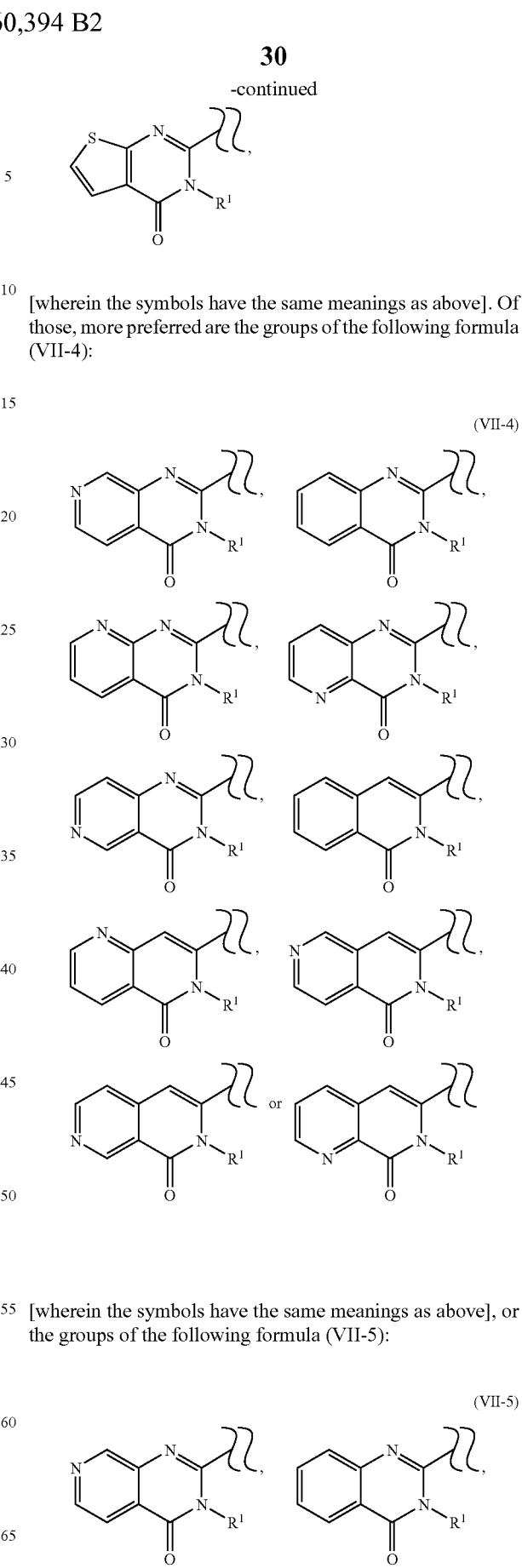

[wherein the symbols have the same meanings as above], or the groups of the following formula (VII-5):

(VII-5)

-continued

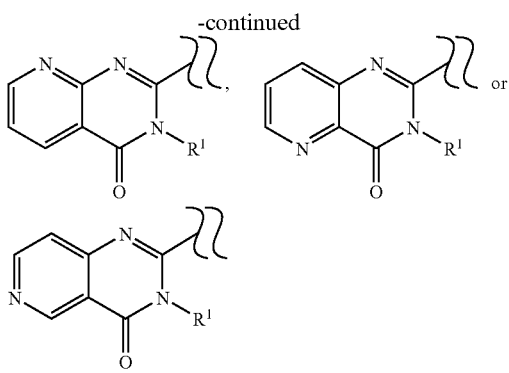

[wherein the symbols have the same meanings as above].

The groups of formulae (VII-3), (VII-4) and (VII-5) may have the above-mentioned $R^2$ or $R^3$ on the group corresponding to the ring A.

The above-mentioned preferred embodiments of $R^1$, $R^2$, $R^3$, $R^4$, $R^5$, $R^6$, $R^7$, $R^8$, $X_1$, Y, m, n and ring A may be combined in any desired manner.

The compounds of formula (I):

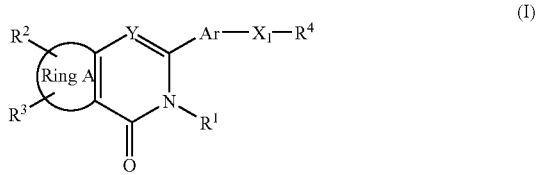

[wherein the symbols have the same meanings as above] are, for example, preferably the following compounds or their pharmaceutically-acceptable salts:

3,8-dimethyl-2-[4-(3-piperidin-1-ylpropoxy)phenyl]-4(3H)-quinazolinone;
3-methyl-2-[4-(3-piperidin-1-ylpropoxy)phenyl]-4(3H)-quinazolinone;
3-ethyl-2-[4-(3-piperidin-1-ylpropoxy)phenyl]-4(3H)-quinazolinone;
3,6-dimethyl-2-[4-(3-piperidin-1-ylpropoxy)phenyl]-4(3H)-quinazolinone;
3,5-dimethyl-2-[4-(3-piperidin-1-ylpropoxy)phenyl]-4(3H)-quinazolinone;
3-propyl-2-[4-(3-piperidin-1-ylpropoxy)phenyl]-4(3H)-quinazolinone;
3-benzyl-2-[4-(3-piperidin-1-ylpropoxy)phenyl]-4(3H)-quinazolinone;
3-ethyl-2-[3-(3-piperidin-1-ylpropoxy)phenyl]-4(3H)-quinazolinone;
3-isopropyl-2-[4-(3-piperidin-1-ylpropoxy)phenyl]-4(3H)-quinazolinone;
2-[4-(3-piperidin-1-ylpropoxy)phenyl]-3-phenyl-4(3H)-quinazolinone;
2-[4-(3-piperidin-1-ylpropoxy)phenyl]-3-(2,2,2-trifluoroethyl)-4(3H)-quinazolinone;
3,8-dimethyl-2-[4-(3-pyrrolidin-1-ylpropoxy)phenyl]-4(3H)-quinazolinone;
2-(2-methoxy-4-{3-[(3S)-3-methylpiperidin-1-yl]propoxy}phenyl)-3-methylquinazolin-4(3H)-one;
8-methoxy-2-(2-methoxy-4-{3-[(3S)-3-methylpiperidin-1-yl]propoxy}phenyl)-3-methylquinazolin-4(3H)-one;
3-methyl-2-[4-(3-piperidin-1-ylpropoxy)phenyl]pyrido[2,3-d]-pyrimidin-4(3H)-one;
3-methyl-2-[4-(3-pyrrolidin-1-ylpropoxy)phenyl]-4(3H)-quinazolinone;
3-methyl-2-[4-(1-cyclopentyl-4-piperidinyloxy)phenyl]-4(3H)-quinazolinone;
6-chloro-3-methyl-2-[4-(3-piperidin-1-ylpropoxy)phenyl]pyrido[3,4-d]-pyrimidin-4(3H)-one;
3,7-dimethyl-2-[4-(3-piperidin-1-ylpropoxy)phenyl]-4(3H)-quinazolinone;
3-methyl-2-[4-(3-pyrrolidin-1-ylpropoxy)phenyl]pyrido[2,3-d]-pyrimidin-4(3H)-one;
2-[4-(1-cyclopentyl-4-piperidinyloxy)phenyl]-3-methylpyrido[2,3-d]-pyrimidin-4(3H)-one;
2-[4-(1-cyclobutyl-4-piperidinyloxy)phenyl]-3-methylpyrido[2,3-d]-pyrimidin-4(3H)-one;
2-[4-(1-cyclopentyl-4-piperidinyloxy)phenyl]-3-(2-methoxyethyl)pyrido[2,3-d]pyrimidin-4(3H)-one;
2-{4-[(1-cyclobutylpiperidin-4-yl)oxy]phenyl}-8-methoxyquinazolin-4(3H)-one;
7-bromo-2-{4-[(1-cyclopentylpiperidin-4-yl)oxy]-2-methoxyphenyl}-3-methylpyrido[3,2-d]pyrimidin-4(3H)-one;
7-bromo-2-{4-[(1-cyclobutylpiperidin-4-yl)oxy]-2-methoxyphenyl}-3-methylpyrido[3,2-d]pyrimidin-4(3H)-one;
2-{6-[(1-cyclobutylpiperidin-4-yl)oxy]pyridin-3-yl}-8-methoxy-3-methylquinazolin-4(3H)-one;
6-chloro-2-{4-[(1-cyclopentylpiperidin-4-yl)oxy]phenyl}-3-methylpyrido[3,4-d]pyrimidin-4(3H)-one; 2-{4-[(1-cyclobutylpiperidin-4-yl)oxy]phenyl-8-methoxy-3-methylpyrido[3,4-d]pyrimidin-4(3H)-one;
6-chloro-2-{4-[(1-cyclobutylpiperidin-4-yl)oxy]phenyl}-3-methylpyrido[3,4-d]pyrimidin-4(3H)-one;
6-chloro-2-[2-methoxy-4-(3-pyrrolidin-1-ylpropoxy)phenyl]-3-methylpyrido[3,4-d]pyrimidin-4(3H)-one;
2-{4-[(1-cyclobutylpiperidin-4-yl)oxy]phenyl}-8-methylquinazolin-4(3H)-one;
8-methoxy-3-methyl-2-[4-(3-pyrrolidin-1-ylpropoxy)phenyl]pyrido[3,4-d]pyrimidin-4(3H)-one;
2-{4-[(1-cyclopentylpiperidin-4-yl)oxy]phenyl}-8-methoxy-3-methylpyrido[3,4-d]pyrimidin-4(3H)-one;
8-chloro-2-{4-[(1-cyclobutylpiperidin-4-yl)oxy]phenyl}-3-methylquinazolin-4(3H)-one;
2-{4-[(1-cyclobutylpiperidin-4-yl)oxy]phenyl}-3-methyl-8-(trifluoromethyl)quinazolin-4(3H)-one;
2-{6-[(1-cyclobutylpiperidin-4-yl)oxy]pyridin-3-yl}-3,8-dimethylquinazolin-4(3H)-one;
6-chloro-2-{4-[(1-cyclobutylpiperidin-4-yl)oxy]-2-methoxyphenyl}-3-methylpyrido[3,4-d]pyrimidin-4(3H)-one;
6-chloro-2-{4-[(1-cyclopentylpiperidin-4-yl)oxy]-2-methoxyphenyl}-3-methylpyrido[3,4-d]pyrimidin-4(3H)-one;
2-{4-[(1-cyclobutylpiperidin-4-yl)oxy]phenyl-8-fluoro-3-methylquinazolin-4(3H)-one;
2-{4-[(1-cyclopentylpiperidin-4-yl)oxy]phenyl-8-fluoro-3-methylquinazolin-4(3H)-one;
8-fluoro-2-(2-methoxy-4-{3-[(3S)-3-methylpiperidin-1-yl]propoxy}phenyl)-3-methylquinazolin-4-(3H)-one;
5-fluoro-3-methyl-2-[4-(3-pyrrolidin-1-ylpropoxy)phenyl]quinazolin-4(3H)-one;
2-{4-[(1-cyclobutylpiperidin-4-yl)oxy]phenyl}-5-fluoro-3-methylquinazolin-4(3H)-one;
2-{4-[(1-cyclobutylpiperidin-4-yl)oxy]phenyl}-3,8-dimethylpyrido[4,3-d]pyrimidin-4(3H)-one;
2-{2-[(1-cyclobutylpiperidin-4-yl)oxy]pyrimidin-5-yl}-8-methoxy-3-methylquinazolin-4(3H)-one;
2-{2-[(1-cyclobutylpiperidin-4-yl)oxy]pyrimidin-5-yl}-8-methoxy-3-methylpyrido[3,4-d]pyrimidin-4(3H)-one;
2-{6-[(1-cyclobutylpiperidin-4-yl)oxy]pyridin-3-yl}-8-methoxy-3-methylpyrido[3,4-d]pyrimidin-4(3H)-one;

2-{4-[(1-cyclobutylpiperidin-4-yl)oxy]phenyl-6-methoxy-3-methylpyrido[3,4-d]pyrimidin-4(3H)-one;
2-{4-[(1-cyclopentylpiperidin-4-yl)oxy]phenyl-6-methoxy-3-methylpyrido[3,4-d]pyrimidin-4(3H)-one;
3-methyl-2-(4-{3-[(3S)-3-methylpiperidin-1-yl]propoxy}phenyl)pyrido[3,2-d]pyrimidin-4(3H)-one;
2-{4-[(1-cyclobutylpiperidin-4-yl)oxy]phenyl-3-methylpyrido[3,2-d]pyrimidin-4(3H)-one;
2-{4-[(1-cyclopentylpiperidin-4-yl)oxy]phenyl-3-methylpyrido[3,2-d]pyrimidin-4(3H)-one;
3,8-dimethyl-2-(4-{3-[(3S)-3-methylpiperidin-1-yl]propoxy}phenyl)pyrido[4,3-d]pyrimidin-4(3H)-one;
7-bromo-3-methyl-2-(4-{3-[(3S)-3-methylpiperidin-1-yl]propoxy}phenyl)pyrido[3,2-d]pyrimidin-4(3H)-one;
7-methoxy-3-methyl-2-[4-(3-pyrrolidin-1-ylpropoxy)phenyl]quinazolin-4(3H)-one;
7-methoxy-3-methyl-2-[4-(3-[(3S)-3-methylpiperidin-1-yl]propoxy)phenyl]quinazolin-4(3H)-one;
2-{4-[(1-cyclobutylpiperidin-4-yl)oxy]phenyl}-7-methoxy-3-methylquinazolin-4(3H)-one;
2-{4-[(1-cyclobutylpiperidin-4-yl)oxy]phenyl}-8-methoxy-3-methylpyrido[3,2-d]pyrimidin-4(3H)-one;
7-bromo-2-[2-(2-fluoroethoxy)-4-(3-piperidin-1-ylpropoxy)phenyl]-3-methylquinazolin-4(3H)-one;
6-chloro-2-[2-(2-fluoroethoxy)-4-(3-pyrrolidin-1-ylpropoxy)phenyl]-3-methylpyrido[3,4-d]pyrimidin-4(3H)-one;
2-{4-[(1-cyclobutylpiperidin-4-yl)oxy]phenyl}-4-(2-fluoroethoxy)-8-methoxyquinazolinone;
2-{4-[(1-cyclobutylpiperidin-4-yl)oxy]phenyl}-3-methylpyrido[3,4-d]pyrimidin-4(3H)-one;
2-{4-[(1-cyclopentylpiperidin-4-yl)oxy]phenyl}-3-methylpyrido[3,4-d]pyrimidin-4(3H)-one;
2-{4-[(1-cyclobutylpiperidin-4-yl)oxy]phenyl}-7-(2-fluoroethyl)-3-methyl-3,7-dihydropyrido[3,4-d]pyrimidine-4,8-dione;
2-{4-[(1-cyclopentylpiperidin-4-yl)oxy]phenyl}-7-(2-fluoroethyl)-3-methyl-3,7-dihydropyrido[3,4-d]pyrimidine-4,8-dione;
2-{4-[(1-cyclobutylpiperidin-4-yl)oxy]phenyl}-8-(difluoromethoxy)-3-methylpyrido[3,4-d]pyrimidin-4(3H)-one;
2-{4-[(1-cyclobutylpiperidin-4-yl)oxy]phenyl}-7-(difluoromethyl)-3-methyl-3,7-dihydropyrido[3,4-d]pyrimidine-4,8-dione;
3-methyl-2-[4-(3-piperidin-1-ylpropoxy)-phenyl]pyrido[3,4-d]pyrimidin-4(3H)-one;
3-methyl-2-[3-(3-piperidin-1-ylpropoxy)-phenyl]-6-methylsulfonylamino-4(3H)-quinazolinone;
3-methyl-2-[3-(3-piperidin-1-ylpropoxy)-phenyl]-7-methylsulfonylamino-4(3H)-quinazolinone;
3-methyl-7-nitro-2-[3-(3-piperidin-1-ylpropoxy)phenyl]-4(3H)-quinazolinone;
3-methyl-7-methylsulfonylamino-2-[4-(3-pyrrolidin-1-ylpropoxy)phenyl]-4(3H)-quinazolinone;
3-methyl-6-methylsulfonylamino-2-[4-(3-pyrrolidin-1-ylpropoxy)phenyl]-4(3H)-quinazolinone;
6-acetylamino-3-methyl-2-[4-(3-piperidin-1-ylpropoxy)phenyl]-4(3H)-quinazolinone;
3-methyl-2-[4-(3-piperidin-1-ylpropoxy)phenyl]-6-trifluoromethylcarbonylamino-4(3H)-quinazolinone;
3-methyl-2-[2-methyl-4-(3-pyrrolidin-1-ylpropoxy)phenyl]-4(3H)-quinazolinone;
3-methyl-2-[2-fluoro-4-(3-pyrrolidin-1-ylpropoxy)-phenyl]-4(3H)-quinazolinone;
6-bromo-3-methyl-2-[3-methoxy-4-(3-pyrrolidin-1-ylpropoxy)-phenyl]-4(3H)-quinazolinone;
6-bromo-3-methyl-2-[2-methoxy-4-(3-pyrrolidin-1-ylpropoxy)-phenyl]-4(3H)-quinazolinone;
2-[2-methoxy-4-(3-pyrrolidin-1-ylpropoxy)-phenyl]-3-methylpyrido[2,3-d]pyrimidin-4(3H)-one;
8-methoxy-3-methyl-2-[4-(3-pyrrolidin-1-ylpropoxy)phenyl]quinazolin-4(3H)-one;
3-allyl-2-[4-(3-pyrrolidin-ylpropoxy)phenyl]pyrido[2,3-d]pyrimidin-4(3H)-one;
2-[2-methoxy-4-(3-piperidin-1-ylpropoxy)phenyl]-3-methylpyrido[2,3-d]pyrimidin-4(3H)-one;
3-methyl-2-[2-methyl-4-(1-cyclobutyl-4-piperidinyloxy)phenyl]-4(3H)-quinazolinone;
3-methyl-2-[2-methyl-4-(1-cyclopentyl-4-piperidinyloxy)phenyl]-4(3H)-quinazolinone;
3-methyl-2-[2-methyl-4-(1-cyclohexyl-4-piperidinyloxy)phenyl]-4(3H)-quinazolinone;
3-methyl-2-[4-(1-cyclobutyl-4-piperidinyloxy)phenyl]-4(3H)-quinazolinone;
3-methyl-2-[4-(1-cyclopropyl-4-piperidinyloxy)phenyl]-4(3H)-quinazolinone;
8-methoxy-3-methyl-2-[4-(1-cyclobutyl-4-piperidinyloxy)phenyl]-4(3H)-quinazolinone;
6-methoxy-3-methyl-2-[4-(1-cyclobutyl-4-piperidinyloxy)phenyl]-4(3H)-quinazolinone;
5-methoxy-3-methyl-2-[4-(1-cyclopropyl-4-piperidinyloxy)phenyl]-4(3H)-quinazolinone;
8-methoxy-3-methyl-2-[4-(1-cyclopropyl-4-piperidinyloxy)phenyl]-4(3H)-quinazolinone;
5-methoxy-3-methyl-2-[4-(1-cyclobutyl-4-piperidinyloxy)phenyl]-4(3H)-quinazolinone;
2-{4-[(1-cyclobutylpiperidin-4-yl)oxy]phenyl}-3,8-dimethylquinazolin-4(3H)-one;
7-bromo-2-{4-[(1-cyclobutylpiperidin-4-yl)oxy]phenyl}-3-methylpyrido[3,2-d]pyrimidin-4(3H)-one;
7-bromo-2-{4-[(1-cyclopentylpiperidin-4-yl)oxy]phenyl}-3-methylpyrido[3,2-d]pyrimidin-4(3H)-one;
2-{4-[(1-cyclobutylpiperidin-4-yl)oxy]-2-methoxyphenyl}-3-methylpyrido[2,3-d]pyrimidin-4(3H)-one;
2-{4-[(1-cyclopentylpiperidin-4-yl)oxy]-2-methoxyphenyl}-3-methylpyrido[2,3-d]pyrimidin-4(3H)-one;
2-{4-[(1-cyclopropylpiperidin-4-yl)oxy]phenyl}-3-ethyl-8-methylquinazolin-4(3H)-one;
2-{4-[(1-cyclobutylpiperidin-4-yl)oxy]phenyl}-3-ethyl-8-methylquinazolin-4(3H)-one;
2-{4-[(1-cyclopentylpiperidin-4-yl)oxy]phenyl}-3-ethyl-8-methylquinazolin-4(3H)-one;
2-{4-[(1-cyclobutylpiperidin-4-yl)oxy]-2-fluorophenyl}-3-methylquinazolin-4(3H)-one;
2-{4-[(1-cyclopentylpiperidin-4-yl)oxy]-2-fluorophenyl}-3-methylquinazolin-4(3H)-one; and
tert-butyl 4-oxo-2-[4-(3-piperidin-1-ylpropoxy)phenyl]-[3,4H]-quinazolinecarboxylate.

Of those, more preferred are the following compounds or their pharmaceutically-acceptable salts:

3-methyl-2-[4-(3-piperidin-1-ylpropoxy)phenyl]pyrido[2,3-d]-pyrimidin-4(3H)-one;
3-methyl-2-[4-(3-pyrrolidin-1-ylpropoxy)phenyl]-4(3H)-quinazolinone;
2-[4-(1-cyclopentyl-4-piperidinyloxy)phenyl]-3-methylpyrido[2,3-d]pyrimidin-4(3H)-one;
2-[4-(1-cyclobutyl-4-piperidinyloxy)phenyl]-3-methylpyrido[2,3-d]-pyrimidin-4(3H)-one;
2-{4-[(1-cyclobutylpiperidin-4-yl)oxy]phenyl}-8-methoxy-3-methylpyrido[3,4-d]pyrimidin-4(3H)-one;
2-{6-[(1-cyclobutylpiperidin-4-yl)oxy]pyridin-3-yl}-8-methoxy-3-methylpyrido[3,4-d]pyrimidin-4(3H)-one;
2-{4-[(1-cyclobutylpiperidin-4-yl)oxy]phenyl}-6-methoxy-3-methylpyrido[3,4-d]pyrimidin-4(3H)-one;
3-methyl-2-(4-{3-[(3S)-3-methylpiperidin-1-yl]propoxy}phenyl)pyrido[3,2-d]pyrimidin-4(3H)-one;
2-{4-[(1-cyclobutylpiperidin-4-yl)oxy]phenyl}-3-methylpyrido[3,2-d]pyrimidin-4(3H)-one;
2-{4-[(1-cyclobutylpiperidin-4-yl)oxy]phenyl}-8-methoxy-3-methylpyrido[3,2-d]pyrimidin-4(3H)-one;

2-{4-[(1-cyclobutylpiperidin-4-yl)oxy]phenyl}-3-methylpy-rido[3,4-d]pyrimidin-4(3H)-one;
3-methyl-2-[2-methyl-4-(3-pyrrolidin-1-ylpropoxy)phenyl]-4(3H)-quinazolinone;
3-methyl-2-[2-methyl-4-(1-cyclobutyl-4-piperidinyloxy)phenyl]-4(3H)-quinazolinone;
3-methyl-2-[4-(1-cyclobutyl-4-piperidinyloxy)phenyl]-4(3H)-quinazolinone;
8-methoxy-3-methyl-2-[4-(1-cyclobutyl-4-piperidinyloxy)phenyl]-4(3H)-quinazolinone; or
2-{4-[(1-cyclobutylpiperidin-4-yl)oxy]phenyl}-3,8-dimethylquinazolin-4(3H)-one.

Compounds of a formula (I-1):

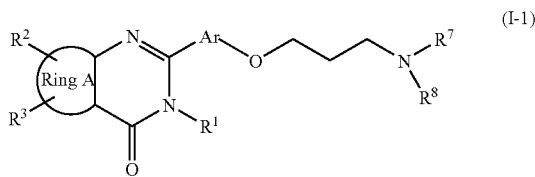

or a formula (I-2):

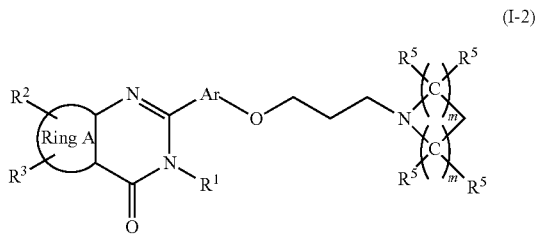

[wherein the symbols have the same meanings as above] of the invention may be produced, for example, according to the following method:

The reaction of this step may be ordinary amidation to be attained according to a method described in literature (for example, *Bases and Experiments of Peptide Synthesis*, Nobuo Izumiya, by Maruzen, 1983; *Comprehensive Organic Synthesis*, Vol. 6, by Pergamon Press, 1991), or a method similar to it, or a combination of the method with an ordinary method. For example, it may be attained by the use of a condensing agent well known to those skilled in the art, or according to an ester activation method, a mixed acid anhydride method, an acid chloride method or a carbodiimide method available to those skilled in the art. The amidation reagent includes, for example, thionyl chloride, oxalyl chloride, N,N-dicyclohexylcarbodiimide, 1-methyl-2-bromopyridinium iodide, N,N'-carbonyldiimidazole, diphenylphosphoryl chloride, diphenylphosphorylazide, N,N'-disuccinimidyl carbonate, N,N'-disuccinimidyl oxalate, 1-ethyl-3-(3-dimethylaminopropyl)carbodiimide hydrochloride, ethyl chloroformate, isobutyl chloroformate, or benzotriazol-1-yl-oxy-tris(dimethylamino)phosphonium hexafluorophosphate. Of those, preferred are thionyl chloride, 1-ethyl-3-(3-dimethylaminopropyl)carbodiimide hydrochloride, N,N-dicyclohexylcarbodiimide, or benzotriazol-1-yl-oxy-tris(dimethylamino)phosphonium hexafluorophosphate. In amidation, a base and a condensation promoter may be used along with the above-mentioned amidation reagent.

The base usable herein includes, for example, tertiary aliphatic amines such as trimethylamine, triethylamine, N,N-diisopropylethylamine, N-methylmorpholine, N-methylpyrrolidine, N-methylpiperidine, N,N-dimethylaniline, 1,8-diazabicyclo[5.4.0]undec-7-ene (DBU), 1,5-azabicyclo[4.3.0]non-5-ene (DBN); and aromatic amines such as pyridine, 4-dimethylaminopyridine, picoline, lutidine, quinoline, isoquinoline. Of those, for example, preferred are tertiary aliphatic amines; and more preferred are triethylamine, N,N-diisopropylethylamine.

The condensation promoter usable herein includes, for example, N-hydroxybenzotriazole hydrate, N-hydroxysuccinimide, N-hydroxy-5-norbornene-2,3-dicarboxyimide, or

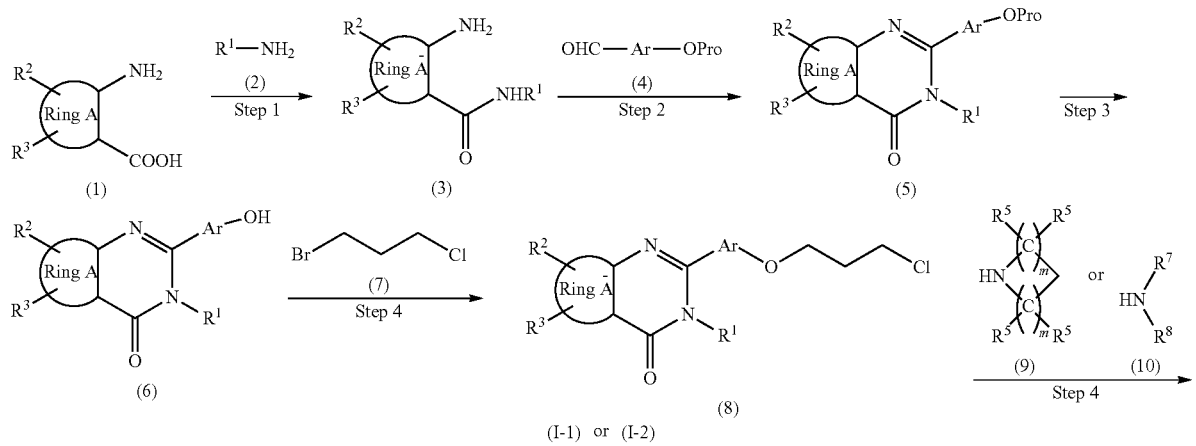

Step 5
[wherein Pro represents a hydroxyl-protective group; and the other symbols have the same meanings as above.]

The steps are described below.

(Step 1)

This step is a method for producing a compound (3) by reacting a compound (1) and a compound (2).

3-hydroxy-3,4-dihydro-4-oxo-1,2,3-benzotriazole. Of those, for example, preferred is N-hydroxybenzotriazole.

The amount of the compound (2) to be used herein may be generally from 1 to 10 equivalents relative to 1 equivalent of the compound (1) or its reactive derivative, preferably from 1 to 3 equivalents.

The compound (1) includes, for example, 2-aminobenzoic acid derivatives, 2-aminonicotinic acid derivatives.

The compound (2) includes, for example, methylamine, ethylamine, propylamine, benzylamine, aniline.

The amount of the amidation reagent to be used may be generally from 1 to 10 equivalents relative to one equivalent of the compound (1) or its reactive derivative, preferably from 1 to 3 equivalents.

The amount of the condensation promoter to be used may be generally from 1 to 10 equivalents relative to one equivalent of the compound (1) or its reactive derivative, preferably from 1 to 3 equivalents.

The amount of the base to be used may be generally from 1 to 10 equivalents relative to one equivalent of the compound (1) or its reactive derivative, preferably from 1 to 5 equivalents.

Not specifically defined, the reaction solvent may be any one not interfering with the reaction. Concretely, it includes, for example, methylene chloride, chloroform, 1,2-dichloroethane, N,N-dimethylformamide, ethyl acetate, methyl acetate, acetonitrile, benzene, xylene, toluene, 1,4-dioxane, tetrahydrofuran, dimethoxyethane, and their mixed solvents. For ensuring a preferred reaction temperature, the solvent is, for example, preferably acetonitrile, tetrahydrofuran, dimethoxyethane or N,N-dimethylformamide.

The reaction temperature may be generally from −78° C. to the boiling point of the solvent, preferably from 0° C. to 50° C.

The reaction time may be generally from 0.5 hours to 96 hours, preferably from 3 to 24 hours.

Regarding the base, the amidation reagent and the condensation promoter for use in this step, one or more different types of them may be combined and used.

Thus obtained, the compound (3) may be isolated and purified through any known separation and purification method of, for example, condensation, reduced-pressure condensation, solvent extraction, crystallization, reprecipitation or chromatography, or not isolated and purified, it may be processed in the next step.

(Step 2)

This step is a method for producing a compound (5) by reacting the compound (3) obtained in the previous step 1 with an aldehyde compound (4) in the presence of $NaHSO_3$.

In the compound (4), Pro means a hydroxyl-protective group. The protective group may be introduced into the compound according to a method described in literature (for example, *Protective Groups in Organic Synthesis*, written by T. W. Green, 2nd Ed., by John Wiley & Sons, 1991), or a method similar to it, or a combination of the method with an ordinary method. Pro in the compound (4) includes, for example, a lower alkyl group such as a methyl group, an aralkyl group such as a benzyl group, a lower alkoxyalkyl group such as a methoxymethyl group, a lower alkylthioalkyl group such as a methylthiomethyl group.

In this step, the amount of $NaHSO_3$ to be used may be generally from 1 to 20 equivalents relative to one equivalent of the compound (3), preferably from 1 to 3 equivalents.

Not specifically defined, the reaction solvent may be any one not interfering with the reaction. Concretely, for example, it includes dimethyl sulfoxide, N,N-dimethylformamide, N,N-dimethylacetamide, ethyl acetate, methyl acetate, acetonitrile, propionitrile, 1,4-dioxane, tetrahydrofuran, dimethoxyethane, and their mixed solvents. Of those, for example, preferred are dimethyl sulfoxide, N,N-dimethylformamide, N,N-dimethylacetamide.

The reaction temperature may be generally from room temperature to 200° C., preferably from 80° C. to 150° C.

The reaction time may be generally from 1 hour to 90 hours, preferably from 1 hour to 48 hours.

Thus obtained, the compound (5) may be isolated and purified through any known separation and purification method of, for example, condensation, reduced-pressure condensation, crystallization, solvent extraction, reprecipitation or chromatography, or not isolated and purified, it may be processed in the next step.

(Step 3)

This step is a method for producing a compound (6) by removing the hydroxyl-protective group that the compound obtained in the previous step 2 has.

The removal of the hydroxyl-protective group Pro may be attained according to a method described in literature (for example, *Protective Groups in Organic Synthesis*, written by T. W. Green, 2nd Ed., by John Wiley & Sons, 1991), or a method similar to it, or a combination of the method with an ordinary method.

When Pro is a methyl group, then the methyl group may be removed, for example, according to the following method.

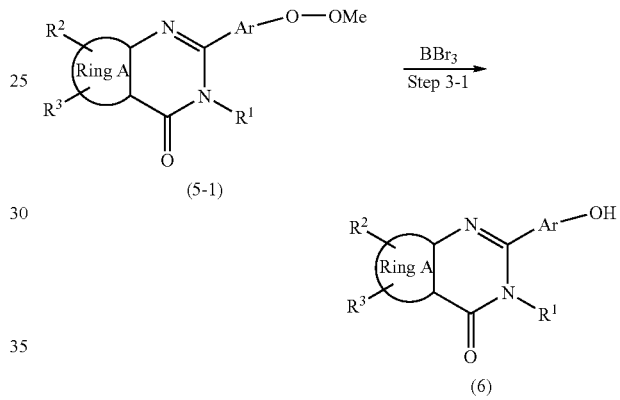

[wherein the symbols have the same meanings as above.]

(Step 3-1)

This step is a method for producing a compound (6) by removing the methyl group from the methoxy group that the compound (5-1) has, by the use of $BBr_3$.

The amount of $BBr_3$ to be used may be generally from 1 to 10 equivalents relative to one equivalent of the compound (5-1), preferably from 1 to 3 equivalents.

Not specifically defined, the reaction solvent may be any one not interfering with the reaction. For example, it includes methylene chloride, chloroform, 1,2-dichloroethane, N,N-dimethylformamide, N,N-dimethylacetamide, ethyl acetate, methyl acetate, acetonitrile, propionitrile, benzene, xylene, toluene, and their mixed solvents. Of those, for example, preferred are methylene chloride, chloroform, 1,2-dichloroethane, benzene, xylene, toluene.

The reaction time may be generally from 1 hour to 90 hours, preferably from 1 hour to 24 hours.

The reaction temperature may be generally from −78° C. to 100° C., preferably from 0° C. to 60° C.

Thus obtained, the compound (6) may be isolated and purified through any known separation and purification method of, for example, condensation, reduced-pressure condensation, crystallization, solvent extraction, reprecipitation or chromatography, or not isolated and purified, it may be processed in the next step.

When Pro is a benzyl group, then concretely the benzyl group may be removed, for example, according to the following method:

(5-2)

Catalytic Reduction
Step 3-2

(6)

[wherein Bn represents a benzyl group; and the other symbols have the same meanings as above.]

(Step 3-2)

This step is a method for producing a compound (6) by removing the benzyl group that the compound (5-2) has, through catalytic reduction in a hydrogen atmosphere.

The reducing agent to be used in this step includes palladium-carbon, palladium hydroxide, rhodium-carbon, Raney nickel.

The amount of the reducing agent to be used may be generally from 0.01 to 10 equivalents relative to one equivalent of the compound (5-2), preferably from 0.01 to 1 equivalent.

Not specifically defined, the reaction solvent may be any one not interfering with the reaction. For example, it includes water, methanol, ethanol, isopropanol, dimethylsulfoxide, N,N-dimethylformamide, N,N-dimethylacetamide, ethyl acetate, methyl acetate, benzene, xylene, toluene, 1,4-dioxane, tetrahydrofuran, dimethoxyethane, and their mixed solvents. Of those, preferred are methanol, ethanol, ethyl acetate, methyl acetate.

The reaction time may be generally from 1 hour to 100 hours, preferably from 1 hour to 24 hours.

The reaction temperature may be generally from 0° C. to 50° C., preferably from room temperature to 40° C.

The compound (6) may also be produced, using a compound of a formula (4-1):

OHC—Ar—OH      (4-1)

[wherein the symbols have the same meanings as above], which corresponds to the compound (4) used in the step 2 but in which the hydroxyl group is not protected. This embodiment gives the compound (6) not via deprotection of the previous step 3.

Thus obtained, the compound (6) may be isolated and purified through any known separation and purification method of, for example, condensation, reduced-pressure condensation, crystallization, solvent extraction, reprecipitation or chromatography, or not isolated and purified, it may be processed in the next step.

(Step 4)

This step is a method for producing a compound (8) by reacting the compound (6) obtained in the previous step 3 with a compound (7) (1-bromo-3-chloro-propane) in the presence of a base.

The amount of 1-bromo-3-chloro-propane to be used in this step may be generally from 1 to 10 equivalents relative to one equivalent of the compound (6), preferably from 1 to 3 equivalents.

The base to be used in this step includes, for example, sodium carbonate, sodium hydrogencarbonate, potassium carbonate, potassium hydrogencarbonate, cesium carbonate, sodium hydride, diisopropylethylamine. Of those, preferred are sodium carbonate, potassium carbonate, cesium carbonate.

The amount of the base to be used in this step may be generally from 1 to 10 equivalents relative to one equivalent of the compound (6), preferably from 1 to 3 equivalents.

Not specifically defined, the reaction solvent may be any one not interfering with the reaction. For example, it includes dimethylsulfoxide, N,N-dimethylformamide, N,N-dimethylacetamide, ethyl acetate, methyl acetate, acetonitrile, propionitrile, 1,4-dioxane, tetrahydrofuran, dimethoxyethane, and their mixed solvents. Of those, for example, preferred are N,N-dimethylformamide, tetrahydrofuran.

The reaction time may be generally from 1 hour to 48 hours, preferably from 3 hours to 12 hours.

The reaction temperature may be generally from 0° C. to 100° C., preferably from room temperature to 80° C.

Thus obtained, the compound (8) may be isolated and purified through any known separation and purification method of, for example, condensation, reduced-pressure condensation, crystallization, solvent extraction, reprecipitation or chromatography, or not isolated and purified, it may be processed in the next step.

(Step 5)

This step is for reacting the compound (8) obtained in the previous step 4 with an amino compound (9):

(9)

or a compound (10):

(10)

[wherein the symbols have the same meanings as above], in the presence of a base to produce a compound (I-1) of the invention:

(I-1)

of a compound (I-2) of the invention:

(I-2)

[wherein the symbols have the same meanings as above].

The amount of the compound (9) or (10) to be used in this step may be generally from 1 to 0 equivalent, preferably from 1 to 3 equivalents, relative to one equivalent of the compound (8).

Concretely, the compound (9) to be used includes, for example, piperidine, pyrrolidine, (2R)-2-methylpyrrolidine, (2S)-2-methylpyrrolidine, (3S)-3-methylpiperidine, azetidine, homopiperidine, morpholine, azepane, azocane.

The compound (10) to be used includes, for example, dimethylamine, diethylamine, N-methylaniline. Potassium iodide or potassium bromide may be made to exist in this reaction system.

The amount of potassium iodide or potassium bromide to be used may be generally from 0.1 to 5 equivalents relative to one equivalent of the compound (8), preferably from 0.5 to 1 equivalent.

Not specifically defined, the reaction solvent may be any one not interfering with the reaction. For example, it includes dimethylsulfoxide, N,N-dimethylformamide, N,N-dimethylacetamide, ethyl acetate, methyl acetate, acetonitrile, propionitrile, benzene, xylene, toluene, 1,4-dioxane, tetrahydrofuran, dimethoxyethane, and their mixed solvents. Of those, preferred are dimethylsulfoxide, N,N-dimethylformamide, N,N-dimethylacetamide, tetrahydrofuran.

The reaction time may be generally from 1 hour to 48 hours, preferably from 1 hour to 12 hours.

The reaction time may be generally from 0° C. to 100° C., preferably from 40° C. to 80° C.

Thus obtained, the compound (I-1) or (I-2) of the invention may be isolated and purified through any known separation and purification method of, for example, condensation, reduced-pressure condensation, crystallization, solvent extraction, reprecipitation or chromatography.

The compound (I-1) or (I-2) of the invention may also be produced by reacting the above-mentioned compound of formula (6):

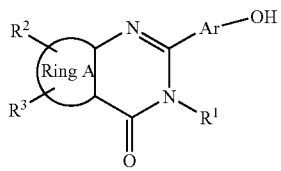

(6)

[wherein the symbols have the same meanings as above] with a compound of a formula (II):

(11)

or a formula (12):

(12)

[wherein $X_2$ represents a leaving group, and the other symbols have the same meanings as above] to give the compound of formula (I-1) or (I-2) of the invention.

The amount of the compound (11) or (12) to be used in this step may be generally from 1 to 5 equivalents relative to one equivalent of the compound (6), preferably from 1 to 2 equivalents.

$X_2$ may be any one capable of functioning as a leaving group in the reaction of the compound (6) with the compound (11) or (12). For example, it includes a halogen atom such as a chlorine atom, bromine atom; and a tosyl group, mesyl group.

Concretely, the compound (11) to be used herein is, for example, diethyl(3-bromopropyl)amine.

The compound (12) to be used includes, for example, 1-(3-bromopropyl)pyrrolidin, (2R)-1-(3-bromopropyl)-2-methylpyrrolidine, (2S)-1-(3-bromopropyl)-2-methylpyrrolidine, (3S)-1-(3-bromopropyl)-3-methylpiperidine.

Not specifically defined, the reaction solvent may be any one not interfering with the reaction. For example, it includes dimethylsulfoxide, N,N-dimethylformamide, N,N-dimethylacetamide, ethyl acetate, methyl acetate, acetonitrile, propionitrile, benzene, xylene, toluene, 1,4-dioxane, tetrahydrofuran, dimethoxyethane, and their mixed solvents. Of those, for example, preferred are N,N-dimethylformamide, tetrahydrofuran.

The reaction time may be generally from 1 hour to 48 hours, preferably from 1 hour to 12 hours.

The reaction temperature may be generally from 0° C. to 100° C., preferably from 40° C. to 80° C.

Thus obtained, the compound (I-1) or (I-2) of the invention may be isolated and purified through any known separation and purification method of, for example, condensation, reduced-pressure condensation, crystallization, solvent extraction, reprecipitation or chromatography.

The compound (I-1) or (I-2) of the invention may also be produced by reacting the compound (3) obtained in the previous step 1 with a compound of the following formula (13):

(13)

or the following formula (14):

(14)

[wherein the symbols have the same meanings as above].

In this step, TsOH (tosyl acid) (or its hydrate) and DDQ (2,3-dichloro-5,6-dicyano-1,4-benzoquinone) may be used.

The amount of TsOH (or its hydrate) to be used in this step may be generally from 0.1 to 10 equivalents relative to one equivalent of the compound (3), preferably from 0.5 to 2 equivalents.

Acetic acid or fumaric acid may be used in place of TsOH.

The amount of DDQ to be used in this step may be generally from 1 to 10 equivalent relative to one equivalent of the compound (3), preferably from 1 to 3 equivalents.

Any other oxidizing agent such as manganese dioxide may be used in place of DDQ.

The amount of the compound (13) or the compound (14) to be used in this step may be generally from 1 to 5 equivalent relative to one equivalent of the compound (3), preferably from 1 to 2 equivalents.

Concretely, the compound (13) to be used is, for example, 4-[3-(diethylamino)propoxy]benzaldehyde.

The compound (14) to be used includes, for example, 4-(3-piperidin-1-ylpropoxy)benzaldehyde, 4-(3-pyrrolidin-1-ylpropoxy)benzaldehyde, 4-{3-[(3S)-3-methylpiperidin-1-yl]propoxy}benzaldehyde.

Not specifically defined, the reaction solvent may be any one not interfering with the reaction. For example, it includes dimethylsulfoxide, N,N-dimethylformamide, N,N-dimethylacetamide, acetonitrile, propionitrile, benzene, xylene, toluene, 1,4-dioxane, tetrahydrofuran, dimethoxyethane, and their mixed solvents. Of those, preferred are toluene, 1,4-dioxane, tetrahydrofuran.

The reaction time may be generally from 1 hour to 90 hours, preferably from 1 hour to 48 hours.

The reaction temperature may be generally from room temperature to 150° C., preferably from 60° C. to 130° C.

Thus obtained, the compound (I-1) or (I-2) of the invention may be isolated and purified through any known separation and purification method of, for example, condensation, reduced-pressure condensation, crystallization, solvent extraction, reprecipitation or chromatography.

A compound (I-3) of the invention,

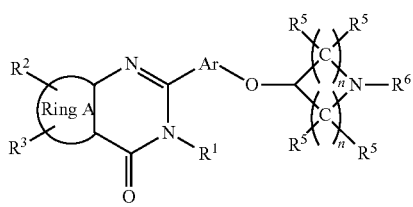

[wherein the symbols have the same meanings as above: may be produced, for example, according to the following method:

[wherein Pro1 represents an amino-protective group; $R^{61}$ represents a linear or branched lower alkyl group; r indicates from 1 to 7; and the other symbols have the same meanings as above.]

Respective steps are explained below.

(Step 6)

This step is a method for producing a compound (16) by reacting the compound (6) obtained in the previous step 3 with a compound (15).

Pro1 in formula (15) represents an amino-protective group, which is described in literature (for example, *Protective Groups in Organic Synthesis*, written by T. W. Green, 2nd Ed., by John Wiley & Sons, 1991). For example, it includes a Boc group, an acetyl group, a benzyl group.

The reaction in this step is Mitsunobu reaction, which may be attained according to a method described in literature (for example, "The use of diethyl azodicarboxylate and triphenylphosphine in synthesis and transformation of natural products" written by Mitsunobu. 0 in *Synthesis*, Vol. 1, 1981, pp. 1-28) in the presence of a phosphine compound and an azo compound, or a method similar to it, or a combination of the method with an ordinary method.

The amount of the compound (15) to be used in this step may be generally from 0.5 to 10 equivalents relative to one equivalent of the compound (6), preferably from 1 to 3 equivalents.

The phosphine compound used in this step includes, for example, triphenyl phosphine, triethyl phosphine, tributyl phosphine.

The amount of the phosphine compound used may be generally from 0.5 to 10 equivalents relative to one equivalent of the compound (6), preferably from 1 to 3 equivalents.

The azo compound used includes, for example, diethyl azodicarboxylate, diisopropyl azodicarboxylate.

The amount of the azo compound to be used may be generally from 0.5 to 10 equivalents relative to one equivalent of the compound (6), preferably from 1 to 3 equivalents.

The reaction time may be generally from 1 to 48 hours, preferably from 4 to 12 hours.

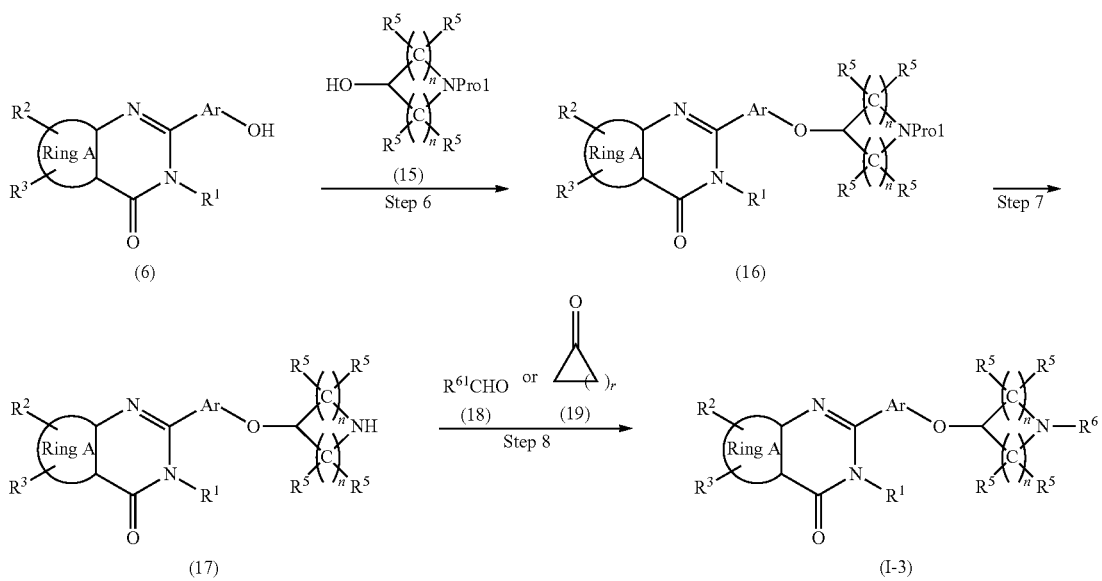

The reaction time may be generally from 0° C. to the boiling point of the solvent, preferably from 15° C. to 30° C.

Not specifically defined, the reaction solvent to be used in this step may be any one not interfering with the reaction. Concretely, for example, it includes tetrahydrofuran, toluene.

The compound (16) may also be produced by reacting a compound (6) with a compound (15-2):

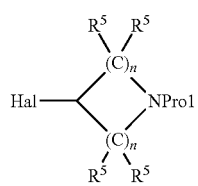

(15-2)

[wherein Hal represents a halogen atom; and the other symbols have the same meanings as above], in the presence of a base.

Hal in formula (15-2) represents a halogen atom, including, for example, a chlorine atom, a bromine atom, an iodine atom. Of those, preferred is a bromine atom.

The amount of the compound (15-2) to be used in this step may be generally from 1 to 5 equivalents relative to one equivalent of the compound (6), preferably from 1 to 2 equivalents.

The compound (15-2) to be used in this step includes, for example, 1-benzyl-4-chloropiperidine, 1-benzyl-4-bromopiperidine, 1-benzyl-4-iodopiperidine, tert-butyl 4-chlorotetrahydro-1(2H)-pyridinecarboxylate, tert-butyl 4-bromotetrahydro-1(2H)-pyridinecarboxylate, tert-butyl 4-iodotetrahydro-1(2H)-pyridinecarboxylate.

The amount of the base to be used in this step may be generally from 1 to 10 equivalents relative to one equivalent of the compound (6), preferably from 1 to 3 equivalents.

The base to be used in this step includes, for example, sodium carbonate, sodium hydrogencarbonate, potassium carbonate, potassium hydrogencarbonate, cesium carbonate, sodium hydride, diisopropylethylamine. Of those, preferred are potassium carbonate, sodium hydride.

Not specifically defined, the reaction solvent may be any one not interfering with the reaction. For example, it includes N,N-dimethylformamide, N,N-dimethylacetamide, acetonitrile, propionitrile, 1,4-dioxane, tetrahydrofuran, dimethoxyethane, and their mixed solvents. Of those, for example, preferred are N,N-dimethylformamide, N,N-dimethylacetamide, tetrahydrofuran.

The reaction time may be generally from 1 hour to 48 hours, preferably from 2 hours to 24 hours.

The reaction time may be generally from −78° C. to 100° C., preferably from 0° C. to 40° C.

Thus obtained, the compound (16) may be isolated and purified through any known separation and purification method of, for example, condensation, reduced-pressure condensation, crystallization, solvent extraction, reprecipitation or chromatography, or not isolated and purified, it may be processed in the next step.

(Step 7)

This step is a method for producing a compound (17) by removing the amino-protective group from the compound (16) obtained in the previous step 6.

The removal of the amino-protective group in this step may be attained according to a method described in literature (for example, *Protective Groups in Organic Synthesis*, written by T. W. Green, 2nd Ed., by John Wiley & Sons, 1991), or a method similar to it, or a combination of the method with an ordinary method.

Thus obtained, the compound (17) may be isolated and purified through any known separation and purification method of, for example, condensation, reduced-pressure condensation, crystallization, solvent extraction, reprecipitation or chromatography, or not isolated and purified, it may be processed in the next step.

(Step 8)

This step is a method for producing a compound (I-3) of the invention by reacting the compound (17) obtained in the previous step 7, with a compound (18) or a compound (19) in the presence of a Broensted acid or a Lewis acid, and a reducing agent.

Concretely, the compound (18) to be used in this step includes, for example, acetaldehyde, propionaldehyde, butylaldehyde.

Concretely, the compound (19) to be used in this step is, for example, [(1-ethoxycyclopropyl)oxy](trimethyl)silane.

The amount of the compound (18) or (19) to be used may be generally from 1 to 10 equivalents relative to one equivalent of the compound (17), preferably from 1 to 3 equivalents.

The amount of the boronation reagent to be used includes, for example, triacetoxyborohydride, sodium cyanoborohydride.

The amount of the hydrogenation reagent to be used may be generally from 1 to 10 equivalent relative to one equivalent of the compound (17), preferably from 1 to 3 equivalents.

The amount of zinc(II) chloride to be used in this step may be generally from 1 to 10 equivalents relative to one equivalent of the compound (17), preferably from 1 to 3 equivalents.

Any other Broensted acid or Lewis acid may be used in place of zinc chloride. For example, acetic acid, trifluoroacetic acid, magnesium chloride, boron trifluoride may also be used in this reaction.

Not specifically defined, the reaction solvent may be any one not interfering with the reaction. For example, it includes methanol, ethanol, acetic acid, tetrahydrofuran, dichloromethane. Of those, preferred are methanol, ethanol.

The reaction time may be generally from 1 hour to 48 hours, preferably from 1 hour to 24 hours.

The reaction temperature may be generally from 0° C. to 100° C., preferably from 0° C. to 40° C.

Thus obtained, the compound (I-3) of the invention may be isolated and purified through any known separation and purification method of, for example, condensation, reduced-pressure condensation, crystallization, solvent extraction, reprecipitation or chromatography.

The compound (I-3) of the invention may also be produced by reacting a compound of the above-mentioned formula (6):

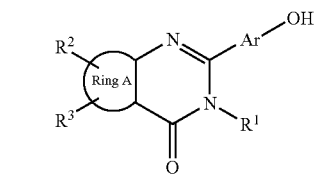

[wherein the symbols have the same meanings as above], with a compound of a formula (20):

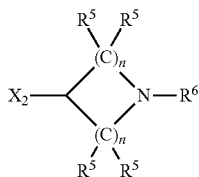

[wherein the symbols have the same meanings as above], in the presence of a base.

The amount of the compound (20) to be used in this step may be generally from 1 to 5 equivalents relative to one equivalent of the compound (6), preferably from 1 to 2 equivalents.

Concretely, the compound (20) to be sued includes, for example, 4-bromo-1-cyclobutylpiperidine, 4-bromo-1-cyclopentylpiperidine, 4-bromo-1-cyclohexylpiperidine.

Not specifically defined, the reaction solvent may be any one not interfering with the reaction. For example, it includes dimethyl sulfoxide, N,N-dimethylformamide, N,N-dimethylacetamide, benzene, xylene, toluene, 1,4-dioxane, tetrahydrofuran, dimethoxyethane, and their mixed solvents. Of those, for example, preferred are dimethyl sulfoxide, N,N-dimethylformamide, tetrahydrofuran.

The reaction time may be generally from 1 hour to 48 hours, preferably from 2 hours to 24 hours.

The reaction time may be generally from −78 C to 100° C., preferably from 0° C. to 40° C.

Thus obtained, the compound (I-3) of the invention may be isolated and purified through any known separation and purification method of, for example, condensation, reduced-pressure condensation, crystallization, solvent extraction, reprecipitation or chromatography.

The compound (I-3) of the invention may also be produced by reacting a compound (3) obtained in the previous step 1 with a compound of the following formula (21):

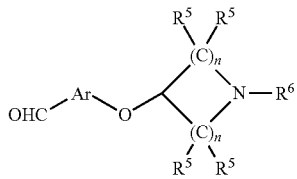

[wherein the symbols have the same meanings as above].

In this step, TsOH (or its hydrate) and DDQ are used.

The amount of TsOH (or its hydrate) to be used in this step may be generally from 0.1 to 10 equivalents relative to one equivalent of the compound (3), preferably from 0.5 to 2 equivalents.

The amount of DDQ to be sued in this step may be generally from 1 to 10 equivalents relative to one equivalent of the compound (3), preferably from 1 to 3 equivalents.

In this step, acetic acid or fumaric acid may also be used in place of TsOH; and manganese oxide may also be sued in place of DDQ.

The amount of the compound (21) to be used in this step may be generally from 1 to 5 equivalents relative to one equivalent of the compound (3), preferably from 1 to 3 equivalents.

The compound (21) to be sued includes, for example, 4-[(1-cyclobutyl-4-piperidinyl)oxy]benzaldehyde, 4-[(1-cyclopentyl-4-piperidinyl)oxy]benzaldehyde, 4-[(1-cyclohexyl-4-piperidinyl)oxy]benzaldehyde.

Not specifically defined, the reaction solvent may be any one not interfering with the reaction. For example, it includes dimethyl sulfoxide, N,N-dimethylformamide, N,N-dimethylacetamide, acetonitrile, propionitrile, benzene, xylene, toluene, 1,4-dioxane, tetrahydrofuran, dimethoxyethane, and their mixed solvents. Of those, preferred are toluene and 1,4-dioxane.

The reaction time may be generally from 1 hour to 96 hours, preferably from 3 hours to 24 hours.

The reaction time may be generally from 0° C. to 150° C., preferably from 60° C. to 120° C.

Thus obtained, the compound (I-3) of the invention may be isolated and purified through any known separation and purification method of, for example, condensation, reduced-pressure condensation, crystallization, solvent extraction, reprecipitation or chromatography.

Of the compound (21):

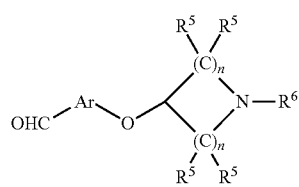

to be used in this step, a compound (21-1):

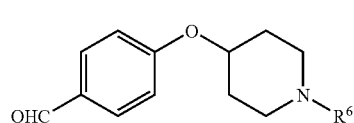

[wherein the symbols have the same meanings as above] may be produced, for example, according to the following method:

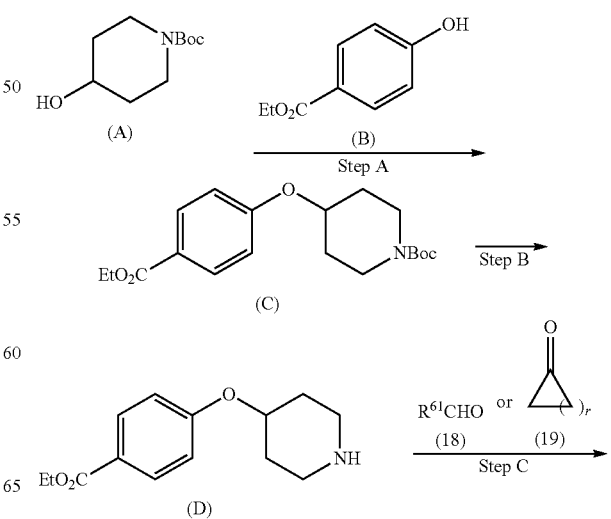

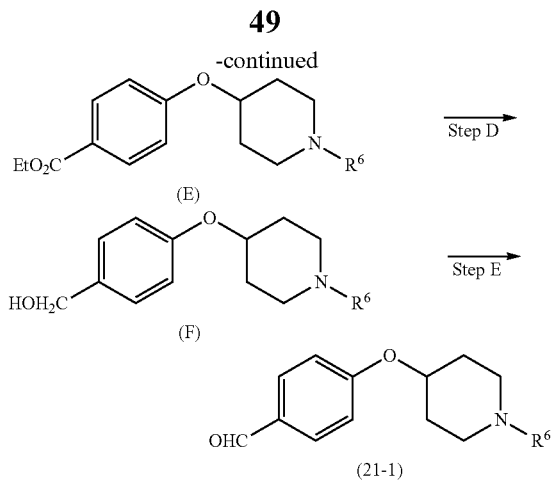

[wherein the symbols heave the same meanings as above.]

(Step A)

This step is a method for producing a compound (C) by reacting 1-Boc-4-piperidinol (A) and ethyl 4-hydroxybenzoate (B) through Mitsunobu reaction as in the above-mentioned step 6.

The amount of the compound (A) to be used in this step may be generally from 0.5 to 10 equivalents relative to one equivalent of the compound (B), preferably from 1 to 3 equivalents.

The phosphine compound to be used in this step includes, for example, triphenyl phosphine, triethyl phosphine, tributyl phosphine.

The amount of the phosphine compound to be used may be generally from 0.5 to 10 equivalents relative to one equivalent of the compound (B), preferably from 1 to 3 equivalents.

The azo compound to be used includes, for example, diethyl azodicarboxylate, diisopropyl azodicarboxylate.

The amount of the azo compound to be used may be generally from 0.5 to 10 equivalents relative to one equivalent of the compound (B), preferably from 1 to 3 equivalents.

The reaction temperature may be generally from −78° C. to the boiling point of the solvent, preferably from 15° C. to 30° C.

The reaction time may be generally from 1 to 48 hours, preferably from 4 to 12 hours.

Not specifically defined, the reaction solvent to be used in this step may be any one not interfering with the reaction. For example, it includes tetrahydrofuran, toluene.

Thus obtained, the compound (C) may be isolated and purified through any known separation and purification method of, for example, condensation, reduced-pressure condensation, crystallization, solvent extraction, reprecipitation or chromatography, or not isolated and purified, it may be processed in the next step.

(Step B)

This step is a method for producing a compound (D) by removing the Boc group from the compound (C).

The removal of the Boc group in this step may be attained according to a method described in literature (for example, Protective Groups in Organic Synthesis, written by T. W. Green, 2nd Ed., by John Wiley & Sons, 1991), or a method similar to it, or a combination of the method with an ordinary method.

For removing the Boc group, for example, trifluoroacetic acid may be used. The compound (C) may be reacted with trifluoroacetic acid, and the reaction may be attained in a reaction solvent.

Thus obtained, the compound (D) may be isolated and purified through any known separation and purification method of, for example, condensation, reduced-pressure condensation, crystallization, solvent extraction, reprecipitation or chromatography, or not isolated and purified, it may be processed in the next step.

(Step C)

This step is a method for producing a compound (E) by reacting the compound (D) with the above-mentioned compound (18) or (19).

The reaction in this method may be attained according the method of the previous step 8, or a method similar to it, or a combination of the method with an ordinary method.

Thus obtained, the compound (E) may be isolated and purified through any known separation and purification method of, for example, condensation, reduced-pressure condensation, crystallization, solvent extraction, reprecipitation or chromatography, or not isolated and purified, it may be processed in the next step.

(Step D)

This step is a method for producing a compound (F) by reducing the compound (E).

The reducing agent to be used in this step includes, for example, diisobutylaluminium hydride, lithiumaluminium hydride.

The amount of the reducing agent to be used may be generally from 1 to 20 equivalents relative to one equivalent of the compound (E), preferably from 1 to 3 equivalents.

The reaction temperature may be generally from −78° C. to 80° C., preferably from 0° C. to room temperature.

The reaction time may be generally from 0.1 to 24 hours, preferably from 0.1 to 3 hours.

Not specifically defined, the reaction solvent may be any one not interfering with the reaction. For example, it includes toluene, diethyl ether, dichloromethane, tetrahydrofuran, and their mixed solvents.

Thus obtained, the compound (F) may be isolated and purified through any known separation and purification method of, for example, condensation, reduced-pressure condensation, crystallization, solvent extraction, reprecipitation or chromatography, or not isolated and purified, it may be processed in the next step.

(Step E)

This step is a method for producing a compound (21-1) by oxidizing the compound (F).

The oxidizing agent to be used in this step includes manganese dioxide ($MnO_2$), pyridinium chlorochromate (PCC), pyridinium dichromate (PDC).

The amount of the oxidizing agent to be used may be, for example, form 1 to 50 equivalents, preferably from 1 to 20 equivalents.

The reaction temperature may be generally from 0° C. to 60° C., preferably from 15 to 40° C.

The reaction time may be generally from 1 to 48 hours, preferably from 1 to 24 hours.

Not specifically defined, the reaction solvent to be used in this step may be any one not interfering with the reaction. For example, it includes tetrahydrofuran, dichloromethane, chloroform, ethyl acetate.

A compound of a formula (I-4) of the invention:

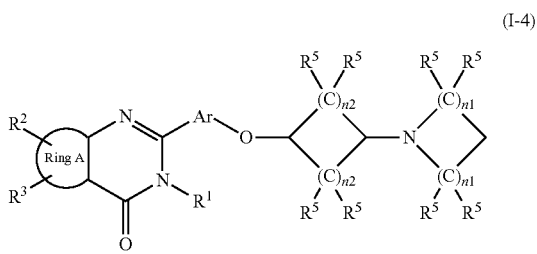

(I-4)

[wherein the symbols have the same meanings as above], may be produced, for example, according to the following method:

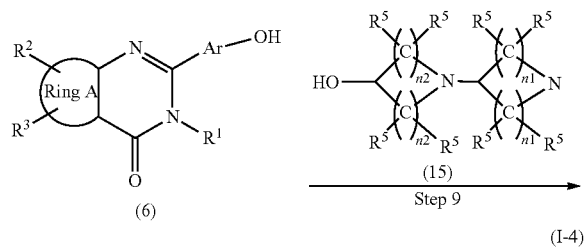

(Step 9)

This step is a method for producing a compound (14) of the invention by reacting a compound (6) obtained in the previous step 3 with a compound (22). This reaction is Mitsunobu reaction, which may be attained according to a method described in literature (for example, "The use of diethyl azodicarboxylate and triphenylphosphine in synthesis and transformation of natural products" written by Mitsunobu. O in *Synthesis*, Vol. 1, 1981, pp. 1-28) in the presence of a phosphine compound and an azo compound, or a method similar to it, or a combination of the method with an ordinary method.

The compound (22) to be used in this step includes, for example, 4-(1-pyrrolidinyl)cyclohexanol, 4-(1-piperidinyl) cyclohexanol, 4-(1-azetanyl)cyclohexanol.

The amount of the compound to be used in this step, the reaction temperature and other reaction conditions may be similar to those in the previous step 6.

The compound of formula (I-4) may also be produced by reacting the compound (6) with a compound of a formula (23):

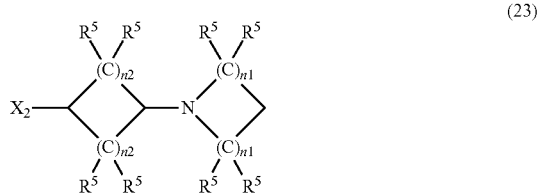

(23)

[wherein the symbols have the same meanings as above].

This reaction may be attained under reaction conditions similar to those for the reaction of the compound (6) with the compound (11) or (12) mentioned above.

The compound (23) to be used in this step includes, for example, 1-(4-bromocyclohexyl)pyrrolidine, 1-(4-bromocyclohexyl)piperidine, 1-(4-bromocyclopropyl)pyrrolidine, 1-(4-bromocyclopropyl)piperidine.

Thus obtained, the compound (14) may be isolated and purified through any known separation and purification method of, for example, condensation, reduced-pressure condensation, solvent extraction, crystallization, reprecipitation or chromatography.

Compounds of formulae (I-1), (I-2), (I-3) and (I-4) are all within the scope of formula (I).

The substituent on the ring A in formulae (I), (I-1), (I-2), (I-3) and (I-4) in the invention may be converted into any other substituent according to a method described in literature (*Comprehensive Organic Synthesis*, Vol. 6, Pergamon Press, 1991; *Comprehensive Organic Transformations*, Richard L., et al., VCH Publishers, 1988), or a method similar to it, or a combination of the method with an ordinary method.

When the compound (I), (I-1), (I-2), (I-3) or (I-4) of the invention has a nitro group on its ring A, then the nitro group may be converted into an amino group, for example, through catalytic reduction in a hydrogen atmosphere in the presence of Pd-carbon. The amount of Pd-carbon to be used in this step may be generally from 0.01 to 1 equivalent relative to one equivalent of the compound (I), (I-1), (I-2), (I-3) or (I-4), preferably from 0.1 to 0.5 equivalents.

Not specifically defined, the reaction solvent may be any one not interfering with the reaction. For example, it includes dimethylsulfoxide, N,N-dimethylformamide, N,N-dimethylacetamide, ethyl acetate, methyl acetate, acetonitrile, propionitrile, benzene, xylene, toluene, 1,4-dioxane, tetrahydrofuran, dimethoxyethane, and their mixed solvents. Of those, for example, preferred are methanol, ethanol, ethyl acetate.

The reaction time may be generally from 1 hour to 96 hours, preferably from 1 hour to 24 hours.

The reaction temperature may be generally from 0° C. to 100° C., preferably from room temperature to 60° C.

Thus obtained, the amino compound of the invention may be isolated and purified through any known separation and purification method of, for example, condensation, reduced-pressure condensation, crystallization, solvent extraction, reprecipitation or chromatography, or not isolated and purified, it may be processed in the next step.

In the compound of the invention having an amino group on its ring A, the amino group may be converted into a lower sulfonylamino group, an arylsulfonylamino group, an aryloxycarbonylamino group, an arylalkyloxycarbonylamino group, a lower alkyloxycarbonylamino group, an alkylcarbonylamino group, an arylcarbonylamino group, a hetero-arylcarbonylamino group, an arylalkylcarbonylamino group or a hetero arylalkylcarbonylamino group.

In the compound (I), (I-1), (I-2), (I-3) or (I-4) of the invention having an amino group in its ring A, the amino group may be converted into a lower alkylsulfonylamino group, for example, by reacting the compound with a lower alkylsulfonyl chloride in the presence of a base; or the amino group may be converted into a lower alkylcarbonylamino group, for example, by reacting the compound with an acyl halide.

The amount of the base to be used may be generally from 1 to 10 equivalent relative to one equivalent of the compound (I), (I-1), (I-2), (I-3) or (I-4), preferably from 1 to 5 equivalents.

The base to be used includes, for example, triethylamine, N,N-diisopropylethylamine, pyridine, 1,8-diazabicyclo [5.4.0]undec-7-ene, pyrrolidine, piperidine. Of those, preferred are triethylamine, pyridine, N,N-diisopropylethylamine.

The lower alkylsulfonyl chloride to be used includes, for example, methanesulfonyl chloride, ethanesulfonyl chloride.

The acyl halide to be used is, for example, acyl chloride.

Not specifically defined, the reaction solvent may be any one not interfering with the reaction. For example, it includes methylene chloride, chloroform, 1,2-dichloroethane, dimethylsulfoxide, N,N-dimethylformamide, N,N-diethylacetamide, ethyl acetate, methyl acetate, acetonitrile, propionitrile, benzene, xylene, toluene, 1,4-dioxane, tetrahydrofuran, dimethoxyethane, and their mixed solvents. Of those, preferred are tetrahydrofuran, methylene chloride, chloroform.

The reaction time may be generally from 1 hour to 24 hours, preferably from 1 hour to 12 hours.

The reaction temperature may be generally from −78° C. to 60° C., preferably from 0° C. to room temperature.

In case where the formula (I), (I-1), (I-2), (I-3) or (I-4) in the invention has a halogen atom such as a bromine atom on the ring A thereof, then, the halogen atom on the ring A may be converted into an aryl group or a heteroaryl group through Suzuki reaction or Heck reaction. The conversion may be attained according to a method described in literature (for example, *Comprehensive Organic Synthesis*, Vol. 6, Pergamon Press, 1991, *Comprehensive Organic Transformations*, Richard L. et al., VCH Publishers, 1988), or a method similar to it, or a combination of the method with an ordinary method.

Suzuki reaction to convert the halogen atom on the ring A into a phenyl group with $PhB(OH)_2$ may be attained, for example, according to the following method.

The amount of $PhB(OH)_2$ to be used in this step may be generally from 1 to 10 equivalents relative to one equivalent of the compound (I), (I-1), (I-2), (I-3) or (I-4) having a halogen atom such as a bromine atom on its ring A, preferably from 1 to 3 equivalents.

The catalyst to be used includes, for example, $Pd(PPh_3)_4$, $Pd_2(dba)_3$, $PdCl_2(dppf)_2$. Of those, preferred are $Pd(PPh_3)_4$ $PdCl_2(dppf)_2$.

The amount of the catalyst to be sued may be generally from 1 to 200 mol % relative to one equivalent of the compound (I), (I-1), (I-2), (I-3) or (I-4), preferably from 5 to 20 mol %. The base to be used includes, for example, sodium carbonate, potassium carbonate, cesium carbonate, sodium acetate, potassium phosphate, triethylamine, N,N-diisopropylethylamine. Of those, preferred are sodium carbonate, potassium carbonate.

The amount of the base to be used may be generally from 1 to 20 equivalents relative to one equivalent of the compound (I), (I-1), (I-2), (I-3) or (I-4), preferably from 2 to 10 equivalents.

Not specifically defined, the reaction solvent may be any one not interfering with the reaction. For example, it includes toluene, DMF, NMP, dioxane, THF, DMSO, water, and their mixed solvents. Of those, preferred are toluene, DMF, NMP, water, water/toluene mixed solvent.

The reaction temperature may be generally from 0 to 150° C., preferably from 50 to 120° C.

The reaction time may be generally from 30 minutes to 7 days, preferably from 6 to 12 hours.

The compounds of formula (I), (I-1), (I-2), (I-3) or (I-4) of the invention may be readily isolated and purified in any ordinary separation and purification method. The method includes, for example, solvent extraction, recrystallization, reprecipitation, column chromatography, preparative thin-layer chromatography.

These compounds may be converted into pharmaceutically-acceptable salts or esters in any ordinary manner; and on the contrary, such salts or esters may be converted into the corresponding free compounds in any ordinary manner.

The acid addition salts include, for example, hydrohalides (e.g., hydrochlorides, hydrofluorides, hydrobromides, hydroiodides), inorganic acid salts (e.g., nitrates, perchlorates, sulfates, phosphates, carbonates), lower alkylsulfonates (e.g., methanesulfonates, trifluoromethanesulfonates, ethanesulfonates), arylsulfonates (e.g., benzenesulfonates, p-toluenesulfonates), organic acid salts (e.g., fumarates, succinates, citrates, tartrates, oxalates, maleates), and amino acid salts (e.g., glutamates, aspartates).

The base addition salts include, for example, alkali metal salts (e.g., sodium salts, potassium salts), alkaline earth metal salts (e.g., calcium salts, magnesium salts), ammonium salts, and organic base (e.g., guanidine, triethylamine, dicyclohexylamine) addition salts. Further, the compounds of the invention may be in any form of hydrates or solvates of their free compounds or salts.

The compounds of formula (I) and their pharmaceutically-acceptable salts may be administered orally or parenterally.

In clinical use of the compounds of the invention, pharmaceutically-acceptable additives may be added thereto to formulate various preparations in accordance with the intended administration route thereof. Various additives generally used in the field of pharmaceutical compositions may be used herein, including, for example, gelatin, lactose, white sugar, titanium oxide, starch, crystalline cellulose, hydroxypropylmethyl cellulose, carboxymethyl cellulose, corn starch, microcrystalline wax, white petrolatum, magnesium metasilicate aluminate, anhydrous calcium phosphate, citric acid, trisodium citrate, hydroxypropyl cellulose, sorbitol, sorbitan fatty acid ester, polysorbate, sucrose fatty acid ester, polyoxyethylene, hardened castor oil, polyvinylpyrrolidone, magnesium stearate, light silicic acid anhydride, talc, vegetable oil, benzyl alcohol, gum arabic, propylene glycol, polyalkylene glycol, cyclodextrin, and hydroxypropylcyclodextrin.

Combined with such additives, the compound of the invention may be formulated into solid preparations (e.g., tablets, capsules, granules, powders and suppositories) and liquid preparations (e.g., syrups, elixirs, injections). These preparations can be produced in any method known in the filed of pharmaceutical compositions. The liquid preparations may be in such a form that is dissolved or suspended in water or in any other suitable medium before use. Especially for injections, the preparation may be dissolved or suspended, if desired, in a physiological saline or glucose solution, and a buffer and a preservative may be added thereto. The preparations may contain the compound of the invention in an amount of from 1.0 to 100% by weight, preferably from 1.0 to 60% by weight of the preparation.

The compounds of the invention may be formulated into preparations, for example, according to the following Formulation Examples.

FORMULATION EXAMPLE 1

10 parts of the compound of Example 1 to be described hereinunder, 15 parts of heavy magnesium oxide and 75 parts of lactose are uniformly mixed to prepare a powdery or granular preparation having a particle size of at most 350 µm. The preparation is encapsulated to give capsules.

FORMULATION EXAMPLE 2

45 parts of the compound of Example 1 to be described hereinunder, 15 parts of starch, 16 parts of lactose, 21 parts of crystalline cellulose, 3 parts of polyvinyl alcohol and 30 parts of distilled water are uniformly mixed, then ground, granulated and dried, and then sieved to give a granular preparation having a particle diameter of from 1410 to 177 µm.

FORMULATION EXAMPLE 3

A granular preparation is prepared in the same manner as in Formulation Example 2. 96 parts of the granular preparation is mixed with 3 parts of calcium stearate, and shaped under compression into tablets having a diameter of 10 mm.

FORMULATION EXAMPLE 4

90 parts of the granular preparation obtained according to the method of Formulation Example 2 is mixed with 10 parts of crystalline cellulose and 3 parts of calcium stearate, and shaped under compression into tablets having a diameter of 8 mm. These are coated with a mixed suspension of syrup gelatin and precipitated calcium carbonate to give sugar-coated tablets.

These preparations may contain any other therapeutically-effective drug, as described below.

In their use, the compounds of the invention may be combined with any other drug effective for treatment (prevention or therapy) of metabolic disorders or dietary disorders. The individual ingredients to be combined may be administered at different times or at the same time, either as one preparation or as divided different preparations. The combination of the compound of the invention with any other drug effective for treatment of metabolic disorders or dietary disorders includes, in principle, combinations thereof with any and every drug effective for treatment of metabolic disorders or dietary disorders.

The compounds of the invention may also be combined with any other drug effective for hypertension, obesity-related hypertension, hypertension-related disorders, cardiomegaly, left ventricle hypertrophy, metabolic disorders, obesity, obesity-related disorders (these are hereinafter referred to as "additional drugs"). Such additional drugs may be administered at the same time or at different times or successively in order in prevention or treatment of the above-mentioned disorders. When the compound of the invention is used simultaneously with one or more additional drugs, then it may be in a pharmaceutical composition for one-dose administration. However, in such combination therapy, the composition containing the compound of the invention and the additional drug may be administered to subjects simultaneously, or separately or successively. The composition and the additional drug may be packed separately. They may be administered at different times.

The dose of the additional drug may depend on the clinical use thereof, and may be suitably determined in accordance with the administration subject, the administration route, the diseases and the combination. The form of the additional drug for administration is not specifically defined, and it may be combined with the compound of the invention when they are administered. The administration mode includes, for example, the following: (1) A compound of the invention is combined with a additional drug to give a single preparation for single administration; (2) a compound of the invention and a additional drug are separately formulated into different two preparations, and the two preparations are simultaneously administered in one administration route; (3) a compound of the invention and a additional drug are separately formulated into different two preparations, and they are administered at different times in one and the same administration route; (4) a compound of the invention and a additional drug are separately formulated into different two preparations, and they are administered at the same time in two different administration routes; (5) a compound of the invention and a additional drug are separately formulated into different two preparations, and they are administered at different times in different administration routes (for example, a compound of the invention and a additional drug are administered in that order, or in an order contrary to this). The blend ratio of the compound of the invention and the additional drug may be suitably determined depending on the administration subject, the administration route, and the disease for the administration.

The additional drugs usable in the invention includes therapeutical drugs for diabetes, therapeutical drugs for hyperlipemia, therapeutical drugs for hypertension, and anti-obesity drugs. Two or more such additional drugs may be combined in any desired ratio.

The therapeutical drugs for diabetes includes, for example, the following:

1) PPAR (peroxisome proliferator-activated receptor)-γ agonists such as glitazones (e.g., ciglitazone, darglitazone, englitazone, isaglitazone, MCC-555, pioglitazone, rosiglitazone, troglitazone, BRL49653, CLX-0921, 5-BTZD), GW-0207, LG-100641, LY-300512;
2) biguanides such as metformin, buformin, phenformin;
3) protein tyrosine phosphatase 1B inhibitors;
4) sulfonylureas such as acetohexamide, chloropropamide, diabinese, glibenclamide, glipizide, glyburide, glimepiride, glicilazide, glipentide, gliquidone, glisolamide, trazamide, tolubutamide;
5) meglitinides such as repaglinide, nateglinide;
6) α-glucoside hydrolase inhibitors such as acarbose, adiposine, camiglibose, emiglitate, miglitol, voglibose, pradimicin-Q, salbostatin, CKD-711, MDL-25,673, MDL-73,945, MOR14;
7) α-amylase inhibitors such as tendamistat, trestatin, A13688;
8) insulin secretion promoters such as linogliride, A4166;
9) fatty acid oxidation inhibitors such as clomoxir, etomoxir;
10) A2 antagonists such as midaglizole, isaglidole, deriglidole, idazoxan, earoxan, fluparoxan;
11) insulin or insulin mimetics such as biota, LP-100, novalapid, insulin determir, insulin lispro, insulin glargine, insulin zinc, Lys-Pro-insulin, GLP-1 (73-7), GLP1 (7-36)-$NH_2$;
12) non-thiazolidinediones such as JT-501, farglitazar;
13) PPARα/γ dual-agonists such as CLX-0940, GW-1536, GW-1929, GW-2433, KRP-297, L-796449, LR-90, SB219994;
14) other insulin sensitizes, and
15) VPAC2 receptor agonists.

The therapeutical drugs for hyperlipemia include, for example, the following:

1) bile acid absorption promoters such as cholesterylamine, colesevelem, colestipol, crosslinked dextran dialkylaminoalkyl derivatives, Colestid®, LoCholest®, Questran®;
2) HMG-CoA reductase inhibitors such as atorvastatin, itavastatin, fluvastatin, lovastatin, pravastatin, rivastatin, rosuvastatin, simvastatin, ZD-4522;
3) HMG-CoA synthase inhibitors;
4) cholesterol absorption inhibitors such as snatol ester, β-sitosterol, sterol glucoside, ezetimibe;
5) ACAT (acyl-CoA.cholesterol acyltransacylase) inhibitors such as avasimibe, eflucimibe, KY-505, SMP-709;
6) CETP inhibitors such as JTT705, torcetrapib, CP532632, BAY-63-2149, SC-591, SC-795;
7) squalane synthesis inhibitors;
8) antioxidants such as probucol;
9) PPARα: agonists such as beclofibrate, benzafibrate, ciprofibrate, clofibrate, etofibrate, fenofibrate, gemcabene, gemfibrozil, GW-7647, BM-170744, LY-518674, fibric acid derivatives (e.g., Atromid®, Lopid®, Tricor®);
10) FXR receptor antagonists such as GW-4064, SR-103912;
11) LXR receptor agonists such as GW-3965, T9013137, XTCO-179628;
12) lipoprotein synthesis inhibitors such as niacin;
13) renin-angiotensin system inhibitors;
14) PPARδ partial agonists;
15) bile acid resorption inhibitors such as BARA1453, SC435, PHA384640, S-435, AZD7706;
16) PPARδ agonists such as GW501516, GW590735;
17) triglyceride synthesis inhibitors;
18) MTTP (microsomic triglyceride transportation) inhibitors such as inplitapide, LAB687, CP346086;
19) transcription modifying factors;
20) squalane epoxidase inhibitors;
21) LDL (low-density lipoprotein) receptor derivatives,
22) platelet agglutination inhibitors;
23) 5-LO (5-lipoxygenase)/FLAP (5-lipoxygenase activated protein) inhibitors; and
24) niacin receptor agonists.

The therapeutical drugs for hypertension include, for example, the following:
1) thiazide diuretics such as chlorothialidon, chlorothiazide, dichlorofenamide, hydrofluorothiazide, indapamide, hydrochlorothiazide; loop diuretics such as bumetanide, ethacrynic acid, flosemide, tolusemide; sodium diuretics such as amyloride, triamuteren; aldosterone antagonist diuretics such as spironolactone, epilenone;
2) β-adrenaline blockers such as acebutolol, atenolol, betaxolol, bevantolol, bisoprolol, bopindolol, carteolol, carvedilol, celiprolol, esmolol, indenolol, metaprolol, nadolol, nebivolol, penbutolol, pindolol, propanolol, sotalol, tartatolol, tilisolol, timolol;
3) calcium channel blockers such as amlodipine, aranidipine, azelnidipine, barnidipine, benidipine, bepridil, cinaldipine, clevidipine, diltiazem, efonidipine, felodipine, gallopamil, isradipine, lacidipine, lemildipine, lercanidipine, nicardipine, nifedipine, nilvadipine, nimodepine, nisoldipine, nitrendipine, manidipine, pranidipine, verapamil;
4) angiotensin transferase inhibitors such as benazepril, captopril, cilazapril, delapril, enalapril, fosinopril, imidapril, rosinopril, moexipril, quinapril, quinaprilat, ramipril, perindopril, perindoropril, quanipril, spirapril, tenocapril, transolapril, zofenopril;
5) neutral endopeptidase inhibitors such as omapatrilat, cadoxatril, ecadotril, fosidotril, sampatrilat, AVE7688, ER4030;
6) endotherine antagonists such as tezosentan, A308165, YM62899;
7) vasodilators such as hydraladine, clonidine, minoxidil, nicotinyl alcohol;
8) angiotensin II receptor antagonists such as candesartan, eporsartan, iribesartan, losartan, pratosartan, tasosartan, telmisartan, valsartan, EXP-3137, F16828K, RNH6270;
9) α/β adrenalin blockers such as nipradilol, arotinolol, amoslalol;
10) α1 blockers such as terazosin, urapidil, purazosin, bunazosin, trimazosin, doxazosin, naphthopidil, indolamin, WHIP164, XEN010;
11) α2 agonists such as lofexidine, tiamenidine, moxonidine, rilmenidine, guanobenz; and
12) aldosterone inhibitors.

The anti-obesity drugs include, for example, the following:
1) 5HT (serotonin) transporter inhibitors such as paroxetine, fluoxetine, fenfluramine, fluvoxamine, sertraline, imipulamin;
2) NE (norepinephrine) transporter inhibitors such as GW320659, desipramin, talsupramin, nomifensin;
3) CB-1 (cannabinoid-1 receptor) antagonists/inverse-agonists such as limonabant (Sanofi Synthelabo), SR-147778 (Sanofi Synthelabo), BAY-65-2520 (Bayer), SLV-319 (Sorbei), as well as compounds disclosed in U.S. Pat. Nos. 5,532,237, 4,973,587, 5,013,837, 5,081,122, 5,112,820 5,292,736, 5,624,941, 6,028,084, WO96/33159, WO98/33765, WO98/43636, WO98/43635, WO01/09120, WO01/96330, WO98/31227, WO98/41519, WO98/37061, WO00/10967, WO00/10968, WO97/29079, WO99/02499, WO01/58869, WO02/076949, WO01/64632, WO01/64633, WO01/64634, WO03/006007, WO03/007887 and EP-658546;
4) glerin antagonists such as compounds disclosed in WO01/87355, WO02/08250;
5) histamine(H3) antagonists/inverse-agonists such as thioperamide, 3-(1H-imidazol-4-yl)propyl-N-(pentenyl)carbonate, clobenpropit, iodofenpropit, imoproxyfen, GT2395, A331440, compounds disclosed in WO02/15905, O-[3-(1H-imidazol-4-yl)propanol]carbamate, piperazine-containing H3-receptor antagonists (Lazewska, D. et al., Pharmazie, 56: 927-32 (2001)), benzophenone derivatives Sasse, A. et al., Arch. Pharm. (Weinheim) 334: 45-52 (2001)), substituted N-phenylcarbamates (Reidemeister, S. et al., Pharmazie, 55: 83-6 (2000)), proxyfen derivatives (Sasse, A. et al., J. Med. Chem., 43: 3335-43 (2000));
6) MCH-1R (melamine concentrating hormone receptor 1) antagonists such as T-226296 (Takeda), SNP-7941 (Synaptic), other compounds disclosed in WO01/82925, WO01/87834, WO02/051809, WO02/06245, WO02/076929, WO02/076947, WO02/04433, WO02/51809, WO02/083134, WO02/094799, WO03/004027, JP-A 2001-226269;
7) MCH-2R (melamine concentrating hormone receptor 2) agonists/antagonists;
8) NPY1 (neuropeptide Y1) antagonists such as BIBP3226, J-115814, BIBO3304, LY-357897, CP-671906, GI-264879, and other compounds disclosed in U.S. Pat. No. 6,001,836, WO96/14307, WO01/23387, WO99/51600, WO01/85690, WO01/85098, WO01/85173, WO01/89528;
9) NPY5 (neuropeptide Y5) antagonists such as 152804, GW-569180A, GW-594884A, GW-587081X, GW-548118X, FR235,208, FR226928, FR240662, FR252384, 1229U91, GI-264879A, CGP71683A, LY-377897, LY366377, PD-160170, SR-120562A, SR-120819A, JCF-104, H409/22, and other compounds disclosed in U.S. Pat. Nos. 6,140,354, 6,191,160, 6,258,837, 6,313,298 6,337,332, 6,329,395, 340,683, 6,326,375, 6,329,395, 6,337,332, 6,335,345, EP-01010691, EP-01044970, WO97/19682, WO97/20820, WO97/20821, WO97/20822, WO97/20823, WO98/27063, WO00/107409, WO00/185714, WO00/185730, WO00/64880, WO00/68197, WO00/69849, WO01/09120, WO01/14376, WO01/85714, WO1/85730, WO01/07409, WO01/02379, WO01/02379, WO01/23388, WO01/23389, WO01/44201, WO01/62737, WO01/62738, WO01/09120, WO02/20488, WO02/22592, WO02/48152, WO02/49648, WO02/094789, and compounds disclosed in Norman et al., J. Med. Chem., 43:4288-4312 (2000);
10) reptins such as human recombinant reptin (PEG-OB, Hoffman La Roche), recombinant methionylreptin (Amgen);

11) reptin derivatives such as compounds disclosed in U.S. Pat. Nos. 5,552,524, 5,552,523, 5,552,522, 5,521,283, WO96/23513, WO96/23514, WO96/23515, WO96/23516, WO96/23517, 96/23518, WO96/23519, WO96/23520;
12) opioid antagonists such as narmefen (Revex®), 3-methoxynartorexon, naroxon, nartolexon, compounds disclosed in WO00/21509;
13) aurexin antagonists such as SB-334867A, and other compounds disclosed in WO01/96302, WO01/68609, WO02/51232, WO02/51838 and WO03/023561;
14) BRS3 (bonbesin receptor subtype-3) agonists;
15) CCK-A (cholecystokinin A) agonists such as AR-R15849, GI-181771, JMV-180, A-71378, A-71623, SR-146131, and other compounds disclosed in U.S. Pat. No. 5,739,106;
16) CNTF (ciliary neurotrophic factors) such as GI-181771 (Glaxo-Smith Kline), SR146131 (Sanofi Synthelabo), butabindide, PD170,292, PD149164 (Pfizer);
17) CNTF derivatives such as axokine (Regeneron), and other compounds disclosed in WO94/09134, WO98/22128, WO99/43813;
18) GHS (growth hormone secretion receptor) agonists such as NN703, hexarelin, MK-0677, SM-130686, CP-424, 391, L-692,429, L-163,255, and compounds disclosed in U.S. Pat. No. 6,358,951, US Patent Application Nos. 2002/049196, 2002/022637, WO01/56592, WO02/32888;
19) 5HT2c (serotonin receptor-2c) agonists such as BVT933, DPCA37215, IK264, PNU22394, WAY161503, R-1065, YM348, and other compounds disclosed in U.S. Pat. No. 3,914,250, WO02/36596, WO02/48124, WO02/10169, WO01/66548, WO02/44152, WO02/51844, WO02/40456, WO02/40457;
20) Mc3r (melanocortin-3 receptor) agonists;
21) Mc4r (melanocortin-4 receptor) agonists such as CHIR86036 (Chiron), ME-10142, ME-10145 (Melacure), and other compounds disclosed in WO99/64002, WO00/74679, WO01/991752, WO01/74844, WO01/70708, WO01/70337, WO01/91752, WO02/059095, WO02/059107, WO02/059108, WO02/059117, WO02/12166, WO02/11715, WO02/12178, WO02/15909, WO02/068387, WO02/068388, WO02/067869, WO03/007949, WO03/009847;
22) monoamine re-uptake inhibitors such as sibtramin (Meridia®/Reductil®) and its salts, and other derivatives disclosed in U.S. Pat. Nos. 4,746,680, 4,806,570, 5,436,272, US Patent Application No. 2002/0006964, WO01/27068, WO01/62341;
23) serotonin re-uptake inhibitors such as dexfenfluramine, fluoxetine, and other compounds disclosed in U.S. Pat. No. 6,365,633, WO01/27060 and WO01/162341;
24) GLP1 (glucagon-like peptide-1) agonists;
25) topiramate (Topimax®);
26) phytopharm compound 57 (e.g., CP644,673);
27) ACC2 (acetyl CoA carboxylase-2) inhibitors;
28) β3 (adrenalin receptor-3) agonists such as AD9677/TAK677 (Dai-Nippon Pharmaceutical/Takeda Chemical), CL-316,243, SB418790, BRL-37344, L-796568, BMS-196085, BRL-35135A, CGP12177A, BTA-243, W427353, trecadrine, Zeneca D7114, SR59119A, and other compounds disclosed in U.S. Pat. Nos. 5,705,515, 5,451,677, WO01/74782 and WO02/32897;
29) DGAT1 (diacylglycerol acyltransferase-1) inhibitors;
30) DGAT2 (diacylglycerol acyltransferase-2) inhibitors,
31) FAS (fatty acid synthesis) inhibitors such as carulenin, C75;
32) PDE (phosphodiesterase) inhibitors such as theofylline, pentoxifylline zaprinast, sildenafil, amrinone, milrinone, cilostamide, rolipram and cilomilast;
33) thyroid hormone-β agonists such as KB-2611 (KaroBio BMS), and other compounds disclosed in WO02/15845, JP-A 2000-256190;
34) UCP (uncoupling protein)-1, 2, or 3 activators such as phytanic acid, 4-[(E)-2-(5,6,7,8-tetrahydro-5,5,8,8-tetramethyl-2-naphthalenyl-1-propenyl]benzoic acid (TT-NPB), retinoic acid, and other compounds disclosed in WO99/00123;
35) acylestrogens such as oleoylestrone (disclosed in del Mar-Grasa, M. et al., Obesity Research, 9:202-9 (2001)),
36) glucocorticoid antagonists;
37) 11-β HSD1 (11-β-hydroxysteroid dehydrogenase-1) inhibitors such as BVT3498, BVT2733, and other compounds disclosed in WO01/90091, WO01/90090, WO01/90092;
38) SCD1 (stearoyl-CoA desaturase-1) inhibitors;
39) DP-IV (dipeptidyl peptidase-IV) inhibitors such as isoleucine thiazolidine, valine pyrrolidide, NVP-DPP728, AF237, P93/01, TSL225, TMC-2A/2B/2C, FE999011, P9310/K364, VIP0177, SDZ274-444, and other compounds disclosed in WO03/004498, WO03/004496, EP1258476, WO02/083128, WO02/062764, WO03/000250, WO03/002530, WO03/002531, WO03/002553, WO03/002593, WO03/000180, WO03/000181;
40) lipase inhibitors such as tetrahydroliptatin (Orlistat/Xenical®), Triton WR1339, RHC80267, lipstatin, tea saponin, diethylumbelliferyl phosphate, FL-386, WAY-121898, Bay-N-3176, valilactone, esteracin, ebelactone A, ebelactone B, RHC80267, and other compounds disclosed in WO01/77094, U.S. Pat. Nos. 4,598,089, 4,452,813, 5,512,565, 5,391,571, 5,602,151, 4,405,644, 4,189,438 and 4,242,453;
41) fatty acid transporter inhibitors;
42) dicarboxylate transporter inhibitors;
43) glucose transporter inhibitors;
44) phosphate transporter inhibitors;
45) melanocortin agonists such as melanotan II, and other compounds disclosed in WO99/64002 and WO0/746799;
46) melanin concentrating hormone antagonists;
47) galanin antagonists;
48) CCK antagonists;
49) corticotrophin release hormones;
50) PDE3 (phosphodiesterase 3B) agonists.

The compounds of the invention may be combined with one or more of the above-mentioned additional drugs. The combination of the compound of the invention with one or more additional drugs selected from a group consisting of drugs for diabetes and drugs for hyperlipemia is useful for prevention or remedy of metabolic disorders. In particular, a combination of the compound of the invention with a drug for hypertension and an anti-obesity drug along with a drug for diabetes or a drug for hyperlipemia is useful for prevention or remedy of metabolic disorders owing to the synergistic effect thereof.

When the compounds of the invention are used in clinical sites, then the dose and the administration frequency thereof may vary depending on the sex, the age, the body weight and the condition of the patient and on the type and the scope of the treatment of the patient. In oral administration, in general, the dose may be from 0.01 to 100 mg/kg-adult/day, preferably from 0.03 to 1 mg/kg-adult/day, and it may be administered all at a time or may be administered in a few times as divided into a few portions. In parenteral administration, its dose may be from 0.001 to 10 mg/kg-adult/day, preferably from 0.001 to 0.1 mg/kg-adult/day, and it may be administered all at a time or may be administered in a few times as divided into a few portions.

Ordinary physicians, veterinarians and clinicians may readily determine the effective dose necessary for retarding, inhibiting or stopping the development of diseases.

EXAMPLES

The invention is described more concretely with reference to the following Examples, which, however, do not whatsoever restrict the invention.

For the thin-layer chromatography of the compounds in the Examples, used was a plate of Silicagel $60F_{245}$ (Merck); and for detection, used was a UV detector. Wakogel™ C-300 (Wako Pure Chemicals) was used for the column silica gel; and LC-SORB™ SP-B-ODS (Chemco) or YMC-GEL™ ODS-AQ 120-S50 (Yamamura Chemical Laboratories) was for the reversed-phase column silica gel. Mass spectrum was determined according to an electrospray ionization (ESI) process, using QuattroII (Micromass).

In NMR spectrometry, tetramethylsilane was used for the internal standard. Using Gemini-200 (200 MHz; Varian), Gemini-300 (300 MHz; Varian), Mercury 400 (400 MHz; Varian) or Inova 400 (400 MHz; Varian), the sample was analyzed for the total δ value in ppm.

The meanings of the abbreviations in the following Examples are mentioned below.
i-Bu: isobutyl group
n-Bu: n-butyl group
t-Bu: t-butyl group
Me: methyl group
Et: ethyl group
Ph: phenyl group
i-Pr: isopropyl group
n-Pr: n-propyl group
$CDCl_3$: heavy chloroform
$CD_3OD$: heavy methanol
DMSO-d6: heavy dimethylsulfoxide The meanings of the abbreviations in nuclear magnetic resonance spectra are mentioned below.
s: singlet
d: doublet
dd: double-doublet
t: triplet
m: multiplet
br: broad
q: quartet
quint: quintet
sept: septet
J: coupling constant
Hz: hertz Example 1

3,8-Dimethyl-2-[4-(3-piperidin-1-ylpropoxy)phenyl]-4(3H)-quinazolinone (1) Production of 2-amino-N,3-dimethylbenzamide:
3-Methyl-2-aminobenzoic acid (3.43 g, 22.7 mmol) and N,N'-carbonyldiimidazole (4.05 g, 24.9 mmol) were stirred in THF at 40° C. for 3 hours. After cooled to room temperature, methylamine (2.0 M in THF, 22.7 ml) was added thereto, and further stirred for 1 hour at room temperature. The solvent was evaporated off under reduced pressure, and the residue was purified through silica gel column chromatography (chloroform/methanol=9/1) to obtain the intended compound (3.43 g, yield 92%) as a milky white solid.

(2) Production of 2-(4-methoxyphenyl)-3,8-dimethyl-4(3H)-quinazolinone:
2-Amino-N,3-dimethylbenzamide (4.10 g, 25.0 mmol), sodium hydrogensulfite (2.93 g, 27.5 mmol) and para-anisaldehyde (3.4 g, 25 mmol) were mixed in N,N'-dimethylacetamide (20 ml), stirred at 150° C. for 5 hours, then cooled to room temperature, and distilled water (100 ml) was added thereto and stirred at that temperature for 1 hour. The precipitated solid was taken out through filtration, dried, and recrystallized from hot ethanol to obtain the intended compound (3.42 g, 49%) as a white solid.

(3) Production of 2-(4-hydroxyphenyl)-3,8-dimethyl-4(3H)-quinazolinone:
2-(4-Methoxyphenyl)-3,8-dimethyl-4(3H)-quinazolinone (2.02 g, 7.20 mmol) was dissolved in dichloromethane (10 ml), stirred at −78° C., then boron trifluoride (1.0 M in $CH_2Cl_2$, 21.6 ml) was added thereto, gradually heated up to room temperature, and stirred at that temperature for 12 hours. The reaction solution was diluted with ethyl acetate, and with cooling with ice, this was poured into aqueous 1 N sodium hydroxide solution, and extracted with ethyl acetate. The organic layer was washed with 1 N hydrochloric acid and saturated saline water, and dried with magnesium sulfate. The organic layer was concentrated under reduced pressure to obtain the intended compound (1.54 g, 80%) as a pale yellow solid.

(4) Production of 3,8-dimethyl-2-[4-(3-piperidin-1-ylpropoxy)phenyl]-4(3H)-quinazolinone:
2-(4-Hydroxyphenyl)-3,8-dimethyl-4(3H)-quinazolinone (500 mg, 1.88 mmol) was mixed with 1-chloro-3-bromopropane (326 mg, 2.07 mmol) and potassium carbonate (519 mg, 3.76 mmol) in DMF (5 ml), and stirred at 80° C. for 4 hours. After cooled to room temperature, potassium carbonate (519 mg, 3.76 mmol), potassium iodide (312 mg, 1.88 mmol) and piperidine (320 mg, 3.76 mmol) were added to the reaction solution, and further stirred at 80° C. for 12 hours. The reaction solution was diluted with ethyl acetate, then washed with aqueous 1 N sodium hydroxide solution and saturated saline water in that order, and the organic layer was dried with magnesium sulfate. The solvent was evaporated off, and the residue was purified through silica gel column chromatography (chloroform/methanol=5/1) and recrystallized from ethyl acetate to obtain the intended compound (63 mg, 8.6%) as a colorless solid.

$^1$H-NMR (400 MHz, $CDCl_3$) δ: 1.41-1.51 (2H, m), 1.62 (6H, quint, J=5.5 Hz), 2.03 (2H, quint, J=7.4 Hz), 2.38-2.51 (4H, m), 2.53 (2H, t, J=7.8 Hz), 2.61 (3H, s), 3.55 (3H, s), 4.09 (2H, t, J=6.5 Hz), 7.02 (2H, d, J=9.0 Hz), 7.36 (1H, t, J=7.6 Hz), 7.56 (2H, d, J=9.0 Hz), 7.57-7.62 (1H, m), 8.16 (1H, dd, J=0.8, 7.8 Hz)

Compounds of Examples 2 to 14 can be produced according to the method of Example 1 or a method similar to it or a combination of the method with an ordinary method, but starting from the corresponding aminobenzoic acid, hydroxybenzaldehyde or anisaldehyde and amine.

Example 2

3-Methyl-2-[4-(3-piperidin-1-ylpropoxy)phenyl]-4(3H)-quinazolinone

The entitled compound was obtained according to the method of Example 1 but starting from anthranilic acid, methylamine, 4-anisaldehyde, 1-chloro-3-bromopropane and piperidine.

¹H-NMR (400 MHz, CDCl₃) δ: 1.40-1.51 (2H, m), 1.61 (4H, quint, J=5.9 Hz), 2.02 (2H, quint, J=7.4 Hz), 2.38-2.49 (4H, m), 2.51 (2H, t, J=7.6 Hz), 3.53 (3H, s), 4.09 (2H, t, J=6.3 Hz), 7.02 (2H, d, J=8.6 Hz), 7.46-7.50 (1H, m), 7.52 (2H, d, J=8.6 Hz), 7.70-7.79 (2H, m), 8.32 (1H, d, J=8.2 Hz)

Example 3

3-Ethyl-2-[4-(3-piperidin-1-ylpropoxy)phenyl]-4 (3H)-quinazolinone

The entitled compound was obtained according to the method of Example 1 but starting from anthranilic acid, ethylamine, 4-anisaldehyde, 1-chloro-3-bromopropane and piperidine.
¹H-NMR (400 MHz, CDCl₃) δ: 1.22 (3H, t, J=7.6 Hz), 1.40-1.50 (2H, m), 1.56-1.63 (4H, m), 1.98-2.03 (2H, m), 2.39-2.48 (4H, m), 2.49 (2H, t, J=7.2 Hz), 4.04-4.11 (4H, m), 7.00 (2H, d, J=8.4 Hz), 7.43-7.49 (3H, m), 7.69-7.75 (2H, m), 8.30 (1H, d, J=7.6 Hz)

Example 4

3,6-Dimethyl-2-[4-(3-piperidin-1-ylpropoxy)phenyl]-4(3H)-quinazolinone

The entitled compound was obtained according to the method of Example I but starting from 5-methyl-2-aminobenzoic acid, methylamine, 4-anisaldehyde, 1-chloro-3-bromopropane and piperidine.
¹H-NMR (400 MHz, CDCl₃) δ: 1.39-1.51 (2H, m), 1.57-1.63 (4H, m), 1.98-2.05 (2H, m), 2.35-2.47 (4H, m), 2.47-2.51 (2H, m), 2.51 (3H, s), 3.52 (3H, s), 4.08 (2H, t, J=6.5 Hz), 7.01 (2H, d, J=8.6 Hz), 7.50 (2H, d, J=8.6 Hz), 7.56 (1H, dd, J=8.2, 2.0 Hz), 7.63 (1H, d, J=8.2 Hz), 8.11 (1H, d, J=2.0 Hz)

Example 5

3,5-Dimethyl-2-[4-(3-piperidin-1-ylpropoxy)phenyl]-4(3H)-quinazolinone

The entitled compound was obtained according to the method of Example 1 but starting from 6-methyl-2-aminobenzoic acid, methylamine, 4-anisaldehyde, 1-chloro-3-bromopropane and piperidine.
¹H-NMR (400 MHz, CDCl₃) δ: 1.40-1.52 (2H, m), 1.62 (4H, quint, J=5.5 Hz), 2.03 (2H, quint, J=7.0 Hz), 2.40-2.51 (4H, m), 2.49 (5H, t, J=15.7 Hz), 2.92 (3H, s), 3.47 (3H, s), 4.08 (2H, t, J=6.5 Hz), 7.01 (2H, d, J=8.6 Hz), 7.22-7.24 (1H, m), 7.50 (2H, d, J=8.6 Hz), 7.55-7.59 (2H, m)

Example 6

3-Propyl-2-[4-(3-piperidin-1-ylpropoxy)phenyl]-4 (3H)-quinazolinone

The entitled compound was obtained according to the method of Example 1 but starting from anthranilic acid, propylamine, 4-anisaldehyde, 1-chloro-3-bromopropane and piperidine.
¹H-NMR (400 MHz, CDCl₃) δ: 0.78 (3H, t, J=7.4 Hz), 1.50-1.45 (2H, m), 1.55-1.67 (6H, m), 2.02-2.07 (2H, m), 2.44-2.58 (6H, m), 3.96-4.00 (2H, m), 4.09 (2H, t, J=6.5 Hz), 7.01 (2H, d, J=8.6 Hz), 7.46 (2H, d, J=8.6 Hz), 7.46-7.51 (1H, m), 7.71-7.77 (2H, m), 8.32 (1H, dd, J=1.2, 7.8 Hz)

Example 7

3-Benzyl-2-[4-(3-piperidin-1-ylpropoxy)phenyl]-4 (3H)-quinazolinone

The entitled compound was obtained according to the method of Example 1 but starting from anthranilic acid, benzylamine, 4-anisaldehyde, 1-chloro-3-bromopropane and piperidine.
¹H-NMR (400 MHz, CDCl₃) δ: 1.53-1.39 (2H, m), 1.62 (4H, quint., J=5.9 Hz), 2.01 (2H, quint., J=7.0 Hz), 2.35-2.49 (4H, m), 2.52 (2H, t, J=7.2 Hz), 4.04 (2H, t, J=6.3 Hz), 5.30 (2H, s), 6.90 (2H, d, J=8.6 Hz), 6.95-7.01 (2H, m), 7.19-7.26 (3H, m), 7.29 (2H, d, J=8.6 Hz), 7.51 (1H, ddd, J=1.6, 6.3, 7.8 Hz), 7.74-7.80 (2H, m), 8.36 (1H, d, J=8.2 Hz)

Example 8

3-Ethyl-2-[3-(3-piperidin-1-ylpropoxy)phenyl]-4 (3H)-quinazolinone

The entitled compound was obtained according to the method of Example 1 but starting from anthranilic acid, ethylamine, 3-anisaldehyde, 1-chloro-3-bromopropane and piperidine.
¹H-NMR (400 MHz, CDCl₃) δ: 1.24 (3H, t, J=7.0 Hz), 1.50-1.37 (2H, m), 1.60 (4H, quint., J=5.5 Hz), 2.01 (2H, quint., J=7.0 Hz), 2.30-2.47 (4H, m), 2.50 (2H, t, J=7.4 Hz), 4.05 (2H, m), 4.06 (2H, t, J=6.3 Hz), 7.02-7.10 (2H, m), 7.05 (1H, d, J=1.2 Hz), 7.41 (1H, dd, J=7.8, 9.4 Hz), 7.51 (1H, ddd, J=2.0, 6.7, 7.8 Hz), 7.70-7.80 (2H, m), 8.34 (1H, d, J=8.2 Hz)

Example 9

3-Isopropyl-2-[4-(3-piperidin-1-ylpropoxy)phenyl]-4 (3H)-quinazolinone

The entitled compound was obtained according to the method of Example 1 but starting from anthranilic acid, isopropylamine, 4-anisaldehyde, 1-chloro-3-bromopropane and piperidine.
¹H-NMR (400 MHz, CD₃OD) δ: 1.54-1.44 (2H, m), 1.57 (6H, d, J=7.3 Hz), 1.65 (4H, quint., J=5.9 Hz), 2.05 (2H, td, J=5.9, 16.1 Hz), 2.43-2.56 (4H, m), 2.59 (2H, t, J=7.7 Hz), 4.11 (2H, t, J=6.2 Hz), 4.41 (1H, sept., J=7.3 Hz), 7.09 (2H, d, J=8.8 Hz), 7.50-7.54 (1H, m), 7.51 (2H, d, J=8.8 Hz), 7.61 (1H, d, J=8.1 Hz), 7.75-7.81 (1H, m), 8.20 (1H, dd, J=1.5, 8.1 Hz)

Example 10

2-[4-(3-Piperidin-1-ylpropoxy)phenyl]-3-phenyl-4 (3H)-quinazolinone

The entitled compound was obtained according to the method of Example 1 but starting from anthranilic acid, aniline, 4-anisaldehyde, 1-chloro-3-bromopropane and piperidine.
¹H-NMR (400 MHz, CDCl₃) δ: 1.35-1.53 (2H, m), 1.51-1.75 (4H, m), 1.85-2.03 (2H, m), 2.20-2.70 (6H, m), 3.94 (2H, t, J=6.6 Hz), 6.69 (2H, d, J=8.8 Hz), 7.13-7.15 (2H, m), 7.24-7.36 (5H, m), 7.45-7.53 (1H, m), 7.75-7.80 (2H, m), 8.31 (1H, d, J=8.1 Hz)

Example 11

2-[4-(3-Piperidin-1-ylpropoxy)phenyl]-3-(2,2,2-trifluoroethyl)-4(3H)-quinazolinone The entitled compound was obtained according to the method of Example 1 but starting from anthranilic acid, 2,2,2-trifluoroethylamine, 4-anisaldehyde, 1-chloro-3-bromopropane and piperidine.

$^1$H-NMR (400 MHz, CDCl$_3$) δ: 1.40-1.55 (2H, m), 1.53-1.81 (4H, m), 1.97-2.14 (2H, m), 2.36-2.54 (4H, m), 2.51-2.63 (2H, m), 4.08 (2H, t, J=5.9 Hz), 4.84 (2H, q, J=8.1 Hz), 7.01 (2H, d, J=8.8 Hz), 7.42 (2H, d, J=8.8 Hz), 7.52 (1H, dt, J=1.5, 7.3 Hz), 7.72 (1H, d, J=7.3 Hz), 7.78 (1H, dt, J=1.5, 8.1 Hz), 8.31 (1H, d, J=8.1 Hz)

Example 12

3,8-Dimethyl-2-[4-(3-pyrrolidin-1-ylpropoxy)phenyl]-4(3H)-quinazolinone

The entitled compound was obtained according to the method of Example 1 but starting from 2-amino-3-methylbenzoic acid, methylamine, 4-anisaldehyde, 1-chloro-3-bromopropane and pyrrolidine.

$^1$H-NMR (400 MHz, CD$_3$OD) δ: 2.11-2.07 (4H, m), 2.21-2.29 (2H, m), 2.57 (3H, s), 3.30-3.41 (6H, m), 3.50 (3H, d, J=1.5 Hz), 4.20 (2H, t, J=5.9 Hz), 7.10 (2H, d, J=6.6 Hz), 7.39 (1H, t, J=7.7 Hz), 7.62 (2H, d, J=6.6 Hz), 7.63-7.67 (1H, m), 8.06 (1H, d, J=7.3 Hz)

Example 13

2-(2-Methoxy-4-{3-[(3S)-3-methylpiperidin-1-yl]propoxy}phenyl)-3-methylquinazolin-4(3H)-one The entitled compound was obtained according to the method of Example 1 but starting from anthranilic acid, methylamine, 4-hydroxy-2-methoxybenzaldehyde, 1-chloro-3-bromopropane and (3S)-3-methylpiperidine.(R)-mandelate.

$^1$H-NMR (CDCl$_3$) δ: 0.84-0.93 (1H, m), 0.88 (3H, d, J=6.3 Hz), 1.62-1.78 (5H, m), 1.83-1.95 (1H, m), 1.97-2.09 (2H, m), 2.47-2.57 (2H, m), 2.82-2.97 (2H, m), 3.42 (3H, s), 3.80 (3H, s), 4.08 (2H, t, J=6.3 Hz), 6.54 (1H, d, J=2.4 Hz), 6.62 (1H, dd, J=8.8, 2.4 Hz), 7.34 (1H, d, J=8.8 Hz), 7.46-7.52 (1H, m), 7.73-7.75 (2H, m), 8.33 (1H, d, J=7.8 Hz)

Example 14

8-Methoxy-2-(2-methoxy-4-{3-[(3S)-3-methylpiperidin-1-yl]propoxy}phenyl)-3-methylquinazolin-4(3H)-one The entitled compound was obtained according to the method of Example 1 but starting from 2-amino-3-methoxybenzoic acid, methylamine, 4-hydroxy-2-methoxybenzaldehyde, 1-chloro-3-bromopropane and (3S)-3-methylpiperidine-(R)-mandelate.

$^1$H-NMR (CDCl$_3$) δ: 0.82-0.95 (1H, m), 0.88 (3H, d, J=6.3 Hz), 1.61-1.77 (5H, m), 1.82-1.95 (1H, m), 1.96-2.09 (2H, m), 2.46-2.57 (2H, m), 2.83-2.97 (2H, m), 3.41 (3H, s), 3.77 (3H, s), 3.98 (3H, s), 4.06 (2H, t, J=6.3 Hz), 6.49 (1H, d, J=2.4 Hz), 6.59 (1H, dd, J=8.3, 2.4 Hz), 7.18 (1H, dd, J=7.8, 1.5 Hz), 7.38 (1H, d, J=8.3 Hz), 7.42 (1H, t, J=7.8 Hz), 7.91 (1H, dd, J=8.3, 1.5 Hz)

Example 15

3-Methyl-2-[4-(3-piperidin-1-ylpropoxy)phenyl]pyrido[2,3-d]-pyrimidin-4(3H)-one (1) Production of 2-amino-N-methylnicotinamide:

The intended compound was obtained according to the method of Example 1-(1) but using 2-aminonicotinic acid and methylamine.

(2) Production of 3-methyl-2-[4-(3-piperidin-1-ylpropoxy)phenyl]pyrido[2,3-d]-pyrimidin-4(3H)-one:

2-Amino-N-methylnicotinamide (105 mg, 0.69 mmol), 4-(3-piperidin-1-ylpropoxy)benzamide (171 mg, 0.69 mmol) and p-toluenesulfonic acid monohydrate (66 mg, 0.35 mmol) were suspended in toluene (2 mL), and stirred under reflux for 24 hours. After cooled to room temperature, DDQ (157 mg, 0.69 mmol) and THF (2 mL) were added thereto and stirred at room temperature for 5 hours. The reaction solution was diluted with ethyl acetate, then washed with aqueous 1 N sodium hydroxide solution and saturated saline water, and the organic layer was dried with magnesium sulfate. The solvent was evaporated off, and the residue was purified through silica gel column chromatography (chloroform/methanol=3/1) to obtain the intended compound (52.5 mg, 20%) as a colorless solid (m.p. 109-112° C.).

$^1$H-NMR (400 MHz, CD$_3$OD) δ: 1.44-1.55 (2H, m), 1.63 (4H, quint., J=5.6 Hz), 2.00-2.07 (2H, m), 2.36-2.54 (4H, m), 2.56 (2H, t, J=7.7 Hz), 3.54 (3H, s), 4.12 (2H, t, J=5.9 Hz), 7.08 (2H, d, J=8.8 Hz), 7.54 (1H, dd, J=4.4, 8.1 Hz), 7.65 (2H, d, J=8.8 Hz), 8.64 (1H, dd, J=1.5, 8.1 Hz), 8.90 (1H, dd, J=1.5, 4.4 Hz)

Compounds of Examples 16 to 59 can be produced according to the method of Example 15 or a method similar to it or a combination of the method with an ordinary method, but starting from the corresponding aminobenzoic acid, amine and separately prepared aromatic aldehydes such as 4-(3-piperidin-1-ylpropoxy)benzaldehyde, 4-(3-pyrrolidin-1-ylpropoxy)benzaldehyde, 4-[(1-cyclopentyl-4-piperidinyl)oxy]benzaldehyde, 4-[(1-cyclobutyl-4-piperidinyl)oxy]benzaldehyde, 4-[(1-cyclopentylpiperidin-4-yl)oxy]-2-methoxybenzaldehyde, 4-[(1-cyclobutylpiperidin-4-yl)oxy]-2-methoxybenzaldehyde, 6-[(1-cyclobutylpiperidin-4-yl)oxy]nicotinaldehyde, 2-[(1-cyclobutylpiperidin-4-yl)oxy]pyrimidine-5-carbaldehyde, 4-{3-[(3S)-3-methylpiperidin-1-yl]propoxy}benzaldehyde.

Example 16

3-Methyl-2-[4-(3-pyrrolidin-1-ylpropoxy)phenyl]-4(3H)-quinazoline

The intended compound was obtained according to the method of Example 15 but using anthranilic acid, methylamine and 4-(3-pyrrolidin-1-ylpropoxy)benzaldehyde. The obtained compound was further purified through reversed-phase liquid chromatography (acetonitrile-water) to give a colorless solid (m.p. 108.5-109.5° C.).

$^1$H-NMR (400 MHz, CD$_3$OD) δ: 1.88-1.80 (4H, m), 2.03-2.09 (2H, m), 2.61-2.63 (4H, m), 2.71 (2H, t, J=7.7 Hz), 3.49 (3H, s), 4.13 (2H, t, J=6.2 Hz), 7.09 (2H, d, J=8.8 Hz), 7.51-7.55 (1H, m), 7.58 (2H, d, J=8.8 Hz), 7.66 (1H, d, J=8.1 Hz), 7.80 (1H, t, J=7.7 Hz), 8.23 (1H, d, J=8.1 Hz)

Example 17

3-Methyl-2-[4-(1-cyclopentyl-4-piperidinyloxy)phenyl]-4(3H)-quinazoline

The entitled compound was obtained according to the method of Example 15 but starting from anthranilic acid, methylamine and 4-[(1-cyclopentyl-4-piperidinyl)oxy]benzaldehyde.

$^1$H-NMR (400 MHz, CDCl$_3$) δ: 1.48-1.37 (2H, m), 1.51-1.60 (2H, m), 1.66-1.75 (2H, m), 1.84-1.92 (4H, m), 2.01-2.08 (2H, m), 2.31-2.43 (2H, m), 2.53 (1H, quint., J=8.1 Hz), 2.78-2.84 (2H, m), 3.53 (3H, s), 4.40 (1H, q, J=3.7 Hz), 7.01 (2H, d, J=8.8 Hz), 7.44-7.48 (1H, m), 7.49 (2H, d, J=8.8 Hz), 7.69-7.75 (2H, m), 8.30 (1H, d, J=7.3 Hz)

Example 18

6-Chloro-3-methyl-2-[4-(3-piperidin-1-ylpropoxy)-phenyl]pyrido[3,4-d]-pyrimidin-4(3H)-one The entitled compound was obtained according to the method of Example 15 but starting from 5-amino-2-chloroisonicotinic acid, methylamine and 4-(3-piperidin-1-ylpropoxy)benzaldehyde.

$^1$H-NMR (400 MHz, CDCl$_3$) δ: 1.49-1.42 (2H, m), 1.57-1.64 (4H, m), 1.98-2.06 (2H, m), 2.38-2.44 (4H, m), 2.48 (2H, t, J=7.3 Hz), 3.55 (3H, s), 4.08 (2H, t, J=6.2 Hz), 7.02 (2H, d, J=8.8 Hz), 7.51 (2H, d, J=8.8 Hz), 8.08 (1H, s), 8.92 (1H, s)

Example 19

3,7-Dimethyl-2-[4-(3-piperidin-1-ylpropoxy)phenyl]-4(3H)-quinazolinone

The entitled compound was obtained according to the method of Example 15 but starting from 2-amino-4-methylbenzoic acid, methylamine and 4-(3-piperidin-1-ylpropoxy)benzaldehyde.

$^1$H-NMR (400 MHz, CDCl$_3$) δ: 1.48-1.42 (2H, m), 1.57-1.62 (4H, m), 2.01 (2H, q, J=7.3 Hz), 2.39-2.45 (4H, m), 2.47-2.52 (2H, m), 2.49 (3H, s), 3.50 (3H, s), 4.07 (2H, t, J=6.6 Hz), 7.00 (2H, d, J=8.8 Hz), 7.28 (1H, d, J=8.1 Hz), 7.48 (2H, d, J=8.8 Hz), 7.50 (1H, s), 8.17 (1H, d, J=8.1 Hz)

Example 20

3-Methyl-2-[4-(3-pyrrolidin-1-ylpropoxy)-phenyl]pyrido[2,3-d]-pyrimidin-4(3H)-one The entitled compound was obtained according to the method of Example 15 but starting from 2-aminonicotinic acid, methylamine and 4-(3-pyrrolidin-1-ylpropoxy)benzaldehyde.

$^1$H-NMR (400 MHz, CD$_3$OD) δ: 1.90-1.87 (4H, m), 2.06-2.13 (2H, m), 2.72-2.75 (4H, m), 2.82 (2H, t, J=7.8 Hz), 3.54 (3H, s), 4.15 (2H, t, J=6.3 Hz), 7.11 (2H, d, J=9.0 Hz), 7.56 (1H, dd, J=4.7, 8.2 Hz), 7.67 (2H, d, J=9.0 Hz), 8.65 (1H, dd, J=7.8, 2.0 Hz), 8.93 (1H, dd, J=2.0, 4.7 Hz)

Example 21

2-[4-(1-Cyclopentyl-4-piperidinyloxy)phenyl]-3-methylpyrido[2,3-d]-pyrimidin-4(3H)-one The entitled compound was obtained according to the method of Example 15 but starting from 2-aminonicotinic acid, methylamine and 4-[(1-cyclopentyl-4-piperidinyl)oxy]benzaldehyde. The obtained compound was recrystallized from diethyl ether to give a pale yellow acicular crystal (m.p. 175.0-177.2° C.).

$^1$H-NMR (400 MHz, CD$_3$OD) δ: 1.49-1.40 (2H, m), 1.55-1.64 (2H, m), 1.68-1.77 (2H, m), 1.80-1.98 (4H, m), 2.05-2.12 (2H, m), 2.42-2.51 (2H, m), 2.57-2.65 (1H, m), 2.83-2.92 (2H, m), 3.55 (3H, s), 4.53-4.60 (1H, m), 7.12 (2H, d, J=9.0 Hz), 7.57 (1H, dd, J=7.8, 4.7 Hz), 7.67 (2H, d, J=8.6 Hz), 8.66 (1H, dd, J=2.0, 7.8 Hz), 8.93 (1H, dd, J=2.0, 4.7 Hz)

Example 22

2-[4-(1-Cyclobutyl-4-piperidinyloxy)phenyl]-3-methylpyrido[2,3-d]-pyrimidin-4(3H)-one The entitled compound was obtained according to the method of Example 15 but starting from 2-aminonicotinic acid, methylamine and 4-[(1-cyclobutyl-4-piperidinyl)oxy]benzaldehyde. The obtained compound was recrystallized from diethyl ether to give a colorless solid (m.p. 146.0-150.0° C.).

$^1$H-NMR (400 MHz, CD$_3$OD) δ: 1.72-1.77 (2H, m), 1.81-1.88 (2H, m), 1.90-1.95 (2H, m), 2.04-2.13 (4H, m), 2.25-2.32 (2H, m), 2.64-2.73 (2H, m), 2.79-2.86 (1H, m), 3.55 (3H, s), 4.54-4.59 (1H, m), 7.12 (2H, d, J=8.6 Hz), 7.57 (1H, dd, J=4.3, 8.2 Hz), 7.67 (2H, d, J=8.6 Hz), 8.66 (1H, dd, J=8.0, 1.8 Hz), 8.93 (1H, dd, J=2.0, 4.7 Hz)

Example 23

2-[4-(1-Cyclobutyl-4-piperidinyloxy)phenyl]-3-(2-methoxyethyl)pyrido[2,3-d]pyrimidin-4(3H)-one The entitled compound was obtained according to the method of Example 15 but starting from 2-aminonicotinic acid, 2-methoxyethylamine and 4-[(1-cyclobutyl-4-piperidinyl)oxy]benzaldehyde.

$^1$H-NMR (400 MHz, CDCl$_3$) δ: 1.75-1.65 (2H, m), 1.82-1.94 (4H, m), 1.99-2.09 (4H, m), 2.13-2.23 (2H, m), 2.59-2.68 (2H, m), 2.71-2.79 (1H, m), 3.18 (3H, d, J=1.2 Hz), 3.60 (2H, t, J=5.3 Hz), 4.36 (2H, t, J=5.7 Hz), 4.38-4.45 (1H, m), 6.99 (2H, d, J=7.8 Hz), 7.43 (1H, ddd, J=1.2, 4.3, 7.8 Hz), 7.58 (2H, d, J=7.8 Hz), 8.62-8.63 (1H, m), 8.97-8.99 (1H, m)

Example 24

2-{4-[(1-cyclobutylpiperidin-4-yl)oxy]phenyl}-8-methoxyquinazolin-4(3H)-one

The entitled compound was obtained according to the method of Example 15 but starting from 2-amino-3-methoxybenzoic acid, ammonia and 4-[(1-cyclobutyl-4-piperidinyl)oxy]benzaldehyde.

$^1$H-NMR (400 MHz, CD$_3$OD) δ: 1.69-1.78 (2H, m), 1.78-1.89 (2H, m), 1.89-1.98 (2H, m), 2.02-2.13 (4H, m), 2.25-2.36 (2H, m), 2.64-2.74 (2H, m), 2.86 (1H, quint., J=8.0 Hz), 4.02 (3H, s), 4.53-4.61 (1H, m), 7.09 (2H, d, J=9.0 Hz), 7.37 (1H, dd, J=8.0, 1.4 Hz), 7.44 (1H, t, J=8.0 Hz), 7.78 (1H, dd, J=8.0, 1.4 Hz), 8.03 (2H, d, J=9.0 Hz)

Example 25

7-Bromo-2-{4-[(1-cyclopentylpiperidin-4-yl)oxy]-2-methoxyphenyl}-3-methylpyrido[3,2-d]pyrimidin-4(3H)-one The entitled compound was obtained according to the method of Example 15 but starting from 3-amino-5-bromopyridine-2-carboxylic acid, methylamine and 4-[(1-cyclopentylpiperidin-4-yl)oxy]-2-methoxybenzaldehyde.

¹H-NMR (400 MHz, CDCl₃) δ: 1.32-1.51 (2H, m), 1.51-1.65 (2H, m), 1.66-1.78 (2H, m), 1.81-1.95 (4H, m), 1.98-2.15 (2H, m), 2.24-2.46 (2H, m), 2.47-2.62 (1H, m), 2.73-2.90 (2H, m), 3.48 (3H, s), 3.81 (3H, s), 4.38-4.46 (1H, m), 6.56 (1H, d, J=2.0 Hz), 6.63 (1H, dd, J=8.3, 2.4 Hz), 7.32 (1H, d, J=8.3 Hz), 8.23 (1H, d, J=2.4 Hz), 8.87 (1H, d, J=2.4 Hz)

Example 26

7-Bromo-2-{4-[(1-cyclobutylpiperidin-4-yl)oxy]-2-methoxyphenyl}-3-methylpyrido[3,2-d]pyrimidin-4(3H)-one The entitled compound was obtained according to the method of Example 15 but starting from 3-amino-5-bromopyridine-2-carboxylic acid, methylamine and 4-[(1-cyclobutylpiperidin-4-yl)oxy]-2-methoxybenzaldehyde.

¹H-NMR (400 MHz, CDCl₃) δ: 1.64-1.78 (2H, m), 1.80-1.98 (4H, m), 1.98-2.13 (4H, m), 2.13-2.29 (2H, m), 2.56-2.70 (2H, m), 2.70-2.83 (1H, m), 3.48 (3H, s), 3.81 (3H, s), 4.35-4.47 (1H, m), 6.55 (1H, d, J=2.0 Hz), 6.62 (1H, dd, J=8.3, 2.0 Hz), 7.32 (1H, d, J=8.3 Hz), 8.23 (1H, d, J=2.0 Hz), 8.87 (1H, d, J=2.0 Hz)

Example 27

2-{6-[(1-cyclobutylpiperidin-4-yl)oxy]pyridin-3-yl}-8-methoxy-3-methylquinazolin-4(3H)-one The entitled compound was obtained according to the method of Example 15 but starting from 2-amino-3-methoxybenzoic acid, methylamine and 6-[(1-cyclobutylpiperidin-4-yl)oxy]nicotinaldehyde.

¹H-NMR (400 MHz, CDCl₃) δ: 1.64-1.77 (2H, m), 1.78-1.98 (4H, m), 1.99-2.13 (4H, m), 2.13-2.29 (2H, m), 2.62-2.80 (3H, m), 3.56 (3H, s), 4.00 (3H, s), 5.12-5.21 (1H, m), 6.83 (1H, d, J=8.8 Hz), 7.21 (1H, dd, J=8.0, 1.2 Hz), 7.45 (1H, t, J=8.0 Hz), 7.79 (1H, dd, J=8.8, 1.7 Hz), 7.90 (1H, dd, J=8.0, 1.2 Hz), 8.42 (1H, d, J=1.7 Hz)

Example 28

6-Chloro-2-{4-[(1-cyclopentylpiperidin-4-yl)oxy]phenyl}-3-methylpyrido[3,4-d]pyrimidin-4(3H)-one The entitled compound was obtained according to the method of Example 15 but starting from 5-amino-2-chloroisonicotinic acid, methylamine and 4-[(1-cyclopentyl-4-piperidinyl)oxy]benzaldehyde.

¹H-NMR (400 MHz, CDCl₃) δ: 1.39-1.48 (2H, m), 1.54-1.59 (2H, m), 1.66-1.76 (2H, m), 1.87-1.92 (4H, m), 2.03-2.06 (2H, br m), 2.37-2.39 (2H, br m), 2.54 (1H, t, J=7.6 Hz), 2.81-2.83 (2H, br m), 3.57 (3H, s), 4.42-4.44 (1H, br m), 7.04 (2H, d, J=9.0 Hz), 7.53 (2H, d, J=9.0 Hz), 8.11 (1H, d, J=0.8 Hz), 8.95 (1H, d, J=0.8 Hz)

Example 29

2-{4-[(1-Cyclobutylpiperidin-4-yl)oxy]phenyl}-8-methoxy-3-methylpyrido[3,4-d]pyrimidin-4(3H)-one The entitled compound was obtained according to the method of Example 15 but starting from 3-amino-2-methoxyisonicotinic acid, methylamine and 4-[(1-cyclobutyl-4-piperidinyl)oxy]benzaldehyde. The obtained compound was recrystallized from ethyl acetate-heptane to give a colorless tabular crystal (m.p. 178.0-180.2° C.).

¹H-NMR (400 MHz, CDCl₃) δ: 1.63-1.77 (2H, m), 1.80-1.96 (4H, m), 1.98-2.10 (4H, m), 2.14-2.24 (2H, m), 2.61-2.63 (2H, br m), 2.75 (1H, t, J=7.4 Hz), 3.55 (3H, s), 4.12 (3H, s), 4.41-4.42 (1H, m), 7.00 (2H, dt, J=9.4, 2.5 Hz), 7.51 (2H, dt, J=9.2, 2.4 Hz), 7.65 (1H, d, J=5.5 Hz), 8.16 (1H, d, J=5.5 Hz)

Example 30

6-Chloro-2-{4-[(1-cyclobutylpiperidin-4-yl)oxy]phenyl}-3-methylpyrido[3,4-d]pyrimidin-4(3H)-one The entitled compound was obtained according to the method of Example 15 but starting from 5-amino-2-chloroisonicotinic acid, methylamine and 4-[(1-cyclobutyl-4-piperidinyl)oxy]benzaldehyde.

¹H-NMR (400 MHz, CDCl₃) δ: 1.64-1.77 (2H, m), 1.81-1.96 (4H, m), 1.98-2.10 (4H, m), 2.14-2.24 (2H, m), 2.58-2.67 (2H, m), 2.75 (1H, quint., J=8.2 Hz), 3.57 (3H, s), 4.42-4.45 (1H, br m), 7.04 (2H, d, J=8.6 Hz), 7.53 (2H, d, J=8.6 Hz), 8.11 (1H, s), 8.95 (1H, s)

Example 31

6-Chloro-2-[2-methoxy-4-(3-pyrrolidin-1-ylpropoxy)phenyl]-3-methylpyrido[3,4-d]pyrimidin-4(3H)-one The entitled compound was obtained according to the method of Example 15 but starting from 5-amino-2-chloroisonicotinic acid, methylamine and 2-methoxy-4-(3-pyrrolidin-1-ylpropoxy)benzaldehyde.

¹H-NMR (400 MHz, CDCl₃) δ: 1.79-1.84 (4H, m), 2.05 (2H, quint., J=7.2 Hz), 2.54-2.57 (4H, br m), 2.66 (2H, t, J=7.2 Hz), 3.43 (3H, s), 3.81 (3H, s), 4.11 (2H, t, J=6.5 Hz), 6.56 (1H, d, J=2.0 Hz), 6.64 (1H, dd, J=8.2, 2.0 Hz), 7.35 (1H, d, J=8.2 Hz), 8.12 (1H, d, J=0.8 Hz), 8.95 (1H, d, J=0.8 Hz)

Example 32

2-{4-[(1-Cyclobutylpiperidin-4-yl)oxy]phenyl}-8-methylquinazolin-4(3H)-one

The entitled compound was obtained according to the method of Example 15 but starting from 2-amino-3-methylbenzoic acid, ammonia and 4-[(1-cyclobutyl-4-piperidinyl)oxy]benzaldehyde.

¹H-NMR (400 MHz, CDCl₃) δ: 1.65-1.76 (2H, m), 1.83-1.95 (4H, m), 2.01-2.10 (4H, m), 2.16-2.25 (2H, m), 2.60-2.68 (2H, m), 2.71 (3H, s), 2.76 (1H, t, J=7.6 Hz), 4.43-4.50 (1H, m), 7.06 (2H, d, J=9.0 Hz), 7.35 (1H, t, J=7.6 Hz), 7.63 (1H, d, J=7.6 Hz), 8.11 (2H, d, J=9.0 Hz), 8.15 (1H, d, J=7.6 Hz)

Example 33

8-Methoxy-3-methyl-2-[4-(3-pyrrolidin-1-ylpropoxy)phenyl]pyrido[3,4-d]pyrimidin-4(3H)-one The entitled compound was obtained according to the method of Example 15 but starting from 3-amino-2-methoxyisonicotinic acid, methylamine and 4-(3-pyrrolidin-1-ylpropoxy)benzaldehyde.

¹H-NMR (400 MHz, CDCl₃) δ: 1.80-1.83 (4H, m), 2.05 (2H, quint., J=7.4 Hz), 2.53-2.58 (4H, m), 2.65 (2H, t, J=7.4

Hz), 3.54 (3H, s), 4.10 (2H, t, J=6.3 Hz), 4.13 (3H, s), 7.01 (2H, d, J=9.0 Hz), 7.52 (2H, d, J=9.0 Hz), 7.65 (1H, d, J=5.5 Hz), 8.16 (1H, d, J=5.5 Hz)

Example 34

2-{4-[(1-Cyclopentylpiperidin-4-yl)oxy]phenyl}-8-methoxy-3-methylpyrido[3,4-d]pyrimidin-4(3H)-one The entitled compound was obtained according to the method of Example 15 but starting from 3-amino-2-methoxyisonicotinic acid, methylamine and 4-[(1-cyclopentyl-4-piperidinyl)oxy]benzaldehyde.

$^1$H-NMR (400 MHz, CDCl$_3$) δ: 1.37-1.48 (2H, m), 1.52-1.60 (2H, m), 1.66-1.76 (2H, m), 1.82-1.93 (4H, m), 2.00-2.08 (2H, m), 2.33-2.42 (2H, m), 2.54 (1H, quint., J=8.2 Hz), 2.76-2.86 (2H, m), 3.55 (3H, s), 4.13 (3H, s), 4.38-4.44 (1H, m), 7.01 (2H, d, J=8.6 Hz), 7.51 (2H, d, J=8.6 Hz), 7.65 (1H, d, J=5.5 Hz), 8.16 (1H, d, J=5.5 Hz)

Example 35

8-Chloro-2-{4-[(1-cyclobutylpiperidin-4-yl)oxy]phenyl}-3-methylquinazolin-4(3H)-one The entitled compound was obtained according to the method of Example 15 but starting from 2-amino-3-chlorobenzoic acid, methylamine and 4-[(1-cyclobutyl-4-piperidinyl)oxy]benzaldehyde.

$^1$H-NMR (400 MHz, CDCl$_3$) δ: 1.65-1.78 (2H, m), 1.79-1.97 (4H, m), 1.98-2.11 (4H, m), 2.12-2.29 (2H, m), 2.54-2.70 (2H, m), 2.76 (1H, quint., J=7.8 Hz), 3.57 (3H, s), 4.39-4.47 (1H, m), 7.02 (2H, d, J=8.8 Hz), 7.39 (1H, t, J=7.8 Hz), 7.59 (2H, d, J=8.8 Hz), 7.82 (1H, dd, J=7.8, 1.5 Hz), 8.23 (1H, dd, J=7.8, 1.5 Hz)

Example 36

2-{4-[(1-Cyclobutylpiperidin-4-yl)oxy]phenyl}-3-methyl-8-(trifluoromethyl)quinazolin-4(3H)-one The entitled compound was obtained according to the method of Example 15 but starting from 2-amino-3-trifluoromethylbenzoic acid, methylamine and 4-[(1-cyclobutyl-4-piperidinyl)oxy]benzaldehyde.

$^1$H-NMR (400 MHz, CDCl$_3$) δ: 1.47-1.81 (2H, m), 1.81-1.99 (4H, m), 1.99-2.14 (4H, m), 2.14-2.37 (2H, m), 2.55-2.73 (2H, m), 2.73-2.89 (1H, m), 3.61 (3H, s), 4.35-4.52 (1H, m), 7.01 (2H, d, J=8.8 Hz), 7.51 (1H, t, J=7.8 Hz), 7.62 (2H, d, J=8.8 Hz), 8.05 (1H, d, J=7.8 Hz), 8.50 (1H, d, J=7.8 Hz)

Example 37

2-{6-[(1-Cyclobutylpiperidin-4-yl)oxy]pyridin-3-yl}-3,8-dimethylquinazolin-4(3H)-one The entitled compound was obtained according to the method of Example 15 but starting from 2-amino-3-methylbenzoic acid, methylamine and 6-[(1-cyclobutylpiperidin-4-yl)oxy]nicotinaldehyde.

$^1$H-NMR (400 MHz, CDCl$_3$) δ: 1.63-1.79 (2H, m), 1.79-2.01 (4H, m), 2.01-2.28 (6H, m), 2.60 (3H, s), 2.62-2.87 (3H, m), 3.59 (3H, s), 5.10-5.23 (1H, m), 6.85 (1H, d, J=8.8 Hz), 7.38 (1H, t, J=7.8 Hz), 7.61 (1H, d, J=7.8 Hz), 7.84 (1H, dd, J=8.8, 2.4 Hz), 8.17 (1H, d, J=7.8 Hz), 8.47 (1H, d, J=2.4 Hz)

Example 38

6-Chloro-2-{4-[(1-cyclobutylpiperidin-4-yl)oxy]-2-methoxyphenyl}-3-methylpyrido[3,4-d]pyrimidin-4(3H)-one The entitled compound was obtained according to the method of Example 15 but starting from 5-amino-2-chloroisonicotinic acid, methylamine and 4-[(1-cyclobutylpiperidin-4-yl)oxy]-2-methoxybenzaldehyde.

$^1$H-NMR (400 MHz, CDCl$_3$) δ: 1.77-1.65 (2H, m), 1.95-1.82 (4H, m), 2.10-1.99 (4H, m), 2.14-2.25 (2H, m), 2.58-2.70 (2H, m), 2.72-2.80 (1H, m), 3.44 (3H, s), 3.81 (3H, s), 4.38-4.45 (1H, m), 6.55 (1H, d, J=2.4 Hz), 6.63 (1H, dd, J=8.8, 2.4 Hz), 7.34 (1H, d, J=8.8 Hz), 8.12 (1H, d, J=1.0 Hz), 8.95 (1H, d, J=1.0 Hz)

Example 39

6-Chloro-2-{4-[(1-cyclopentylpiperidin-4-yl)oxy]-2-methoxyphenyl}-3-methylpyrido[3,4-d]pyrimidin-4(3H)-one The entitled compound was obtained according to the method of Example 15 but starting from 5-amino-2-chloroisonicotinic acid, methylamine and 4-[(1-cyclopentylpiperidin-4-yl)oxy]-2-methoxybenzaldehyde.

$^1$H-NMR (400 MHz, CDCl$_3$) δ: 1.36-1.50 (2H, m), 1.50-1.64 (2H, m), 1.66-1.78 (2H, m), 1.82-1.96 (4H, m), 2.01-2.13 (2H, m), 2.32-2.44 (2H, m), 2.49-2.61 (1H, m), 2.76-2.90 (2H, m), 3.44 (3H, s), 3.81 (3H, s), 4.37-4.45 (1H, m), 6.56 (1H, d, J=2.0 Hz), 6.63 (1H, dd, J=8.8, 2.0 Hz), 7.34 (1H, d, J=8.8 Hz), 8.12 (1H, d, J=1.0 Hz), 8.95 (1H, d, J=1.0 Hz)

Example 40

2-{4-[(1-Cyclobutylpiperidin-4-yl)oxy]phenyl}-8-fluoro-3-methylquinazolin-4(3H)-one The entitled compound was obtained according to the method of Example 15 but starting from 2-amino-3-fluorobenzoic acid, methylamine and 4-[(1-cyclobutylpiperidin-4-yl)oxy]-2-methoxybenzaldehyde.

$^1$H-NMR (400 MHz, CDCl$_3$) δ: 1.64-1.77 (2H, m), 1.81-1.95 (4H, m), 1.98-2.10 (4H, m), 2.14-2.26 (2H, m), 2.57-2.67 (2H, m), 2.76 (1H, quint., J=8.0 Hz), 3.55 (3H, s), 4.39-4.46 (1H, m), 7.01 (2H, d, J=8.8 Hz), 7.39-7.50 (2H, m), 7.54 (2H, d, J=8.8 Hz), 8.10 (1H, d, J=7.6 Hz)

Example 41

2-{4-[(1-Cyclopentylpiperidin-4-yl)oxy]phenyl}-8-fluoro-3-methylquinazolin-4(3H)-one The entitled compound was obtained according to the method of Example 15 but starting from 2-amino-3-fluorobenzoic acid, methylamine and 4-[(1-cyclopentylpiperidin-4-yl)oxy]-2-methoxybenzaldehyde.

$^1$H-NMR (400 MHz, CDCl$_3$) δ: 1.36-1.50 (2H, m), 1.52-1.63 (2H, m), 1.65-1.76 (2H, m), 1.82-1.95 (4H, m), 2.00-2.10 (2H, m), 2.32-2.44 (2H, m), 2.54 (1H, quint., J=7.6 Hz), 2.77-2.86 (2H, m), 3.56 (3H, s), 4.38-4.46 (1H, m), 7.02 (2H, d, J=8.8 Hz), 7.39-7.50 (2H, m), 7.54 (2H, d, J=8.8 Hz), 8.10 (1H, d, J=7.8 Hz)

Example 42

8-Fluoro-2-(2-methoxy-4-{3[(3S)-3-methylpiperidin-1-yl]propoxy}phenyl)-3-methylquinazolin-4(3H)-one The entitled compound was obtained according to the method of Example 15 but starting from 2-amino-3-fluorobenzoic acid, methylamine and 2-methoxy-4-{3-[(3S)-3-methylpiperidin-1-yl]propoxy}benzaldehyde.

$^1$H-NMR (400 MHz, CDCl$_3$) δ: 0.86-0.91 (1H, m), 0.88 (3H, d, J=6.3 Hz), 1.52-1.62 (3H, m), 1.63-1.76 (2H, m), 1.83-1.91 (1H, m), 2.02 (2H, quint., J=7.1 Hz), 2.51 (2H, t, J=7.6 Hz), 2.82-2.93 (2H, m), 3.42 (3H, s), 3.80 (3H, s), 4.07 (2H, t, J=6.6 Hz), 6.52 (1H, d, J=2.0 Hz), 6.61 (1H, dd, J=8.3, 2.0 Hz), 7.37 (1H, d, J=8.3 Hz), 7.38-7.48 (2H, m), 8.11 (1H, d, J=7.8 Hz)

Example 43

5-Fluoro-3-methyl-2-[4-(3-pyrrolidin-1-ylpropoxy)phenyl]quinazolin-4(3H)-one

The entitled compound was obtained according to the method of Example 15 but starting from 2-amino-6-fluorobenzoic acid, methylamine and 4-(3-pyrrolidin-1-ylpropoxy)benzaldehyde.

$^1$H-NMR (400 MHz, CDCl$_3$) δ: 1.78-1.86 (4H, m), 2.07 (2H, quint., J=7.0 Hz), 2.57-2.64 (4H, m), 2.70 (2H, t, J=7.4 Hz), 3.50 (3H, s), 4.11 (2H, t, J=6.3 Hz), 7.03 (2H, d, J=8.6 Hz), 7.11 (1H, dd, J=10.2, 8.6 Hz), 7.49-7.54 (1H, m), 7.52 (2H, d, J=8.6 Hz), 7.66 (1H, td, J=8.2, 5.5 Hz)

Example 44

2-{4-[(1-Cyclobutylpiperidin-4-yl)oxy]phenyl}-5-fluoro-3-methylquinazolin-4(3H)-one The entitled compound was obtained according to the method of Example 15 but starting from 2-amino-6-fluorobenzoic acid, methylamine and 4-[(1-cyclobutylpiperidin-4-yl)oxy]-2-methoxybenzaldehyde.

$^1$H-NMR (400 MHz, CDCl$_3$) δ: 1.62-1.83 (2H, m), 1.86-1.99 (2H, m), 2.00-2.24 (6H, m), 2.28-2.55 (2H, m), 2.60-2.75 (2H, m), 2.80-2.95 (1H, m), 3.51 (3H, s), 4.45-4.54 (1H, m), 7.02 (2H, d, J=8.8 Hz), 7.13 (1H, ddd, J=10.6, 8.2, 1.1 Hz), 7.50-7.54 (1H, m), 7.52 (2H, d, J=8.8 Hz), 7.67 (1H, td, J=8.3, 5.4 Hz)

Example 45

2-{4-[(1-Cyclobutylpiperidin-4-yl)oxy]phenyl}-3,8-dimethylpyrido[4,3-d]pyrimidin-4(3H)-one The entitled compound was obtained according to the method of Example 15 but starting from 4-amino-5-methylnicotinic acid, methylamine and 4-[(1-cyclobutylpiperidin-4-yl)oxy]-2-methoxybenzaldehyde.

$^1$H-NMR (400 MHz, CDCl$_3$) δ: 1.63-1.76 (2H, m), 1.82-1.96 (4H, m), 1.99-2.10 (4H, m), 2.14-2.25 (2H, m), 2.53 (3H, s), 2.58-2.69 (2H, m), 2.76 (1H, quint., J=7.8 Hz), 3.57 (3H, s), 4.39-4.48 (1H, m), 7.03 (2H, d, J=8.8 Hz), 7.57 (2H, d, J=8.8 Hz), 8.68 (1H, s), 9.39 (1H, s)

Example 46

2-{2-[(1-Cyclobutylpiperidin-4-yl)oxy]pyrimidin-5-yl}-8-methoxy-3-methylquinazolin-4(3H)-one The entitled compound was obtained according to the method of Example 15 but starting from 2-amino-3-methoxybenzoic acid, methylamine and 2-[(1-cyclobutylpiperidin-4-yl)oxy]pyrimidine-5-carbaldehyde.

$^1$H-NMR (400 MHz, CDCl$_3$) δ: 1.64-1.77 (2H, m), 1.84-2.00 (4H, m), 2.01-2.13 (4H, m), 2.16-2.29 (2H, m), 2.63-2.73 (2H, m), 2.77 (1H, quint., J=7.8 Hz), 3.59 (3H, s), 4.01 (3H, s), 5.11-5.21 (1H, m), 7.23 (1H, dd, J=7.8, 1.0 Hz), 7.48 (1H, t, J=8.0 Hz), 7.91 (1H, dd, J=8.0, 1.0 Hz), 8.79 (2H, s)

Example 47

2-{2-[(1-Cyclobutylpiperidin-4-yl)oxy]pyrimidin-5-yl}-8-methoxy-3-methylpyrido[3,4-d]pyrimidin-4(3H)-one The entitled compound was obtained according to the method of Example 15 but starting from 3-amino-2-methoxyisonicotinic acid, methylamine and 2-[(1-cyclobutylpiperidin-4-yl)oxy]pyrimidine-5-carbaldehyde.

$^1$H-NMR (400 MHz, CDCl$_3$) δ: 1.63-1.77 (2H, m), 1.85-2.00 (4H, m), 2.01-2.15 (4H, m), 2.16-2.29 (2H, m), 2.64-2.74 (2H, m), 2.74-2.81 (1H, m), 3.61 (3H, s), 4.15 (3H, s), 5.13-5.20 (1H, m), 7.66 (1H, d, J=5.4 Hz), 8.22 (1H, d, J=5.4 Hz), 8.78 (2H, s)

Example 48

2-{6-[(1-Cyclobutylpiperidin-4-yl)oxy]pyrimidin-3-yl}-8-methoxy-3-methylpyrido[3,4-d]pyrimidin-4(3H)-one The entitled compound was obtained according to the method of Example 15 but starting from 3-amino-2-methoxyisonicotinic acid, methylamine and 6-[(1-cyclobutylpiperidin-4-yl)oxy]nicotinaldehyde. The resulting compound was recrystallized from ethyl acetate-heptane to give a colorless solid (m.p. 199.0-200.2° C.).

$^1$H-NMR (400 MHz, CDCl$_3$) δ: 1.63-1.77 (2H, m), 1.79-1.97 (4H, m), 2.00-2.11 (4H, m), 2.12-2.25 (2H, m), 2.61-2.72 (2H, m), 2.75 (1H, quint., J=7.3 Hz), 3.58 (3H, s), 4.13 (3H, s), 5.11-5.20 (1H, m), 6.84 (1H, d, J=8.8 Hz), 7.65 (1H, d, J=5.4 Hz), 7.78 (1H, dd, J=8.8, 2.4 Hz), 8.19 (1H, d, J=5.4 Hz), 8.41 (1H, d, J=2.4 Hz)

Example 49

2-{4-[(1-Cyclobutylpiperidin-4-yl)oxy]phenyl}-6-methoxy-3-methylpyrido[3,4-d]pyrimidin-4(3H)-one The entitled compound was obtained according to the method of Example 15 but starting from 5-amino-2-methoxyisonicotinic acid, methylamine and 4-[(1-cyclobutyl-4-piperidinyl)oxy]benzaldehyde. The resulting compound was recrystallized from ethyl acetate-heptane to give a colorless tabular crystal (m.p. 146.5-148.0° C.).

$^1$H-NMR (400 MHz, CDCl$_3$) δ: 1.63-1.77 (2H, m), 1.80-1.95 (4H, m), 1.97-2.10 (4H, m), 2.12-2.25 (2H, m), 2.56-2.68 (2H, m), 2.75 (1H, quint., J=7.8 Hz), 3.52 (3H, s), 4.04

(3H, s), 4.38-4.46 (1H, m), 7.02 (2H, d, J=8.8 Hz), 7.49 (1H, d, J=1.0 Hz), 7.50 (2H, d, J=8.8 Hz), 8.81 (1H, d, J=1.0 Hz)

Example 50

2-{4-[(1-Cyclopentylpiperidin-4-yl)oxy]phenyl}-6-methoxy-3-methylpyrido[3,4-d]pyrimidin-4(3H)-one The entitled compound was obtained according to the method of Example 15 but starting from 5-amino-2-methoxy-isonicotinic acid, methylamine and 4-[(1-cyclopentyl-4-piperidinyl)oxy]benzaldehyde.

$^1$H-NMR (400 MHz, DMSO-d$_6$) δ: 1.27-1.40 (2H, m), 1.43-1.55 (2H, m), 1.57-1.69 (4H, m), 1.75-1.84 (2H, m), 1.93-2.02 (2H, m), 2.20-2.28 (2H, m), 2.45-2.55 (1H, m), 2.73-2.81 (2H, m), 3.39 (3H, s), 3.97 (3H, s), 4.43-4.51 (1H, m), 7.09 (2H, d, J=8.8 Hz), 7.33 (1H, s), 7.60 (2H, d, J=8.8 Hz), 8.77 (1H, d, J=1.0 Hz)

Example 51

3-Methyl-2-(4-{3-[(3S)-3-methylpiperidin-1-yl]propoxy}phenyl)pyrido[3,2-d]pyrimidin-4(3H)-one The entitled compound was obtained according to the method of Example 15 but starting from 3-aminopyridin-2-carboxylic acid, methylamine and 4-{3-[(3S)-3-methylpiperidin-1-yl]propoxy}benzaldehyde. The resulting compound was recrystallized from diethyl ether-heptane to give a colorless acicular crystal (m.p. 83.5-88.5° C.).

$^1$H-NMR (400 MHz, CDCl$_3$) δ: 0.82-0.93 (1H, m), 0.88 (3H, d, J=6.3 Hz), 1.52-1.73 (5H, m), 1.86 (1H, td, J=11.2, 2.9 Hz), 2.02 (2H, quint., J=7.3 Hz), 2.49 (2H, t, J=7.3 Hz), 2.86 (2H, t, J=13.7 Hz), 3.61 (3H, s), 4.09 (2H, t, J=6.3 Hz), 7.04 (2H, dt, J=9.4, 2.4 Hz), 7.53 (2H, dt, J=9.4, 2.4 Hz), 7.67 (1H, dd, J=8.3, 4.4 Hz), 8.07 (1H, dd, J=8.3, 1.5 Hz), 8.88 (1H, dd, J=4.4, 1.5 Hz)

Example 52

2-{4-[(1-Cyclobutylpiperidin-4-yl)oxy]phenyl}-3-methylpyrido[3,2-d]pyrimidin-4(3H)-one The entitled compound was obtained according to the method of Example 15 but starting from 3-amino-2-carboxylic acid, methylamine and 4-[(1-cyclobutyl-4-piperidinyl)oxy]benzaldehyde. The resulting compound was recrystallized from ethyl acetate-heptane to give a colorless acicular crystal (m.p. 181.5-183.0° C.).

$^1$H-NMR (400 MHz, CDCl$_3$) δ: 1.64-1.77 (2H, m), 1.82-1.96 (4H, m), 1.98-2.10 (4H, m), 2.13-2.26 (2H, m), 2.55-2.69 (2H, m), 2.75 (1H, quint., J=7.6 Hz), 3.62 (3H, s), 4.39-4.48 (1H, m), 7.04 (2H, dt, J=9.4, 2.4 Hz), 7.53 (2H, dt, J=9.4, 2.4 Hz), 7.67 (1H, dd, J=8.3, 4.4 Hz), 8.07 (1H, dd, J=8.3, 1.5 Hz), 8.88 (1H, dd, J=4.4, 1.5 Hz)

Example 53

2-{4-[(1-Cyclopentylpiperidin-4-yl)oxy]phenyl}1-3-methylpyrido[3,2-d]pyrimidin-4(3H)-one The entitled compound was obtained according to the method of Example 15 but starting from 3-aminopyridine-2-carboxylic acid, methylamine and 4-[(1-cyclopentyl-4-piperidinyl)oxy]benzaldehyde.

$^1$H-NMR (400 MHz, CDCl$_3$) δ: 1.36-1.48 (2H, m), 1.50-1.60 (2H, m), 1.65-1.75 (2H, m), 1.83-1.94 (4H, m), 2.01-2.10 (2H, m), 2.31-2.42 (2H, m), 2.53 (1H, quint., J=7.3 Hz), 2.77-2.86 (2H, m), 3.62 (3H, s), 4.39-4.46 (1H, m), 7.04 (2H, dt, J=9.4, 2.4 Hz), 7.53 (2H, dt, J=9.4, 2.4 Hz), 7.67 (1H, dd, J=8.3, 4.4 Hz), 8.07 (1H, dd, J=8.3, 1.7 Hz), 8.88 (1H, dd, J=4.4, 1.7 Hz)

Example 54

3,8-Dimethyl-2-(4-{3-[(3S)-3-methylpiperidin-1-yl]propoxy}phenyl)pyrido[4,3-d]pyrimidin-4(3H)-one The entitled compound was obtained according to the method of Example 15 but starting from 4-amino-5-methylnicotinic acid, methylamine and 4-{3-[(3S)-3-methylpiperidin-1-yl]propoxy}benzaldehyde.

$^1$H-NMR (400 MHz, CDCl$_3$) δ: 0.82-0.94 (1H, m), 0.88 (3H, d, J=6.3 Hz), 1.57-1.74 (5H, m), 1.88 (1H, td, J=11.7, 3.4 Hz), 2.04 (2H, quint., J=6.8 Hz), 2.49-2.55 (2H, m), 2.53 (3H, s), 2.82-2.94 (2H, m), 3.57 (3H, s), 4.10 (2H, t, J=6.3 Hz), 7.04 (2H, dt, J=9.4, 2.4 Hz), 7.58 (2H, dt, J=9.4, 2.4 Hz), 8.68 (1H, d, J=1.0 Hz), 9.39 (1H, d, J=1.0 Hz)

Example 55

7-Bromo-3-methyl-2-(4-{3-[(3S)-3-methylpiperidin-1-yl]propoxy}phenyl)pyrido[3,2-d]pyrimidin-4(3H)-one The entitled compound was obtained according to the method of Example 15 but starting from 3-amino-5-bromopyridine-2-carboxylic acid, methylamine and 4-{3-[(3S)-3-methylpiperidin-1-yl]propoxy}benzaldehyde.

$^1$H-NMR (400 MHz, CDCl$_3$) δ: 0.83-0.94 (1H, m), 0.88 (3H, d, J=6.3 Hz), 1.61-1.78 (5H, m), 1.84-1.94 (1H, m), 2.04 (2H, quint., J=7.3 Hz), 2.52 (2H, t, J=7.3 Hz), 2.85-2.93 (2H, m), 3.61 (3H, s), 4.10 (2H, t, J=6.3 Hz), 7.04 (2H, dt, J=9.4, 2.4 Hz), 7.53 (2H, dt, J=9.4, 2.4 Hz), 8.24 (1H, d, J=2.4 Hz), 8.87 (1H, d, J=2.4 Hz)

Example 56

7-Methoxy-3-methyl-2-[4-(3-pyrrolidin-1-ylpropoxy)phenyl]quinazolin-4(3H)-one

The entitled compound was obtained according to the method of Example 15 but starting from 2-amino-4-methoxybenzoic acid, methylamine and 4-(3-pyrrolidin-1-ylpropoxy)benzaldehyde.

$^1$H-NMR (400 MHz, CDCl$_3$) δ: 1.81-1.86 (4H, m), 2.08 (2H, quint., J=7.3 Hz), 2.56-2.63 (4H, m), 2.69 (2H, t, J=7.3 Hz), 3.51 (3H, s), 3.90 (3H, s), 4.11 (2H, t, J=6.3 Hz), 7.03 (2H, d, J=8.8 Hz), 7.06 (1H, dd, J=8.8, 2.4 Hz), 7.11 (1H, d, J=2.4 Hz), 7.51 (2H, d, J=8.8 Hz), 8.21 (1H, d, J=8.8 Hz)

Example 57

7-Methoxy-3-methyl-2-[4-(3-[(3S)-3-methylpiperidin-1-yl]propoxy)phenyl]quinazolin-4(3H)-one The entitled compound was obtained according to the method of Example 15 but starting from 2-amino-4-methoxybenzoic acid, methylamine and 4-{3-[(3S)-3-methylpiperidin-1-yl]propoxy} benzaldehyde.

$^1$H-NMR (400 MHz, CDCl$_3$) δ: 0.83-0.93 (1H, m), 0.88 (3H, d, J=6.3 Hz), 1.59-1.74 (5H, m), 1.85-1.94 (1H, m), 2.05 (2H, quint., J=7.8 Hz), 2.54 (2H, t, J=7.3 Hz), 2.86-2.95 (2H, m), 3.51 (3H, s), 3.90 (3H, s), 4.09 (2H, t, J=6.3 Hz), 7.02 (2H, d, J=8.8 Hz), 7.05 (1H, dd, J=8.8, 2.4 Hz), 7.11 (1H, d, J=2.4 Hz), 7.51 (2H, d, J=8.8 Hz), 8.20 (1H, d, J=8.8 Hz)

Example 58

2-{4-[(1-cyclobutylpiperidin-4-yl)oxy]phenyl}-7-methoxy-3-methyl quinazolin-4(3H)-one The entitled compound was obtained according to the method of Example 15 but starting from 2-amino-4-methoxybenzoic acid, methylamine and 4-[(1-cyclobutyl-4-piperidinyl)oxy]benzaldehyde.
$^1$H-NMR (400 MHz, CDCl$_3$) δ: 1.64-1.77 (2H, m), 1.81-1.95 (4H, m), 1.98-2.10 (4H, m), 2.12-2.26 (2H, m), 2.55-2.69 (2H, m), 2.75 (1H, quint., J=7.8 Hz), 3.52 (3H, s), 3.90 (3H, s), 4.38-4.45 (1H, m), 7.02 (2H, d, J=8.8 Hz), 7.06 (1H, dd, J=8.8, 2.4 Hz), 7.11 (1H, d, J=2.4 Hz), 7.50 (2H, d, J=8.8 Hz), 8.21 (1H, d, J=8.8 Hz)

Example 59

2-{4-[(1-cyclobutylpiperidin-4-yl)oxy]phenyl}-8-methoxy-3-methylpyrido[3,2-d]pyrimidin-4(3H)-one The entitled compound was obtained as a pale yellow solid (m.p. 182.2-205.2° C.), according to the method of Example 15 but starting from 3-amino-4-methoxypyridin-2-carboxylic acid, methylamine and 4-[(1-cyclobutyl-4-piperidinyl)oxy]benzaldehyde.
$^1$H-NMR (400 MHz, CDCl$_3$) δ: 1.65-1.78 (2H, m), 1.79-1.96 (4H, m), 1.98-2.10 (4H, m), 2.14-2.26 (2H, m), 2.54-2.68 (2H, m), 2.76 (1H, quint., J=7.8 Hz), 3.59 (3H, s), 4.04 (3H, s), 4.38-4.46 (1H, m), 7.00 (2H, d, J=8.8 Hz), 7.07 (1H, d, J=5.4 Hz), 7.52 (2H, d, J=8.8 Hz), 8.72 (1H, d, J=5.4 Hz)

Example 60

7-Bromo-[2-(2-fluoroethoxy)-4-(3-piperidin-1-ylpropoxy)phenyl]-3-methylquinazolin-4(3H)-one (1) Production of 7-bromo-2-[2-methoxy-4-(3-piperidin-1-ylpropoxy)phenyl]-3-methylquinazolin-4(3H)-one:
The intended compound was obtained according to the method of Example 15 but starting from 4-bromo-2-aminobenzoic acid, methylamine and 2-methoxy-4-(3-pyrrolidin-1-ylpropoxy)benzamide.
(2) Production of 7-bromo-2-[2-hydroxy-4-(3-piperidin-1-ylpropoxy)phenyl]-3-methylquinazolin-4(3H)-one:
7-Bromo-2-[2-methoxy-4-(3-piperidin-1-ylpropoxy)phenyl]-3-methylquinazolin-4(3H)-one (38.5 mg, 0.0792 mmol) was dissolved in CH$_2$Cl$_2$ (0.5 mL), stirred with cooling with ice, and boron trifluoride (1.0 M in CH$_2$Cl$_2$, 160 μL) was added thereto. After stirred for 20 hours at room temperature, the reaction solution was diluted with ethyl acetate, and with cooling with ice, it was poured into aqueous 1 N sodium hydroxide solution, and extracted with ethyl acetate. This was washed with saturated saline water and dried with magnesium sulfate. The organic layer was concentrated under reduced pressure, and purified through silica gel thin-layer chromatography (chloroform/methanol=9/1) to obtain the intended compound (9.5 mg, 25%) as a pale yellow solid.
(3) Production of 7-bromo-2-[2-(2-fluoroethoxy)-4-(3-piperidin-1-ylpropoxy)phenyl]-3-methylquinazolin-4(3H)-one:
7-Bromo-2-[2-hydroxy-4-(3-piperidin-1-ylpropoxy)phenyl]-3-methylquinazolin-4(3H)-one (9.5 mg, 0.020 mmol) and potassium carbonate (8.3 mg, 0.06 mmol) were stirred in DMF (0.5 mL) at room temperature, and 2-fluoroethyl tosylate (6.6 mg, 0.03 mmol) was dropwise added thereto and stirred at room temperature for 3 hours. The reaction solution was diluted with ethyl acetate, washed with water and saturated saline water, and the organic layer was dried with magnesium sulfate. The solvent was evaporated off, and the residue was purified through silica gel thin-layer chromatography (chloroform/methanol=9/1) to obtain the intended compound (4.5 mg, 47%) as a milky white solid.
$^1$H-NMR (400 MHz, CDCl$_3$) δ: 1.51-1.43 (2H, m), 1.60-1.68 (4H, m), 2.04 (2H, t, J=7.4 Hz), 2.43-2.50 (4H, br m), 2.54 (2H, t, J=7.4 Hz), 3.44 (3H, s), 4.08 (2H, t, J=6.3 Hz), 4.10-4.22 (1H, m), 4.25-4.36 (1H, m), 4.55-4.57 (1H, m), 4.66-4.69 (1H, m), 6.53 (1H, d, J=2.3 Hz), 6.66 (1H, dd, J=8.6, 2.3 Hz), 7.37 (1H, d, J=8.6 Hz), 7.59 (1H, d, J=9.0 Hz), 7.81 (1H, dd, J=9.0, 2.3 Hz), 8.46 (1H, d, J=2.3 Hz)

Example 61

6-Chloro-2-[2-(2-fluoroethoxy)-4-(3-pyrrolidin-1-ylpropoxy)phenyl]-3-methylpyrido[3,4-d]pyrimidin-4(3H)-one The intended compound was produced according to the method of Example 60 but starting from 6-chloro-2-[2-methoxy-4-(3-pyrrolidin-1-ylpropoxy)phenyl]-3-methylpyrido[3,4-d]pyrimidin-4(3H)-one and 2-fluoroethyl tosylate.
$^1$H-NMR (400 MHz, CDCl$_3$) δ: 1.48-1.81 (4H, m), 1.81-1.97 (2H, m), 2.02-2.21 (2H, m), 2.51-2.90 (4H, m), 3.47 (3H, s), 4.09-4.16 (2H, m), 4.18-4.42 (2H, m), 4.63 (2H, dt, J=47.3, 4.1 Hz), 6.56 (1H, d, J=2.0 Hz), 6.68 (1H, dd, J=8.3, 2.0 Hz), 7.39 (1H, d, J=8.3 Hz), 8.13 (1H, s), 8.95 (1H, s)

Example 62

2-{4-[(1-Cyclobutylpiperidin-4-yl)oxy]phenyl}-4-(2-fluoroethoxy)-8-methoxyquinazoline 2-{4-[(1-cyclobutylpiperidin-4-yl)oxy]phenyl}-8-methoxyquinazolin-4(3H)-one (30 mg, 0.074 mmol) and potassium carbonate (30.7 mg, 0.222 mmol) were stirred in DMF (0.5 mL) at room temperature, and 2-fluoroethyl tosylate (24 mg, 0.11 mmol) was dropwise added thereto and stirred at room temperature for 16 hours. The reaction solution was diluted with ethyl acetate, washed with water and saturated saline water in that order, and the organic layer was dried with magnesium sulfate. The solvent was evaporated off, and the residue was purified through thin-layer chromatography (chloroform/methanol=9/1) to obtain the intended compound (15 mg, 45%) as a pale yellow solid.
$^1$H-NMR (400 MHz, CDCl$_3$) δ: 1.64-1.77 (2H, m), 1.82-1.96 (4H, m), 2.01-2.10 (4H, m), 2.15-2.25 (2H, m), 2.61-2.70 (2H, m), 2.73-2.82 (1H, m), 4.08 (3H, s), 4.42-4.48 (1H, m), 4.86-4.87 (1H, m), 4.91-4.92 (1H, m), 4.98 (2H, br s), 6.99 (2H, d, J=9.0 Hz), 7.19 (1H, d, J=7.0 Hz), 7.42 (1H, t, J=8.2 Hz), 7.77 (1H, dd, J=8.2, 1.2 Hz), 8.51 (2H, d, J=9.0 Hz)

Example 63

2-{4-[(1-Cyclobutylpiperidin-4-yl)oxy]phenyl}-3-methylpyrido[3,4-d]pyrimidin-4(3H)-one 6-Chloro-2-{4-[(1-cyclobutylpiperidin-4-yl)oxy]phenyl}-3-methylpyrido[3,4-d]pyrimidin-4(3H)-one (40.8 mg, 0.096 mmol) produced in Example 30 and triethylamine (77 μL, 0.48 mmol) were dissolved in ethyl acetate (0.5 mL), and 10% palladium-carbon (10 mg) was added thereto and stirred in a hydrogen atmosphere at room temperature for 1 hour. The reaction solution was filtered through Celite, then the Celite was washed with ethyl acetate, and the mother liquid was concentrated. The residue was purified through silica gel thin-layer chromatography (chloroform/methanol=9/1) to obtain the entitled compound (5.6 mg, 15%) as a pale yellow solid. The resulting compound was recrystallized from ethanol-water to give a colorless solid (m.p. 147.0-148.0° C.).

$^1$H-NMR (400 MHz, CD$_3$OD) δ: 1.70-1.78 (2H, m), 1.78-1.88 (2H, m), 1.88-1.98 (2H, m), 2.02-2.14 (4H, m), 2.22-2.34 (2H, m), 2.62-2.74 (2H, m), 2.83 (1H, quint., J=8.2 Hz), 3.53 (3H, s), 4.53-4.60 (1H, m), 7.12 (2H, d, J=9.0 Hz), 7.63 (2H, d, J=9.0 Hz), 8.10 (1H, d, J=5.1 Hz), 8.63 (1H, d, J=5.1 Hz), 9.01 (1H, s)

Example 64

2-{4-[(1-Cyclopentylpiperidin-4-yl)oxy]phenyl}-3-methylpyrido[3,4-d]pyrimidin-4(3H)-one 6-Chloro-2-{4-[(1-cyclopentylpiperidin-4-yl)oxy]phenyl}-3-methylpyrido[3,4-d]pyrimidin-4(3H)-one (11 mg, 0.025 mmol) produced in Example 30 and triethylamine (17 μL, 0.15 mmol) were dissolved in ethyl acetate (0.5 mL), and 10% palladium-carbon (3 mg) was added thereto and stirred in a hydrogen atmosphere at room temperature for 15 hours. The reaction solution was filtered through Celite, then the Celite was washed with ethyl acetate, and the mother liquid was concentrated. The residue was purified through silica gel thin-layer chromatography (chloroform/methanol=9/1) to obtain the entitled compound (7.3 mg, 71%) as a pale brown solid.

$^1$H-NMR (400 MHz, CD$_3$OD) δ: 1.39-1.50 (2H, m), 1.55-1.66 (2H, m), 1.67-1.78 (2H, m), 1.80-1.98 (4H, m), 2.04-2.13 (2H, m), 2.40-2.52 (2H, m), 2.61 (1H, quint., J=7.8 Hz), 2.82-2.93 (2H, m), 3.53 (3H, s), 4.52-4.59 (1H, m), 7.13 (2H, d, J=8.6 Hz), 7.63 (2H, d, J=8.6 Hz), 8.09 (1H, d, J=5.5 Hz), 8.63 (1H, d, J=5.5 Hz), 9.01 (1H, d, J=0.8 Hz)

Example 65

2-{4-[(1-Cyclobutylpiperidin-4-yl)oxy]phenyl}-7-(2-fluoroethyl)-3-methyl-3,7-dihydropyrido[3,4-d]pyrimidine-4,8-dione (1) Production of 2-{4-[(1-cyclobutylpiperidin-4-yl)oxy]phenyl}-3-methyl-3,7-dihydropyrido[3,4-d]pyrimidine-4,8-dione:

2-{4-[(1-Cyclobutylpiperidin-4-yl)oxy]phenyl}-8-methoxy-3-methylpyrido[3,4-d]pyrimidin-4(3H)-one (500 mg, 1.19 mmol) was dissolved in dichloromethane (1 ml), and with stirring at 0° C., boron trifluoride (1.0 M in CH$_2$Cl$_2$, 3.9 mL) was added thereto, then gradually heated up to room temperature, and stirred at that temperature for 20 hours. The reaction solution was diluted with ethyl acetate, and with cooling with ice, this was poured into aqueous 1 N sodium hydroxide solution, and extracted with ethyl acetate. The organic layer was washed with saturated saline water, and dried with magnesium sulfate. The solvent was evaporated off, and the residue was purified through silica gel column chromatography (chloroform/methanol=1/0 to 9/1 and its polarity was stepwise increased up to 5/1) to obtain the intended compound (300 mg, 62%) as a pale yellow solid.

(2) Production of 2-{4-[(1-cyclobutylpiperidin-4-yl)oxy]phenyl}-7-(2-fluoroethyl)-3-methyl-3,7-dihydropyrido[3,4-d]pyrimidine-4,8-dione:

2-{4-[(1-Cyclobutylpiperidin-4-yl)oxy]phenyl}-3-methyl-3,7-dihydropyrido[3,4-d]pyrimidine-4,8-dione (24 mg, 0.06 mmol) and potassium carbonate (33 mg, 0.24 mmol) were stirred in DMF (0.5 mL) at room temperature, then 2-fluoroethyl tosylate (40 mg, 0.18 mmol) was dropwise added thereto and stirred at room temperature for 20 hours. The reaction solution was diluted with ethyl acetate, washed with water and saturated saline water in that order, and the organic layer was dried with magnesium sulfate. The solvent was evaporated off, and the residue was purified through silica gel thin-layer chromatography (chloroform/methanol=9/1) to obtain the intended compound (1.0 mg, 4%) as a pale yellow solid.

$^1$H-NMR (400 MHz, CDCl$_3$) δ: 1.76-1.66 (2H, m), 1.81-1.98 (4H, m), 2.00-2.11 (4H, m), 2.19-2.32 (2H, m), 2.58-2.69 (2H, m), 2.72-2.84 (1H, m), 3.58 (3H, s), 4.34 (2H, dt, J=27.3, 4.6 Hz), 4.39-4.47 (1H, m), 4.77 (2H, dt, J=47.5, 4.6 Hz), 6.89 (1H, d, J=7.3 Hz), 6.98 (2H, d, J=8.8 Hz), 7.28 (1H, d, J=7.3 Hz), 7.55 (2H, d, J=8.8 Hz)

Example 66

2-{4-[(1-Cyclopentylpiperidin-4-yl)oxy]phenyl}-7-(2-fluoroethyl)-3-methyl-3,7-dihydropyrido[3,4-d]pyrimidine-4,8-dione The entitled compound was obtained according to the method of Example 65 but starting from 2-{4-[(1-cyclopentylpiperidin-4-yl)oxy]phenyl}-8-methoxy-3-methylpyrido[3,4-d]pyrimidin-4(3H)-one.

$^1$H-NMR (400 MHz, CDCl$_3$) δ: 1.37-1.50 (2H, m), 1.54-1.77 (5H, m), 1.80-1.94 (4H, m), 1.99-2.11 (2H, m), 2.35-2.47 (1H, m), 2.51-2.62 (1H, m), 2.77-2.87 (2H, m), 3.58 (3H, s), 4.34 (2H, dt, J=27.2, 4.4 Hz), 4.39-4.46 (1H, m), 4.77 (2H, dt, J=47.2, 4.4 Hz), 6.89 (1H, d, J=7.3 Hz), 6.99 (2H, d, J=8.8 Hz), 7.29 (1H, d, J=7.3 Hz), 7.55 (2H, d, J=8.8 Hz)

Example 67

2-{4-[(1-Cyclobutylpiperidin-4-yl)oxy]phenyl}-8-(difluoromethoxy)-3-methylpyrido[3,4-d]pyrimidin-4(3H)-one 2-{4-[(1-Cyclobutylpiperidin-4-yl)oxy]phenyl}-3-methyl-3,7-dihydropyrido[3,4-d]pyrimidine-4,8-dione (50 mg, 0.123 mmol), sodium chlorodifluoroacetate (19 mg, 0.13 mmol) and potassium carbonate (34 mg, 0.25 mmol) were heated under reflux in acetonitrile (1 mL) for 6 hours. Sodium chlorodifluoroacetate (19 mg, 0.13 mmol) and acetonitrile (1 mL) were further added to the reaction solution and heated under reflux for 18 hours. After restored to room temperature, the reaction solution was diluted with ethyl acetate, washed with water and saturated saline water in that order, and the organic layer was dried with magnesium sulfate. The solvent was evaporated off, and the residue was purified through silica gel thin-layer chromatography (chloroform/methanol=9/1) to obtain a low-polar compound, 2-{4-[(1-cyclobutylpiperidin-4-yl)oxy]phenyl}-8-(difluoromethoxy)-3-methylpyrido[3,4-d]pyrimidin-4(3H)-one (4.8 mg, 9%), and a high-polar compound, 2-{4-[(1-cyclobutylpiperidin-4-yl)oxy]phenyl}-7-(difluoromethyl)-3-methyl-3,7-dihydropyrido[3,4-d]pyrimidine-4,8-dione (11.4 mg, 21%) as a pale yellow solid.

$^1$H-NMR (400 MHz, CDCl$_3$) δ: 1.65-1.78 (2H, m), 1.80-1.96 (4H, m), 1.98-2.11 (4H, m), 2.14-2.28 (2H, m), 2.56-2.69 (2H, m), 2.75 (1H, quint., J=7.6 Hz), 3.59 (3H, s), 4.39-4.48 (1H, m), 7.02 (2H, dt, J=9.4, 2.4 Hz), 7.56 (2H, dt, J=9.4, 2.4 Hz), 7.61 (1H, t, J=72.2 Hz), 7.88 (1H, d, J=5.4 Hz), 8.16 (1H, d, J=5.4 Hz)

Example 68

2-{4-[(1-Cyclobutylpiperidin-4-yl)oxy]phenyl}-7-(difluoromethyl)-3-methyl-3,7-dihydropyrido[3,4-d]pyrimidine-4,8-dione The entitled compound was produced as in Example 67.
$^1$H-NMR (400 MHz, CDCl$_3$) δ: 1.62-1.80 (2H, m), 1.80-1.95 (4H, m), 1.96-2.11 (4H, m), 2.12-2.27 (2H, m), 2.55-2.68 (2H, m), 2.75 (1H, quint., J=7.8 Hz), 3.59 (3H, s), 4.37-4.45 (1H, m), 6.99-7.01 (3H, m), 7.40 (1H, d, J=7.3 Hz), 7.54 (2H, d, J=8.8 Hz), 7.80 (1H, t, J=60.0 Hz)

Example 69

3-Methyl-2-[4-(3-piperidin-1-ylpropoxy)-phenyl]pyrido[3,4-d]pyrimidin-4(3H)-one

6-Chloro-3-methyl-2-[4-(3-piperidin-1-ylpropoxy)phenyl]pyrido[3,4-d]pyrimidin-4(3H)-one (42.0 mg, 0.101 mmol) produced in Example 18 was dissolved in ethyl acetate (1 mL), and 10% palladium-carbon (11 mg, 0.0101 mmol) was added thereto and stirred in a hydrogen atmosphere at room temperature for 24 hours. The reaction solution was filtered through Celite, then the Celite was washed with ethyl acetate, and the mother liquid was concentrated. The residue was purified through silica gel column chromatography (chloroform/methanol=3/1) to obtain the intended compound (16.7 mg, 44%) as a colorless solid.
$^1$H-NMR (400 MHz, CD$_3$OD) δ: 1.58-1.53 (2H, m), 1.70 (4H, quint., J=5.1 Hz), 2.10 (2H, td, J=5.9, 16.1 Hz), 2.57-2.67 (4H, m), 2.69 (2H, t, J=7.3 Hz), 3.56 (3H, s), 4.16 (2H, t, J=6.2 Hz), 7.13 (2H, d, J=8.8 Hz), 7.65 (2H, d, J=8.1 Hz), 8.12 (1H, d, J=6.6 Hz), 8.65 (1H, d, J=5.9 Hz), 9.03 (1H, s)

Example 70

3-Methyl-2-[3-(3-piperidin-1-ylpropoxy)-phenyl]-6-methylsulfonylamino-4(3H)-quinazolinone (1) Production of 3-methyl-6-nitro-2-[3-(3-piperidin-1-ylpropoxy)phenyl]-4(3H)-quinazolinone:
The intended compound was obtained according to the method of Example 15 but using 2-amino-5-nitrobenzoic acid, methylamine and 3-(3-piperidin-1-ylpropoxy)benzaldehyde.
$^1$H-NMR (400 MHz, DMSO-d$_6$) δ: 1.42-1.33 (2H, m), 1.43-1.61 (4H, m), 1.83-1.97 (2H, m), 2.22-2.49 (6H, m), 3.39 (3H, s), 4.06 (2H, t, J=6.6 Hz), 7.12 (1H, dd, J=2.9, 8.8 Hz), 7.22 (1H, d, J=8.1 Hz), 7.24 (1H, d, J=2.2 Hz), 7.45 (1H, t, J=8.1 Hz), 7.86 (1H, d, J=8.8 Hz), 8.55 (1H, dd, J=8.8, 2.9 Hz), 8.86 (1H, d, J=2.2 Hz)
(2) Production of 6-amino-3-methyl-2-[3-(3-piperidin-1-ylpropoxy)phenyl]-4(3H)-quinazolinone:
3-Methyl-6-nitro-2-[3-(3-piperidin-1-ylpropoxy)phenyl]-4(3H)-quinazolinone (105 mg, 0.248 mmol) was dissolved in methanol (3 mL), and 10% palladium-carbon (26.4 mg, 0.0248 mmol) was added thereto and stirred in a hydrogen atmosphere at room temperature for 4 days. The reaction solution was filtered through Celite, the Celite was washed with ethyl acetate, and the mother liquid was concentrated. The residue was purified through silica gel column chromatography (chloroform/methanol=3/1) to obtain the intended compound (42.8 mg, 44%) as a yellow solid.
(3) Production of 3-methyl-2-[3-(3-piperidin-1-ylpropoxy)phenyl]-6-methylsulfonylamino-4(3H)-quinazolinone:
A mixture of 6-amino-3-methyl-2-[3-(3-piperidin-1-ylpropoxy)phenyl]-4(3H)-quinazolinone (13.2 mg, 0.0336 mmol), triethylamine (20 mg, 0.201 mmol) and THF (0.3 mL) was stirred at 0° C., and still at 0° C., methanesulfonyl chloride (15.4 mg, 0.134 mmol) was added thereto. The reaction solution was stirred at room temperature for 1 hour, then aqueous 1 N sodium hydroxide solution (0.3 mL) was added thereto and further stirred for 1 hour. The reaction solution was diluted with ethyl acetate, poured into saturated saline water, extracted with ethyl acetate, and the organic layer was dried with magnesium sulfate. The solvent was evaporated off, and the residue was purified through silica gel column chromatography (chloroform/methanol=5/1) to obtain the intended compound (10.9 mg, 67%) as a yellow solid.
$^1$H-NMR (400 MHz, CD$_3$OD) δ: 1.62-1.51 (2H, m), 1.68-1.77 (4H, m), 2.06-2.20 (2H, m), 2.63-2.99 (6H, m), 3.05 (3H, s), 3.46 (3H, s), 4.13 (2H, t, J=5.9 Hz), 7.12-7.14 (1H, m), 7.17-7.19 (2H, m), 7.47 (1H, t, J=8.1 Hz), 7.63-7.69 (2H, m), 8.08 (1H, d, J=2.2 Hz)
Compounds of Examples 71 to 76 can be produced according to the method of Example 70 or a method similar to it or a combination of the method with an ordinary method, but starting from the corresponding nitrobenzoic acid, aromatic aldehyde such as 4-(3-piperidin-1-ylpropoxy)benzaldehyde, amine, acyl halide or alkylsulfonyl chloride.

Example 71

3-Methyl-2-[3-(3-piperidin-1-ylpropoxy)-phenyl]-7-methylsulfonylamino-4(3H)-quinazolinone The entitled compound was obtained according to the method of Example 70 but starting from 2-amino-4-nitrobenzoic acid, methylamine and 3-(3-piperidin-1-ylpropoxy)benzaldehyde and methanesulfonyl chloride.
$^1$H-NMR (400 MHz, CD$_3$OD) δ: 1.57-1.46 (2H, m), 1.66 (4H, quint., J=5.9 Hz), 2.05 (2H, dt, J=15.4, 6.6 Hz), 2.53-2.65 (4H, m), 2.67 (2H, t, J=8.1 Hz), 3.07 (3H, s), 3.43 (3H, s), 4.10 (2H, t, J=5.9 Hz), 7.10-7.18 (2H, m), 7.17 (1H, s), 7.33 (1H, dd, J=8.1, 2.2 Hz), 7.45 (1H, t, J=8.1 Hz), 7.47 (1H, s), 8.15 (1H, d, J=8.8 Hz)

Example 72

3-Methyl-7-nitro-2-[3-(3-piperidin-1-ylpropoxy)phenyl]-4(3H)-quinazolinone

The entitled compound was obtained according to the method of Example 70 but starting from 2-amino-4-nitrobenzoic acid, methylamine and 3-(3-piperidin-1-ylpropoxy)benzaldehyde.
$^1$H-NMR (400 MHz, DMSO-d$_6$) δ: 1.40-1.33 (2H, m), 1.44-1.51 (4H, m), 1.85-1.92 (2H, m), 2.26-2.45 (6H, m), 3.37 (3H, s), 4.05 (2H, t, J=6.2 Hz), 7.11 (1H, dd, J=1.5, 8.1 Hz), 7.21 (1H, d, J=8.1 Hz), 7.23 (1H, d, J=2.2 Hz), 7.45 (1H, t, J=8.1 Hz), 8.25 (1H, dd, J=2.2, 8.8 Hz), 8.38 (1H, br s), 8.40 (1H, d, J=7.3 Hz)

Example 73

3-Methyl-7-methylsulfonylamino-2-[4-(3-pyrrolidin-1-ylpropoxy)phenyl]-4(3H)-quinazolinone The entitled compound was obtained according to the method of Example 70 but starting from 2-amino-4-nitrobenzoic acid, methylamine and 4-(3-pyrrolidin-1-ylpropoxy) benzaldehyde and methanesulfonyl chloride.

$^1$H-NMR (400 MHz, CD$_3$OD) δ: 1.89-1.80 (4H, m), 2.03-2.10 (2H, m), 2.60-2.68 (4H, m), 2.73 (2H, t, J=7.8 Hz), 2.99 (3H, s), 3.45 (3H, s), 4.13 (2H, t, J=6.1 Hz), 7.09 (2H, d, J=9.0 Hz), 7.22 (1H, dd, J=1.6, 8.6 Hz), 7.40 (1H, d, J=1.6 Hz), 7.56 (2H, d, J=9.0 Hz), 8.04 (1H, d, J=8.6 Hz)

Example 74

3-Methyl-6-methylsulfonylamino-2-[4-(3-pyrrolidin-1-ylpropoxy)phenyl]-4(3H)-quinazolinone The entitled compound was obtained according to the method of Example 70 but starting from 2-amino-5-nitrobenzoic acid, methylamine and 4-(3-pyrrolidin-1-ylpropoxy)benzaldehyde and methanesulfonyl chloride.

$^1$H-NMR (400 MHz, CD$_3$OD) δ: 1.87-1.80 (4H, m), 2.02-2.09 (2H, m), 2.59-2.63 (4H, m), 2.70 (2H, t, J=7.8 Hz), 2.92 (3H, s), 3.47 (3H, s), 4.13 (2H, t, J=6.1 Hz), 7.09 (2H, d, J=8.6 Hz), 7.48-7.50 (2H, m), 7.55 (2H, d, J=8.6 Hz), 7.94 (1H, s)

Example 75

6-Acetylamino-3-methyl-2-[4-(3-piperidin-1-ylpropoxy)phenyl]-4(3H)-quinazolinone The entitled compound was obtained according to the method of Example 70 but starting from 2-amino-5-nitrobenzoic acid, methylamine and 4-(3-piperidin-1-ylpropoxy)benzaldehyde and acetyl chloride.

$^1$H-NMR (400 MHz, CD$_3$OD) δ: 1.61-1.55 (2H, m), 1.74 (4H, quint., J=8.8 Hz), 2.13 (2H, td, J=5.9, 16.1 Hz), 2.20 (3H, s), 2.73-2.75 (4H, m), 2.80 (2H, t, J=8.1 Hz), 3.51 (3H, s), 4.16 (2H, t, J=5.9 Hz), 7.12 (2H, d, J=8.8 Hz), 7.60 (2H, d, J=8.8 Hz), 7.63 (1H, d, J=8.8 Hz), 7.97 (1H, dd, J=8.8, 2.2 Hz), 8.51 (1H, d, J=2.9 Hz)

Example 76

3-Methyl-2-[4-(3-piperidin-1-ylpropoxy)phenyl]-6-trifluoromethylcarbonylamino-4(3H)-quinazolinone The entitled compound was obtained according to the method of Example 70 but starting from 2-amino-5-nitrobenzoic acid, methylamine and 4-(3-piperidin-1-ylpropoxy)benzaldehyde and trifluoroacetic anhydride.

$^1$H-NMR (400 MHz, CDCl$_3$) δ: 1.43-1.52 (2H, m), 1.54-1.67 (4H, m), 2.00-2.09 (2H, m), 2.41-2.60 (6H, m), 3.55 (3H, s), 4.09 (2H, t, J=6.3 Hz), 7.03 (2H, d, J=8.8 Hz), 7.52 (2H, d, J=8.8 Hz), 7.79 (1H, d, J=8.8 Hz), 8.20 (1H, td, J=2.1, 8.8 Hz), 8.24-8.32 (1H, m), 8.33 (1H, t, J=2.1 Hz)

Example 77

3-Methyl-2-[2-methyl-4-(3-pyrrolidin-1-ylpropoxy)phenyl]-4(3H)-quinazolinone (1) Production of 2-(4-hydroxy-2-methylphenyl)-3-methyl-4 (3H)-quinazolinone:

The entitled compound was obtained according to the method of Example 1-(1), 1-(2) and 1-(3) but using anthranilic acid, methylamine and 2-methyl-4-methoxybenzaldehyde.

(2) Production of 3-methyl-2-[2-methyl-4-(3-pyrrolidin-1-ylpropoxy)phenyl]-4(3H)-quinazolinone:

2-(4-Hydroxy-2-methylphenyl)-3-methyl-4(3H)-quinazolinone (100 mg, 0.376 mmol), 1-(3-bromopropyl)piperidinium bromide (123 mg, 0.451 mmol) and potassium carbonate (208 mg, 1.50 mmol) were mixed in DMF (2 ml), and stirred at 80° C. for 3 hours. The reaction solution was diluted with ethyl acetate, washed with aqueous 1 N sodium hydroxide solution and saturated saline in that order, and the organic layer was dried with magnesium sulfate. The solvent was evaporated off, and the residue was purified through silica gel column chromatography (chloroform/methanol=5/1) to obtain the intended compound (88 mg, 62 mg) as a pale yellow solid (m.p. 89.0-94.0° C.).

$^1$H-NMR (400 MHz, CDCl$_3$) δ: 1.84-1.80 (4H, m), 2.01-2.08 (2H, m), 2.22 (3H, s), 2.55-2.59 (4H, m), 2.67 (2H, t, J=7.4 Hz), 3.36 (3H, s), 4.08 (2H, t, J=6.5 Hz), 6.84-6.87 (2H, m), 7.22-7.25 (1H, m), 7.51 (1H, ddd, J=2.0, 6.3, 7.8 Hz), 7.73-7.79 (2H, m), 8.34 (1H, dd, J=8.6, 0.8 Hz)

Compounds of Examples 78 to 84 can be produced according to the method of Example 77 or a method similar to it or a combination of the method with an ordinary method, but starting from the corresponding aminobenzoic acid, benzaldehyde, amine, 1-(3-bromopropyl)piperidinium bromide or 1-(3-bromopropyl)pyrrolidinium bromide.

Example 78

3-Methyl-2-[2-fluoro-4-(3-pyrrolidin-1-ylpropoxy)phenyl]-4(3H)-quinazolinone

The entitled compound was obtained according to the method of Example 77 but starting from anthranilic acid, methylamine, 2-fluoro-4-methoxybenzaldehyde and 1-(3-bromopropyl)piperidinium bromide.

$^1$H-NMR (400 MHz, CDCl$_3$) δ: 1.84-1.79 (4H, m), 2.05 (2H, quint., J=6.7 Hz), 2.51-2.60 (4H, m), 2.65 (2H, t, J=7.4 Hz), 3.50 (3H, d, J=1.6 Hz), 4.10 (2H, t, J=6.3 Hz), 6.75 (1H, dd, J=12.1, 2.3 Hz), 6.86 (1H, dd, J=8.6, 2.3 Hz), 7.47 (1H, t, J=8.4 Hz), 7.51 (1H, ddd, J=2.0, 6.7, 7.8 Hz), 7.72-7.79 (1H, m), 7.74 (1H, d, J=2.0 Hz), 8.34 (1H, d, J=8.2 Hz)

Example 79

6-Bromo-3-methyl-2-[3-methoxy-4-(3-pyrrolidin-1-ylpropoxy)phenyl]-4(3H1)-quinazolinone The entitled compound was obtained according to the method of Example 77 but using 5-bromoanthranilic acid, methylamine, 4-hydroxy-3-methoxybenzaldehyde and 1-(3-bromopropyl)pyrrolidinium bromide.

$^1$H-NMR (400 MHz, CDCl$_3$) δ: 1.85-1.79 (4H, m), 2.09-2.16 (2H, m), 2.55-2.61 (4H, m), 2.66-2.71 (2H, m), 3.53 (3H, s), 3.92 (3H, s), 4.17 (2H, t, J=6.7 Hz), 7.02 (1H, d, J=8.6 Hz), 7.08-7.12 (2H, m), 7.61 (1H, d, J=8.6 Hz), 7.82 (1H, dd, J=8.6, 2.3 Hz), 8.45 (1H, d, J=2.3 Hz)

Example 80

6-Bromo-3-methyl-2-[2-methoxy-4-(3-pyrrolidin-1-ylpropoxy)phenyl]-4(3H)-quinazolinone The entitled compound was obtained according to the method of Example 77 but using 5-bromoanthranilic acid, methylamine, 4-hydroxy-2-methoxybenzaldehyde and 1-(3-bromopropyl)pyrrolidinium bromide.

$^1$H-NMR (400 MHz, CDCl$_3$) δ: 1.93-1.83 (4H, m), 2.07-2.14 (2H, m), 2.62-2.80 (6H, m), 3.41 (3H, s), 3.80 (3H, s), 4.10 (2H, t, J=6.3 Hz), 6.54 (1H, d, J=2.0 Hz), 6.62 (1H, dd,

J=8.4, 2.2 Hz), 7.33 (1H, d, J=8.6 Hz), 7.60 (1H, d, J=8.6 Hz), 7.81 (1H, dd, J=8.6, 2.3 Hz), 8.46 (1H, d, J=2.3 Hz)

Example 81

2-[2-Methoxy-4-(3-pyrrolidin-1-ylpropoxy)phenyl]-3-methylpyrido[2,3-d]pyrimidin-4(3H)-one The entitled compound was obtained according to the method of Example 77 but using 2-aminonicotinic acid, methylamine, 2-methoxy-4-hydroxybenzaldehyde and 1-(3-bromopropyl)pyrrolidinium bromide.

$^1$H-NMR (CDCl$_3$) δ: 1.83-1.88 (4H, m), 2.09 (2H, q, J=7.0 Hz), 2.59-2.69 (4H, m), 2.73 (2H, t, J=7.0 Hz), 3.45 (3H, s), 3.80 (3H, s), 4.11 (2H, t, J=6.3 Hz), 6.53 (1H, d, J=2.3 Hz), 6.62 (1H, dd, J=2.3, 8.6 Hz), 7.43 (1H, dd, J=4.7, 7.8 Hz), 7.45 (1H, d, J=8.6 Hz), 8.65 (1H, dd, J=7.8, 2.0 Hz), 8.98 (1H, dd, J=2.0, 4.7 Hz)

Example 82

8-Methoxy-3-methyl-2-[4-(3-pyrrolidin-1-ylpropoxy)phenyl]-quinazolin-4(3H)-one The entitled compound was obtained according to the method of Example 77 but using 2-amino-3-methoxybenzoic acid, methylamine, 4-hydroxybenzaldehyde and 1-(3-bromopropyl)pyrrolidinium bromide.

$^1$H-NMR (400 MHz, CD$_3$OD) δ: 1.90-1.94 (4H, m), 2.09-2.16 (2H, m), 2.83-2.85 (4H, br m), 2.91 (2H, t, J=7.8 Hz), 3.49 (3H, s), 3.96 (3H, s), 4.16 (2H, t, J=6.1 Hz), 7.10 (2H, d, J=8.6 Hz), 7.36 (1H, d, J=7.4 Hz), 7.48 (1H, t, J=8.0 Hz), 7.60 (2H, d, J=8.6 Hz), 7.80 (1H, d, J=7.8 Hz)

Example 83

3-Allyl-2-[4-(3-pyrrolidin-1-ylpropoxy)phenyl]pyrido[2,3-d]pyrimidin-4(3H)-one The entitled compound was obtained according to the method of Example 77 but using 2-aminonicotinic acid, allylamine, 4-hydroxybenzaldehyde and 1-(3-bromopropyl)pyrrolidinium bromide.

$^1$H-NMR (400 MHz, DMSO-d$_6$) δ: 1.88-1.91 (4H, m), 2.10 (2H, s), 3.32-3.35 (6H, m), 4.14 (2H, t, J=6.3 Hz), 4.55 (2H, d, J=5.1 Hz), 4.89 (1H, d, J=18.0 Hz), 5.11 (1H, d, J=11.0 Hz), 5.81-5.86 (1H, m), 7.09 (2H, d, J=9.0 Hz), 7.59-7.60 (3H, m), 8.57 (1H, t, J=3.9 Hz), 8.99 (1H, dd, J=4.7, 2.0 Hz).

Example 84

2-[2-Methoxy-4-(3-piperidin-1-ylpropoxy)phenyl]-3-methylpyrido[2,3-d]pyrimidin-4(3H)-one The entitled compound was obtained according to the method of Example 77 but using 2-aminonicotinic acid, methylamine, 2-methoxy-4-hydroxybenzaldehyde and 1-(3-bromopropyl)pyrrolidinium bromide.

$^1$H-NMR (400 MHz, CDCl$_3$) δ: 1.43-1.49 (2H, m), 1.56-1.65 (4H, br m), 1.98-2.07 (2H, m), 2.43 (4H, br s), 2.51 (2H, t, J=7.6 Hz), 3.45 (3H, s), 3.80 (3H, s), 4.08 (2H, t, J=6.3 Hz), 6.53 (1H, d, J=2.0 Hz), 6.62 (1H, dd, J=8.4, 2.2 Hz), 7.41-7.46 (2H, m), 8.65 (1H, dd, J=7.8, 2.0 Hz), 8.98 (1H, dd, J=4.7, 2.0 Hz)

Example 85

3-Methyl-2-[2-methyl-4-(1-cyclobutyl-4-piperidinyloxy)phenyl]4(3H)-quinazolinone (1) Production of 3-methyl-2-[2-methyl-4-(4-piperidinyloxy)phenyl]-4(3H)-quinazolinone:

2-(4-Hydroxy-2-methylphenyl)-3-methyl-4(3H)-quinazolinone (200 mg, 0.751 mmol), tert-butyl 4-hydroxytetrahydro-1(2H)-pyridinecarboxylate (227 mg, 1.12 mmol) and triphenyl phosphine (295 mg, 1.12 mmol) were dissolved in THF (2.0 mL), and with stirring at 0° C., diisopropyl azodicarboxylate (228 mg, 1.12 mmol) was added thereto and stirred for 24 hours. The reaction solution was diluted with ethyl acetate, poured into saturated saline water, extracted with ethyl acetate, and the organic layer was dried with magnesium sulfate. The solvent was evaporated off, and the resulting residue was dissolved in chloroform (3 mL), trifluoroacetic acid (2 mL) was added thereto, and stirred at room temperature for 2 hours. The reaction solution was diluted with ethyl acetate, washed with aqueous 1 N sodium hydroxide solution and saturated saline water, and the organic layer was dried with magnesium sulfate. The solvent was evaporated off, and the residue was purified through silica gel column chromatography (chloroform/methanol=1/1) to obtain the intended compound (245 mg, 93%) as a colorless solid.

(2) Production of 3-methyl-2-[2-methyl-4-(1-cyclobutyl-4-piperidinyloxy)phenyl]-4(3H)-quinazolinone:

3-Methyl-2-[2-methyl-4-(4-piperidinyloxy)phenyl]-4(3H)-quinazolinone (98.8 mg, 0.283 mmol), cyclobutanone (39.7 mg, 0.566 mmol), zinc chloride (77 mg, 0.566 mmol) and sodium cyanoborohydride (36 mg, 0.566 mmol) were dissolved in methanol, and stirred at room temperature for 12 hours. The reaction solution was diluted with ethyl acetate, washed with aqueous 1 N sodium hydroxide solution and saturated saline water in that order, and the organic layer was dried with magnesium sulfate. The solvent was evaporated off, and the residue was purified through silica gel column chromatography (chloroform/methanol=3/1) to obtain the intended compound (47 mg, 41%) as a colorless solid. The obtained compound was further purified through reversed-phase liquid chromatography (acetonitrile-water) to give a colorless solid (m.p. 121.0-125.0° C.).

$^1$H-NMR (400 MHz, CDCl$_3$) δ: 1.75-1.64 (2H, m), 1.80-1.95 (4H, m), 1.98-2.09 (4H, m), 2.16-2.24 (2H, m), 2.21 (3H, s), 2.57-2.67 (2H, m), 2.71-2.79 (1H, m), 3.37 (3H, s), 4.36-4.42 (1H, m), 6.84-6.86 (2H, m), 7.22-7.24 (1H, m), 7.52 (1H, ddd, J=1.2, 6.3, 8.2 Hz), 7.72-7.79 (2H, m), 8.34 (1H, td, J=0.8, 7.8 Hz)

Compounds of Examples 86 to 104 can be produced according to the method of Example 85 or a method similar to it or a combination of the method with an ordinary method, but starting from the corresponding aminobenzoic acid, aromatic aldehyde, amine, tert-butyl 4-hydroxytetrahydro-1 (2H)-pyridinecarboxylate and alkylketone or acetal.

Example 86

3-Methyl-2-[2-methyl-4-(1-cyclopentyl-4-piperidinyloxy)-phenyl]-4(3H)-quinazolinone The entitled compound was obtained according to the method of Example 85 but using anthranilic acid, methylamine, 2-methyl-4-methoxybenzaldehyde, tert-butyl 4-hydroxytetrahydro-1(2H)-pyridinecarboxylate, and cyclopentanone.

¹H-NMR (400 MHz, CDCl₃) δ: 1.49-1.39 (2H, m), 1.53-1.62 (2H, m), 1.67-1.74 (2H, m), 1.82-1.94 (4H, m), 1.99-2.09 (2H, m), 2.21 (3H, s), 2.33-2.43 (2H, m), 2.49-2.58 (1H, m), 2.77-2.86 (2H, m), 3.37 (3H, s), 4.34-4.43 (1H, m), 6.84-6.87 (2H, m), 7.23 (1H, d, J=9.0 Hz), 7.52 (1H, ddd, J=1.6, 6.3, 8.2 Hz), 7.72-7.79 (2H, m), 8.34 (1H, dd, J=1.6, 8.2 Hz)

Example 87

3-Methyl-2-[2-methyl-4-(1-cyclohexyl-4-piperidinyloxy)-phenyl]-4(3H)-quinazolinone The entitled compound was obtained according to the method of Example 85 but using anthranilic acid, methylamine, 2-methyl-4-methoxybenzaldehyde, tert-butyl 4-hydroxytetrahydro-1(2H)-pyridinecarboxylate, and cyclohexanone.

¹H-NMR (400 MHz, CDCl₃) δ: 1.31-1.05 (6H, m), 1.78-1.91 (6H, m), 1.99-2.07 (2H, m), 2.21 (3H, s), 2.29-2.37 (1H, m), 2.44-2.51 (2H, m), 2.81-2.89 (2H, m), 3.37 (3H, s), 4.31-4.40 (1H, m), 6.84-6.87 (2H, m), 7.21-7.24 (1H, m), 7.51 (1H, ddd, J=2.0, 6.7, 7.8 Hz), 7.72-7.79 (2H, m), 8.34 (1H, dd, J=1.2, 7.8 Hz)

Example 88

3-Methyl-2-[4-(1-cyclobutyl-4-piperidinyloxy)-phenyl]-4(3H)-quinazolinone

The entitled compound was obtained according to the method of Example 85 but using anthranilic acid, methylamine, 4-methoxybenzaldehyde, tert-butyl 4-hydroxytetrahydro-1(2H)-pyridinecarboxylate, and cyclobutanone. The obtained compound was further purified through reversed-phase high-performance liquid chromatography (acetonitrile-water) to give a colorless solid (m.p. 167.8-171.2° C.).

¹H-NMR (400 MHz, CDCl₃) δ: 1.76-1.64 (2H, m), 1.83-1.95 (4H, m), 1.99-2.09 (4H, m), 2.15-2.25 (2H, m), 2.58-2.68 (2H, m), 2.75 (1H, quint., J=7.0 Hz), 3.54 (3H, s), 4.39-4.46 (1H, m), 7.02 (2H, d, J=8.6 Hz), 7.47-7.52 (1H, m), 7.50 (2H, d, J=10.0 Hz), 7.71-7.77 (2H, m), 8.32 (1H, d, J=8.6 Hz)

Example 89

3-Methyl-2-[4-(1-cyclopropyl-4-piperidinyloxy)-phenyl]-4(3H)-quinazolinone

The entitled compound was obtained according to the method of Example 85 but using anthranilic acid, methylamine, 4-methoxybenzaldehyde, tert-butyl 4-hydroxytetrahydro-1(2H)-pyridinecarboxylate, and [(1-ethoxycyclopropyl)oxy](trimethyl)silane.

¹H-NMR (400 MHz, CDCl₃) δ: 0.43-0.48 (4H, m), 1.67-1.62 (1H, m), 1.78-1.86 (2H, m), 1.97-2.03 (2H, m), 2.50-2.54 (2H, m), 2.87-2.94 (2H, m), 3.55 (3H, s), 4.40-4.45 (1H, m), 7.03 (2H, d, J=8.8 Hz), 7.47-7.51 (1H, m), 7.52 (2H, d, J=8.8 Hz), 7.72-7.77 (2H, m), 8.32 (1H, d, J=8.2 Hz)

Example 90

8-Methoxy-3-methyl-2-[4-(1-cyclobutyl-4-piperidinyloxy)-phenyl]-4(3H)-quinazolinone The entitled compound was obtained according to the method of Example 85 but using 2-amino-3-methoxybenzoic acid, methylamine, 4-methoxybenzaldehyde, tert-butyl 4-hydroxytetrahydro-1(2H)-pyridinecarboxylate, and cyclobutanone. The obtained compound was recrystallized from ethyl acetate-heptane to give a colorless acicular crystal (m.p. 201.0-204.0° C.).

¹H-NMR (400 MHz, CD₃OD) δ: 1.79-1.70 (2H, m), 1.90-1.80 (2H, m), 1.98-1.89 (2H, m), 2.03-2.13 (4H, m), 2.26-2.35 (2H, m), 2.66-2.74 (2H, m), 2.81-2.89 (1H, m), 3.50 (3H, s), 3.96 (3H, s), 4.55-4.57 (1H, m), 7.11 (2H, d, J=8.6 Hz), 7.36 (1H, d, J=8.2 Hz), 7.48 (1H, t, J=7.8 Hz), 7.59 (2H, d, J=8.6 Hz), 7.80 (1H, d, J=7.8 Hz)

Example 91

6-Methoxy-3-methyl-2-[4-(1-cyclobutyl-4-piperidinyloxy)-phenyl]-4(3H)-quinazolinone The entitled compound was obtained according to the method of Example 85 but using 2-amino-5-methoxybenzoic acid, methylamine, 4-methoxybenzaldehyde, tert-butyl 4-hydroxytetrahydro-1(2H)-pyridinecarboxylate, and cyclobutanone.

¹H-NMR (400 MHz, CD₃OD) δ: 1.80-1.70 (2H, m), 1.92-1.81 (2H, m), 2.00-1.92 (2H, m), 2.04-2.16 (4H, m), 2.30-2.46 (2H, m), 2.68-2.82 (2H, m), 2.84-3.00 (1H, m), 3.51 (3H, s), 3.93 (3H, s), 4.55-4.62 (1H, m), 7.12 (2H, d, J=9.0 Hz), 7.43 (1H, dd, J=9.0, 2.7 Hz), 7.57 (2H, d, J=9.0 Hz), 7.62 (1H, d, J=9.0 Hz), 7.65 (1H, d, J=2.7 Hz)

Example 92

5-Methoxy-3-methyl-2-[4-(1-cyclobutyl-4-piperidinyloxy)-phenyl]-4(3H)-quinazolinone The entitled compound was obtained according to the method of Example 85 but using 2-amino-5-methoxybenzoic acid, methylamine, 4-methoxybenzaldehyde, tert-butyl 4-hydroxytetrahydro-1(2H)-pyridinecarboxylate, and cyclobutanone.

¹H-NMR (400 MHz, CD₃OD) δ: 1.80-1.71 (2H, m), 1.91-1.80 (2H, m), 1.99-1.91 (2H, m), 2.04-2.15 (4H, m), 2.26-2.42 (2H, m), 2.66-2.78 (2H, m), 2.85-2.95 (1H, m), 3.45 (3H, s), 3.97 (3H, s), 4.54-4.63 (1H, m), 7.07 (1H, d, J=8.2 Hz), 7.12 (2H, d, J=9.0 Hz), 7.23 (1H, d, J=8.2 Hz), 7.58 (2H, d, J=9.0 Hz), 7.72 (1H, t, J=8.2 Hz)

Example 93

8-Methoxy-3-methyl-2-[4-(1-cyclopropyl-4-piperidinyloxy)-phenyl]-4(3H)-quinazolinone The entitled compound was obtained according to the method of Example 85 but using 2-amino-3-methoxybenzoic acid, methylamine, 4-methoxybenzaldehyde, tert-butyl 4-hydroxytetrahydro-1(2H)-pyridinecarboxylate, and [(1-ethoxycyclopropyl)oxy](trimethyl)silane.

¹H-NMR (400 MHz, CDCl₃) δ: 0.49-0.41 (4H, m), 1.62-1.67 (1H, m), 1.76-1.86 (2H, m), 1.94-2.02 (2H, m), 2.48-2.55 (2H, m), 2.87-2.93 (2H, m), 3.54 (3H, s), 3.99 (3H, s), 4.39-4.44 (1H, m), 7.00 (2H, d, J=8.6 Hz), 7.19 (1H, d, J=7.8 Hz), 7.42 (1H, t, J=8.2 Hz), 7.52 (2H, d, J=8.6 Hz), 7.90 (1H, d, J=7.8 Hz)

Example 94

5-Methoxy-3-methyl-2-[4-(1-cyclopropyl-4-piperidinyloxy)-phenyl]-4(3H)-quinazolinone The entitled compound was obtained according to the method of Example 85 but using 2-amino-6-methoxybenzoic acid, methylamine, 4-methoxybenzaldehyde, tert-butyl 4-hydroxytetrahydro-1(2H)-pyridinecarboxylate, and [(1-ethoxycyclopropyl)oxy](trimethyl)silane.

¹H-NMR (400 MHz, CDCl₃) δ: 0.49-0.42 (4H, m), 1.62-1.67 (1H, m), 1.77-1.87 (2H, m), 1.95-2.04 (2H, m), 2.50-2.56 (2H, m), 2.88-2.93 (2H, m), 3.48 (3H, s), 4.03 (3H, s), 4.39-4.45 (1H, m), 6.90 (1H, d, J=8.6 Hz), 7.02 (2H, d, J=8.6 Hz), 7.30 (1H, d, J=7.8 Hz), 7.51 (2H, d, J=8.6 Hz), 7.64 (1H, t, J=8.2 Hz)

Example 95

2-{4-[{1-Cyclobutylpiperidin-4-yl)oxy]phenyl}-3,8-dimethylquinazolin-4(3H)-one

The entitled compound was obtained according to the method of Example 85 but using 2-amino-3-methylbenzoic acid, methylamine, 4-methoxybenzaldehyde, tert-butyl 4-hydroxytetrahydro-1(2H)-pyridinecarboxylate, and cyclobutanone. The obtained compound was further purified through reversed-phase liquid chromatography (acetonitrile-water) to give a colorless solid (m.p. 152.0-153.8° C.).

¹H-NMR (400 MHz, CD₃OD) δ: 1.70-1.79 (2H, m), 1.81-1.90 (2H, m), 1.90-1.99 (2H, m), 2.03-2.15 (4H, m), 2.27-2.40 (2H, m), 2.58 (3H, s), 2.67-2.78 (2H, m), 2.83-2.94 (1H, m), 3.52 (3H, s), 4.54-4.62 (1H, m), 7.11 (2H, d, J=9.0 Hz), 7.40 (1H, t, J=7.6 Hz), 7.62 (2H, d, J=9.0 Hz), 7.64-7.67 (1H, m), 8.07 (1H, dd, J=8.2, 0.8 Hz)

Example 96

7-Bromo-2-{4-[{1-cyclobutylpiperidin-4-yl)oxy]phenyl}-3-methylpyrido[3,2-d]pyrimidin-4(3H)-one The entitled compound was obtained according to the method of Example 85 but using 3-amino-5-bromopyridine-2-carboxylic acid, methylamine, 4-hydroxybenzaldehyde, tert-butyl 4-hydroxytetrahydro-1(2H)-pyridinecarboxylate, and cyclobutanone.

¹H-NMR (400 MHz, CDCl₃) δ: 1.68-1.73 (2H, m), 1.85-1.92 (4H, m), 2.00-2.09 (4H, m), 2.14-2.25 (2H, br m), 2.59-2.68 (2H, m), 2.76 (1H, quint., J=8.0 Hz), 3.61 (3H, s), 4.40-4.46 (1H, m), 7.04 (2H, d, J=8.6 Hz), 7.52 (2H, d, J=8.6 Hz), 8.23 (1H, d, J=2.3 Hz), 8.86 (1H, d, J=2.3 Hz)

Example 97

7-Bromo-2-{4-[{1-cyclopentylpiperidin-4-yl)oxy]phenyl-3-methylpyrido[3,2-d]pyrimidin-4(3H)-one The entitled compound was obtained according to the method of Example 85 but using 3-amino-5-bromopyridine-2-carboxylic acid, methylamine, 4-hydroxybenzaldehyde, tert-butyl 4-hydroxytetrahydro-1(2H)-pyridinecarboxylate, and cyclopentanone.

¹H-NMR (400 MHz, CDCl₃) δ: 1.43-1.46 (2H, m), 1.57-1.59 (2H, m), 1.71-1.74 (2H, m), 1.90-1.92 (4H, m), 2.05-2.07 (2H, m), 2.38-2.40 (2H, br m), 2.56 (1H, quint., J=7.8 Hz), 2.82-2.85 (2H, br m), 3.62 (3H, s), 4.43-4.46 (1H, m), 7.06 (2H, d, J=9.0 Hz), 7.53 (2H, d, J=9.0 Hz), 8.25 (1H, d, J=2.3 Hz), 8.88 (1H, d, J=2.3 Hz)

Example 98

2-{4-[{1-Cyclobutylpiperidin-4-yl)oxy]-2-methoxyphenyl}-3-methylpyrido[2,3-d]pyrimidin-4(3H)-one The entitled compound was obtained according to the method of Example 85 but using 2-aminonicotinic acid, methylamine, 2-methoxy-4-hydroxybenzaldehyde, tert-butyl 4-hydroxytetrahydro-1(2H)-pyridinecarboxylate, and cyclobutanone.

¹H-NMR (400 MHz, CDCl₃) δ: 1.54-1.80 (4H, m), 1.81-1.99 (3H, m), 1.99-2.13 (3H, m), 2.14-2.31 (2H, m), 2.57-2.72 (2H, m), 2.72-2.84 (1H, m), 3.46 (3H, s), 3.80 (3H, s), 4.38-4.46 (1H, m), 6.53 (1H, d, J=2.0 Hz), 6.61 (1H, dd, J=8.3, 2.0 Hz), 7.43 (1H, dd, J=7.8, 4.9 Hz), 7.44 (1H, d, J=8.3 Hz), 8.65 (1H, dd, J=7.8, 2.0 Hz), 8.98 (1H, dd, J=4.9, 2.0 Hz)

Example 99

2-{4-[{1-Cyclopentylpiperidin-4-yl)oxy]-2-methoxyphenyl}-3-methylpyrido[2,3-d]pyrimidin-4(3H)-one The entitled compound was obtained according to the method of Example 85 but using 2-aminonicotinic acid, methylamine, 2-methoxy-4-hydroxybenzaldehyde, tert-butyl 4-hydroxytetrahydro-1(2H)-pyridinecarboxylate, and cyclopentanone.

¹H-NMR (400 MHz, CDCl₃) δ: 1.34-1.80 (6H, m), 1.81-1.99 (4H, m), 1.99-2.16 (2H, m), 2.29-2.46 (2H, m), 2.48-2.65 (1H, m), 2.75-2.94 (2H, m), 3.46 (3H, s), 3.80 (3H, s), 4.36-4.47 (1H, m), 6.53 (1H, d, J=2.4 Hz), 6.61 (1H, dd, J=8.3, 2.4 Hz), 7.43 (1H, dd, J=7.8, 4.4 Hz), 7.45 (1H, d, J=8.3 Hz), 8.65 (1H, dd, J=7.8, 2.0 Hz), 8.98 (1H, dd, J=4.4, 2.0 Hz)

Example 100

2-{4-[{1-Cyclopropylpiperidin-4-yl)oxy]phenyl}-3-ethyl-8-methylquinazolin-4(3H)-one The entitled compound was obtained according to the method of Example 85 but using 2-amino-3-methylbenzoic acid, ethylamine, 4-hydroxybenzaldehyde, tert-butyl 4-hydroxytetrahydro-1(2H)-pyridinecarboxylate, and [(1-ethoxycyclopropyl)oxy](trimethyl)silane.

¹H-NMR (400 MHz, CDCl₃) δ: 0.38-0.53 (4H, m), 1.22 (3H, t, J=7.3 Hz), 1.60-1.70 (1H, m), 1.77-1.90 (2H, m), 1.96-2.08 (2H, m), 2.46-2.57 (2H, m), 2.59 (3H, s), 2.89-2.97 (2H, m), 4.10 (2H, q, J=7.3 Hz), 4.37-4.49 (1H, m), 7.02 (2H, d, J=8.8 Hz), 7.37 (1H, t, J=7.8 Hz), 7.50 (2H, d, J=8.8 Hz), 7.59 (1H, d, J=7.8 Hz), 8.17 (1H, d, J=7.8 Hz)

Example 101

2-{4-[{1-Cyclobutylpiperidin-4-yl)oxy]phenyl}-3-ethyl-8-methylquinazolin-4(3H)-one The entitled compound was obtained according to the method of Example 85 but using 2-amino-3-methylbenzoic acid, ethylamine, 4-hydroxybenzaldehyde, tert-butyl 4-hydroxytetrahydro-1(2H)-pyridinecarboxylate, and cyclobutanone.

¹H-NMR (400 MHz, CDCl₃) δ: 1.22 (3H, t, J=7.3 Hz), 1.62-1.79 (2H, m), 1.82-2.00 (4H, m), 2.01-2.15 (4H, m), 2.17-2.36 (2H, m), 2.58 (3H, s), 2.61-2.74 (2H, m), 2.74-2.88 (1H, m), 4.10 (2H, q, J=7.3 Hz), 4.39-4.50 (1H, m), 7.01 (2H, d, J=8.8 Hz), 7.36 (1H, t, J=7.8 Hz), 7.50 (2H, d, J=8.8 Hz), 7.59 (1H, d, J=7.8 Hz), 8.17 (1H, d, J=7.8 Hz)

Example 102

2-{4-[{1-Cyclopentylpiperidin-4-yl)oxy]phenyl}-3-ethyl-8-methylquinazolin-4(3H)-one The entitled compound was obtained according to the method of Example 85 but using 2-amino-3-methylbenzoic acid, ethylamine, 4-hydroxybenzaldehyde, tert-butyl 4-hydroxytetrahydro-1(2H)-pyridinecarboxylate, and cyclopentanone.

$^1$H-NMR (400 MHz, CDCl$_3$) δ: 1.23 (3H, q, J=7.3 Hz), 1.36-1.50 (2H, m), 1.50-1.67 (4H, m), 1.66-1.81 (2H, m), 1.82-2.01 (4H, m), 2.01-2.19 (2H, m), 2.23-2.50 (2H, m), 2.59 (3H, s), 2.77-2.94 (2H, m), 4.10 (2H, q, J=7.3 Hz), 4.35-4.52 (1H, m), 7.02 (2H, d, J=8.8 Hz), 7.37 (1H, t, J=7.8 Hz), 7.50 (2H, d, J=8.8 Hz), 7.59 (1H, d, J=7.8 Hz), 8.17 (1H, d, J=7.8 Hz)

Example 103

2-{4-[{1-Cyclobutylpiperidin-4-yl)oxy]-2-fluorophenyl}-3-methylquinazolin-4(3H)-one The entitled compound was obtained according to the method of Example 85 but using anthranilic acid, methylamine, 2-fluoro-4-methoxybenzaldehyde, tert-butyl 4-hydroxytetrahydro-1(2H)-pyridinecarboxylate, and cyclobutanone.

$^1$H-NMR (400 MHz, CDCl$_3$) δ: 1.52-1.66 (2H, m), 1.66-1.87 (4H, m), 1.91-2.08 (4H, m), 2.21-2.45 (2H, m), 2.62-3.10 (3H, m), 3.50 (3H, d, J=1.5 Hz), 4.48-4.59 (1H, m), 6.75 (1H, dd, J=11.7, 2.4 Hz), 6.86 (1H, dd, J=8.3, 2.4 Hz), 7.49 (1H, d, J=8.3 Hz), 7.50-7.54 (1H, m), 7.73 (1H, d, J=8.3 Hz), 7.75-7.79 (1H, m), 8.34 (1H, d, J=7.8 Hz)

Example 104

2-{4-[{1-Cyclopentylpiperidin-4-yl)oxy]-2-fluorophenyl}-3-methylquinazolin-4(3H)-one The entitled compound was obtained according to the method of Example 85 but using anthranilic acid, methylamine, 2-fluoro-4-methoxybenzaldehyde, tert-butyl 4-hydroxytetrahydro-1(2H)-pyridinecarboxylate, and cyclopentanone.

$^1$H-NMR (400 MHz, CDCl$_3$) δ: 1.65-1.80 (2H, m), 1.81-1.93 (2H, m), 1.95-2.10 (3H, m), 2.10-2.22 (3H, m), 2.23-2.61 (2H, m), 2.62-2.88 (4H, m), 2.90-3.24 (1H, m), 3.50 (3H, d, J=1.5 Hz), 4.45-4.69 (1H, m), 6.74 (1H, dd, J=11.2, 2.4 Hz), 6.85 (1H, dd, J=8.8, 2.4 Hz), 7.47-7.54 (2H, m), 7.71-7.79 (2H, m), 8.34 (1H, d, J=7.8 Hz)

Example 105

Tert-butyl 4-oxo-2-[4-(3-piperidin-1-ylpropoxy)phenyl]-[3,4H]-quinazolinecarboxylate (1) Production of 2-(4-hydroxyphenyl)-4(3H)-quinazolinone The entitled compound was obtained according to the method of Example 1-(2) but starting from 2-aminobenzamide and 4-hydroxybenzaldehyde.

(2) Production of tert-butyl 2-(4-hydroxyphenyl)-4-oxo-3(4H)-quinazolinecarboxylate 2-(4-Hydroxyphenyl)-4(3H)-quinazolinone (500 mg, 2.10 mmol), pivalic anhydride (1.15 g, 5.25 mmol), 4-dimethylaminopyridine (128 mg, 1.05 mmol) and triethylamine (212 mg, 2.1 mmol) were mixed in tetrahydrofuran (20 ml), and stirred at room temperature for 3 hours. The reaction solution was concentrated, a large quantity of methanol was added thereto and further stirred at room temperature for 10 minutes. The reaction solution was concentrated, and the residue was purified through silica gel column chromatography (hexane/ethyl acetate=5/1) to obtain the intended compound (590 mg, 70%) as a colorless solid.

(3) Production of tert-butyl 4-oxo-2-[4-(3-piperidin-1-ylpropoxy)phenyl]-[3,4H]-quinazolinecarboxylate The entitled compound was obtained according to the method of Example 77-(2) but starting from tert-butyl 2-(4-hydroxyphenyl)-4-oxo-3(4H)-quinazolinecarboxylate and 1-(3-bromopropyl)piperidinium bromide.

$^1$H-NMR (400 MHz, CDCl$_3$) δ: 1.42-1.50 (2H, br s), 1.58 (9H, s), 1.58-1.65 (4H, m), 2.08-2.19 (2H, m), 2.39-2.52 (4H, br s), 2.60 (2H, t, J=6.8 Hz), 4.73 (2H, t, J=6.8 Hz), 7.28 (2H, d, J=8.8 Hz), 7.49 (1H, t, J=6.8 Hz), 7.79 (1H, t, J=8.0 Hz), 7.94 (1H, d, J=8.4 Hz), 8.13 (1H, d, J=6.8 Hz), 8.57 (2H, d, J=8.4 Hz)

Reference Example 1

4-[(1-Cyclopentyl-4-piperidinyl)oxy]benzaldehyde (1) Production of tert-butyl 4-[4-(ethoxycarbonyl)phenoxy]tetrahydro-1(2H)-pyridinecarboxylate Ethyl 4-hydroxybenzoate (4.15 g, 25.0 mmol), tert-butyl 4-hydroxytetrahydro-1(2H)-pyridinecarboxylate (5.0 g, 25.0 mmol) and triphenyl phosphine (7.87 g, 30.0 mmol) were dissolved in tetrahydrofuran (50 mL), and with stirring at 0° C., diisopropyl azodicarboxylate (6.06 g, 30.0 mmol) was added thereto and stirred for 24 hours. The reaction solution was concentrated, and the precipitated white solid was taken out through filtration and washed with ethyl acetate. The mother liquid was washed with aqueous 1 N sodium hydroxide solution and saturated saline water in that order, and the organic layer was dried with magnesium sulfate. The solvent was evaporated off, and the residue was purified through silica gel column chromatography (hexane/ethyl acetate=9/1) to obtain the intended compound (5.45 g, 62%) as a colorless solid.

(2) Production of 4-[(1-cyclopentyl-4-piperidinyl)oxy]benzaldehyde

Tert-butyl 4-[4-(ethoxycarbonyl)phenoxy]tetrahydro-1(2H)-pyridinecarboxylate (2.0 g, 5.72 mmol) was stirred in trifluoroacetic acid (10 mL) at room temperature for 30 minutes. The reaction solution was poured into aqueous 1 N sodium hydroxide solution, and extracted with ethyl acetate. The organic layer was washed with saturated saline water, dried with magnesium sulfate, and then concentrated under reduced pressure. The resulting residue was dissolved in methanol (10 mL), and cyclopentanone (0.80 g, 11.4 mmol), zinc chloride (1.56 g, 11.4 mmol) and sodium cyanoborohydride (730 mg, 11.4 mmol) were added thereto and stirred at room temperature for 16 hours. The reaction solution was diluted with ethyl acetate, washed with aqueous 1 N sodium hydroxide solution and saturated saline water in that order, and the organic layer was dried with magnesium sulfate. The solvent was evaporated off, and the residue was dissolved in tetrahydrofuran (20 mL), and at −78° C., diisobutylaluminium hydride (1.0 M toluene solution, 17.1 mL) was dropwise added thereto. This was gradually heated up to 0° C. and stirred for 1 hour, and a large quantity of Rochelle salt and water were added thereto and further stirred at room temperature for 3 hours. The reaction solution was extracted with ethyl acetate, and the organic layer was washed with saturated saline water and dried with magnesium sulfate. The solvent was evaporated off under reduced pressure, the residue was suspended in toluene (20 mL), and manganese dioxide (5.0 g, 57 mmol) was added thereto. The reaction solution was stirred at room temperature for 50 hours, then filtered through Celite, and the Celite was washed with ethyl acetate. The mother liquid was concentrated, and the resulting residue was purified through silica gel column chromatography (chloroform/methanol=9/1), and the obtained pale yellow solid was recrystallized from diethyl ether to give the intended compound (700 mg, 49%) as a colorless solid.

$^1$H-NMR (400 MHz, DMSO-d$_6$) δ: 1.37-1.29 (2H, m), 1.47-1.52 (2H, m), 1.57-1.67 (4H, m), 1.75-1.83 (2H, m), 1.94-2.00 (2H, m), 2.21-2.32 (2H, m), 2.49-2.51 (1H, m), 2.72-2.81 (2H, m), 4.52-4.58 (1H, m), 7.14 (2H, d, J=8.6 Hz), 7.84 (2H, d, J=8.6 Hz), 9.85 (1H, s)

Compounds of Reference Examples 2 and 3 can be produced according to the method of Reference Example 1 but starting from tert-butyl 4-[4-(ethoxycarbonyl)phenoxy]tetrahydro-1(2H)-pyridinecarboxylate and [(1-ethoxycyclopropyl)oxy](trimethyl)silane or cyclobutanone.

Reference Example 2

4-[(1-Cyclopropyl-4-piperidinyl)oxy]benzaldehyde $^1$H-NMR (400 MHz, DMSO-d$_6$) δ: 0.28-0.31 (2H, m), 0.41-0.43 (2H, m), 1.56-1.63 (3H, m), 1.91-1.95 (2H, m), 2.41-2.48 (2H, m), 2.78-2.84 (2H, m), 4.54-4.60 (1H, m), 7.14 (2H, d, J=8.6 Hz), 7.84 (2H, d, J=8.6 Hz), 9.85 (1H, s)

Reference Example 3

4-[(1-Cyclobutyl-4-4-piperidinyl)oxy]benzaldehyde $^1$H-NMR (400 MHz, DMSO-d$_6$) δ: 1.65-1.58 (4H, m), 1.77 (2H, q, J=9.5 Hz), 1.93-1.98 (4H, m), 2.03-2.09 (2H, m), 2.57 (2H, br s), 2.70 (1H, q, J=7.6 Hz), 4.52-4.57 (1H, m), 7.13 (2H, d, J=8.6 Hz), 7.84 (2H, d, J=8.6 Hz), 9.85 (1H, s)

Reference Example 4

6-[(1-Cyclobutylpiperidin-4-yl)oxy]nicotinaldehyde (1) Production of tert-butyl 4-[(5-bromopyridin-2-yl)oxy]piperidine-1-carboxylate Tert-butyl 4-hydroxytetrahydro-1(2H)-pyridinecarboxylate (10.0 g, 50.0 mmol) was dissolved in DMF (150 mL), and with stirring at 0° C., sodium hydride (purity 60%, 1.43 g) was added thereto. After stirred for 10 minutes, 4-bromo-2-fluoropyridine (8.75 g, 50.0 mmol) was added thereto and further stirred at room temperature for 20 hours. Water was added to the reaction solution and stirred for 10 minutes, and then the reaction solution was diluted with ethyl acetate, washed with water and saturated saline water in that order, and the organic layer was dried with magnesium sulfate. The solvent was evaporated off, and the residue was recrystallized from ethanol-water to obtain the intended compound (11 g) as a colorless solid.

(2) Production of 5-bromo-2-[(1-cyclobutylpiperidin-4-yl)oxy]pyridine

5-Bromo-2-[(1-cyclobutylpiperidin-4-yl)oxy]pyridine was obtained according to the method of Reference Example 1-(2) but using tert-butyl 4-[(5-bromopyridin-2-yl)oxy]piperidine-1-carboxylate, and cyclobutanone.

(3) 5-Bromo-2-[(1-cyclobutylpiperidin-4-yl)oxy]pyridine (3.80 g, 12.2 mmol), potassium vinyltrifluoroborate (2.45 g, 18.3 mmol), (1,1'-bis(diphenylphosphino)ferrocene)dichloropalladium (498 mg, 0.605 mmol), and triethylamine (1.69 mL, 12.2 mmol) were stirred in n-butanol (30 mL) at 100° C. for 24 hours. After cooled, the solvent and others were evaporated off under reduced pressure, and the residue was purified through silica gel column chromatography (hexane/ethyl acetate=9/1 to 1/1 to 0/1) to obtain the intended compound (2.59 g, 82%) as a brown solid.

(4) Production of 6-[(1-cyclobutylpiperidin-4-yl)oxy]nicotinaldehyde

2-[(1-cyclobutylpiperidin-4-yl)oxy]-5-vinylpyridine (2.59 g, 10 mmol) and sodium periodate (10.7 g, 50 mmol) were stirred in a mixed solvent of THF (10 mL) and water (10 mL) at room temperature. Osmium tetroxide (0.2 M in t-BuOH, 1 mL) was dropwise added to the reaction solution, and stirred at room temperature for 24 hours. The reaction solution was diluted with ethyl acetate, washed with aqueous 1 N sodium hydroxide solution, aqueous saturated sodium thiosulfate solution and saturated saline water in that order, and the organic layer was dried with magnesium sulfate. The solvent was evaporated off, and the residue was purified through silica gel column chromatography (chloroform/methanol=9/1) to obtain the intended compound (1.04 g, 40%) as a brown solid.

$^1$H-NMR (400 MHz, CDCl$_3$) δ: 1.62-1.76 (2H, m), 1.81-1.97 (4H, m), 2.11-2.02 (4H, m), 2.15-2.25 (2H, m), 2.62-2.71 (2H, m), 2.76 (1H, quint., J=7.4 Hz), 5.19-5.25 (1H, m), 6.81 (1H, d, J=8.6 Hz), 8.05 (1H, dd, J=8.6, 2.3 Hz), 8.59 (1H, d, J=2.3 Hz), 9.93 (1H, s)

Reference Example 5

2-[(1-Cyclobutylpiperidin-4-yl)oxy]pyrimidine-5-carbaldehyde

This was produced according to the method of Reference Example 4 but starting from 4-bromo-2-fluoropyrimidine, tert-butyl 4-hydroxytetrahydro-1(2H)-pyridinecarboxylate, cyclobutanone, and potassium vinyltrifluoroborate.

$^1$H-NMR (400 MHz, CDCl$_3$) δ: 1.65-1.81 (2H, m), 1.87-2.14 (8H, m), 2.14-2.24 (2H, m), 2.69-2.79 (2H, m), 2.85 (1H, quint., J=7.8 Hz), 5.22-5.29 (1H, m), 8.99 (2H, s), 10.02 (1H, s)

Reference Example 6

4-{3-[(3S)-3-methylpiperidin-1-yl]propoxy}benzaldehyde

This was produced according to the method of Reference Example 1-(4) but starting from 4-hydroxybenzaldehyde, 3-chloro-bromopropane and (3S)-3-methylpiperidine.

$^1$H-NMR (400 MHz, CDCl$_3$) δ: 0.81-0.93 (1H, m), 0.87 (3H, d, J=6.3 Hz), 1.57-1.75 (5H, m), 1.84-1.93 (1H, m), 2.00-2.07 (2H, m), 2.51 (2H, t, J=6.8 Hz), 2.88 (2H, t, J=12.7 Hz), 4.10 (2H, t, J=6.3 Hz), 7.00 (2H, d, J=8.8 Hz), 7.82 (2H, d, J=8.8 Hz), 9.88 (1H, s)

Reference Example 7

3-Amino-4-methoxypyridine-2-carboxylic acid (1) Production of 4-methoxy-2-picoline-N-oxide The intended compound was produced according to a method described in literature (*Organic Process Research & Development* (2000), 4(6), 473-476).

(2) Production of 4-methoxy-2-methyl-3-nitropyridine-N-oxide

4-Methoxy-2-picoline-N-oxide (22.5 g, 0.162 mol), concentrated sulfuric acid (50 ml) and fuming nitric acid (15 ml) were mixed, and heated under reflux for 24 hours. After cooled to room temperature, this was poured into an ice bath. With stirring at 0° C., this was neutralized with sodium hydrogencarbonate, and the resulting yellow solid was taken out through filtration. The resulting solid was washed with ethyl acetate and heptane, and the intended compound was obtained as a mixture with a 5-nitro positional isomer thereof (isomer ratio 1/1, 10.97 g).

(3) Production of 4-methoxy-3-nitropyridine-2-carboxylic acid

4-Methoxy-2-methyl-3-nitropyridine-N-oxide (mixture with the positional isomer, 10.97 g, 48.5 mmol) was stirred in acetic anhydride (100 mL) at 80° C. for 8 hours. The reaction solution was concentrated under reduced pressure, and in methanol (100 mL), potassium carbonate (33 g, 0.243 mol) was added to the resulting residue at room temperature and stirred at that temperature for 2 hours. The solvent was evaporated off under reduced pressure, and the resulting residue was diluted with ethyl acetate, and washed with water. The resulting organic layer was dried with magnesium sulfate, and the solvent was evaporated off under reduced pressure. The resulting residue was suspended in water (100 mL), and potassium permanganate (23 g, 0.145 mol) was added thereto at room temperature. The reaction solution was stirred at 90° C. for 16 hours, then potassium permanganate (20 g, 0.126 mol) was added thereto and stirred at 90° C. for 3 hours. The reaction solution was cooled to room temperature, methanol was added thereto, and stirred at room temperature for 2 hours. The reaction liquid was filtered, concentrated, and 2 N hydrochloric acid was added to the resulting residue, and the solution was controlled to have a pH of 2. The reaction solution was stirred at 0° C. for 1 hour, then the resulting milky white solid was taken out through filtration and dried to obtain the intended compound (1.35 g, 3 steps, 14%).

$^1$H-NMR (400 MHz, DMSO-$d_6$) δ: 4.02 (3H, s), 7.65 (1H, d, J=5.9 Hz), 8.70 (1H, d, J=5.9 Hz)

(4) Production of 3-amino-4-methoxypyridine-2-carboxylic acid

4-Methoxy-3-nitropyridine-2-carboxylic acid (1.35 g, 6.81 mmol), sodium hydrogencarbonate (690 mg, 817 mmol), water (10 mL) and 10% palladium-carbon (135 mg) were stirred in a hydrogen atmosphere at room temperature for 24 hours. The reaction solution was filtered through Celite, the Celite was washed with water and methanol, and the mother liquid was concentrated. 2 N hydrochloric acid was added to the resulting residue, and the solution was controlled to have a pH of 1. The reaction solution was stirred at 0° C. for 1 hour, and the resulting pale gray solid was taken out through filtration and dried to obtain the intended compound (940 mg, 56%).

$^1$H-NMR (400 MHz, DMSO-$d_6$) δ: 4.13 (3H, s), 7.43 (1H, d, J=6.3 Hz), 8.08 (1H, d, J=6.3 Hz)

Reference Example 8

3-Amino-2-methoxyisonicotinic acid (1) Production of t-butyl (2-methoxypyridin-3-yl)carbamate 2-methoxypyridine-3-amine (7.0 g, 56.4 mmol) and di-t-butyl dicarbonate (18.5 g, 84.6 g) were dissolved in 1,3-dioxane (20 mL), and heated under reflux for 24 hours. The solvent was evaporated off to obtain the intended, pale yellow oily compound (13.1 g).

(2) Production of 3-[(t-butoxycarbonyl)amino]-2-methoxyisonicotinic acid

T-butyl (2-methoxypyridin-3-yl)carbamate (8.0 g, 35.7 mmol) and tetramethylethylenediamine (8.3 g, 71.4 mmol) were dissolved in diethyl ether (100 mL). The reaction solution was stirred at −78° C., to which n-butyllithium (2.44 M in hexane, 36.6 mL) was dropwise added at that temperature. The reaction solution was stirred at −78° C. for 1 hour, then gradually heated up to 0° C., and $CO_2$ (solid) was added to it at 0° C. This was stirred at that temperature, and then aqueous saturated ammonium chloride solution was added thereto. The aqueous layer was separated, controlled to have a pH of 1 with 1 N hydrochloric acid added thereto, and extracted with chloroform. All the organic layers were combined, and dried with magnesium sulfate. The solvent was evaporated off under reduced pressure to obtain the intended compound (6.74 g, 70.4%) as a pale yellow oily substance.

(3) Production of 3-amino-2-methoxyisonicotinic acid

3-[(T-butoxycarbonyl)amino]-2-methoxyisonicotinic acid (6.6 g, 24.6 mmol) was dissolved in trifluoroacetic acid (10 mL), and stirred at room temperature for 8 hours. The solvent was evaporated off under reduced pressure, and the resulting milky white solid was washed with water and ethanol to obtain a white solid (2.35 g, 56.8%). The mother liquid was again concentrated, and the resulting residue was washed with acetone and hexane to obtain a pale pink solid (1.3 g, 31.4%).

$^1$H-NMR (400 MHz, $CD_3OD$) δ: 4.27 (3H, s), 7.42 (1H, d, J=6.3 Hz), 7.57 (1H, d, J=6.3 Hz)

Reference Example 9

4-Amino-N,5-dimethylnicotinamide (1) Production of methyl 4-amino-5-methylnicotinate The intended compound was produced according to a method described in literature (*Chemical Communications* (Cambridge, United Kingdom) (2002), (18), 2170-2171).

(2) Production of 4-amino-N,5-dimethylnicotinamide

Methyl 4-amino-5-methylnicotinate (100 mg, 0.60 mmol) and methylamine (2.0 M in MeOH, 2 mL) were mixed, and stirred under heat at 100° C. in a sealed tube for 24 hours. The solvent was evaporated off under reduced pressure, and the resulting residue was purified through silica gel column chromatography (chloroform/methanol=9/1) to obtain the intended compound (91 mg, 91%) as a yellow solid.

$^1$H-NMR (400 MHz, $CDCl_3$) δ: 2.11 (3H, s), 2.99 (3H, d, J=4.9 Hz), 6.17-6.21 (2H, m), 6.37-6.44 (1H, m), 8.07 (1H, s), 8.38 (1H, s)

Reference Example 10

3-Amino-5-bromo-N-methylpyridine-2-carboxamide (1) Production of 2,5-dibromo-3-nitropyridine Hydrogen bromide (48% in $H_2O$, 13 mL) was stirred at 0° C., to which 5-bromo-3-nitropyridin-2-amine (5.0 g, 22.9 mmol) was dropwise added with its inner temperature kept at 5° C. or lower. After the addition, bromine (4.69 mL) and sodium sulfite (6.32 g) were added to it in that order. After stirred at 0° C. for 45 minutes, aqueous sodium hydroxide (9.16 g) solution (10 mL) was added thereto and stirred at room temperature for 1 hour. The resulting solid was taken out through filtration, washed with water and dried to obtain the intended compound (3.80 g, 58.9%).

(2) Production of 5-bromo-2-cyano-3-nitropyridine 2,5-Dibromo-3-nitropyridine (3.80 g, 13.4 mmol) and copper cyanide (2.42 g, 26.8 mmol) were mixed, and stirred under heat at 150° C. for 2 hours. After cooled to room temperature, the contents were filtered, and the residue was washed with acetone. The mother liquid was concentrated, and the resulting residue was purified through silica gel column chromatography (hexane/ethyl acetate=9/1 to 3/1) to obtain the intended compound (1.80 g, 59%) as a yellow solid.

(3) Production of 5-bromo-3-nitropyridine-2-carboxamide

5-Bromo-2-cyano-3-nitropyridine (500 mg, 2.19 mmol) was dissolved in concentrated sulfuric acid (1 mL), and stirred at 100° C. for 2 hours. After cooled to 0° C., water was added thereto, and stirred at that temperature. The resulting pale gray solid was taken out through filtration and dried to obtain the intended compound (447 mg, 83%).

(4) Production of 3-amino-5-bromopyridine-2-carboxamide

5-Bromo-3-nitropyridine-2-carboxamide (400 mg, 1.63 mmol), ammonium chloride (435 mg, 8.15 mmol) and iron powder (273 mg, 4.89 mmol) were suspended in methanol (6 mL) and water (3 mL), and stirred at 100° C. for 20 hours. After cooled to room temperature, this was filtered through Celite, and the Celite was washed with methanol. The mother liquid was concentrated, and the residue was dissolved in chloroform and washed with water. The organic layer was concentrated under reduced pressure to obtain the intended compound (246 mg, 70%).

(5) Production of 3-amino-5-bromopyridine-2-carboxylic acid

3-Amino-5-bromopyridine-2-carboxamide (216 mg, 1.0 mmol) was dissolved in concentrated hydrochloric acid (3 μL), and stirred at 100° C. for 20 hours. After cooled to 0° C., water (10 mL) was added to it and controlled to have a pH of 7 with sodium hydrogencarbonate solution added thereto. The resulting gray solid was taken out through filtration and dried to obtain the intended compound (119 mg, 55%).

(6) Production of 3-amino-5-bromo-N-methylpyridine-2-carboxamide

3-Amino-5-bromopyridine-2-carboxylic acid (500 mg, 2.30 mmol) and N',N-carbonyldiimidazole (410 mg, 2.53 mmol) were stirred in DMF (5 mL) at 40° C. for 2 hours. After cooled to room temperature, methylamine (2.0 M in THF, 2.3 mL) was added thereto and further stirred at room temperature for 1 hour. The solvent was evaporated off under reduced pressure, and the residue was purified through silica gel column chromatography (chloroform/methanol=9/1 to 4/1) to obtain the intended compound (4.99 g, 94%) as a milky white solid.

$^1$H-NMR (400 MHz, CDCl$_3$) δ: 2.96 (3H, d, J=4.9 Hz), 5.81-6.28 (2H, m), 7.17 (1H, d, J=2.0 Hz), 7.85 (1H, d, J=2.0 Hz), 7.88-7.95 (1H, m)

Pharmaceutical test examples with the compounds of Examples 16 and 89 are described below.

Pharmaceutical Test Example 1

Histamine Analogue-Binding Inhibition Test

A cDNA sequence coding for a human histamine-3 receptor [see WO00/39164] was cloned with expression vectors pCR2.1, pEF1x (by Invitrogen) and pCI-neo (by Promega). The resulting expression vector was transfected into host cells, HEK293 and CHO-K1 (American Type Culture Collection), according to a cationic lipid process [see Proceedings of the National Academy of Sciences of the United States of America, Vol., 84, p. 7413 (1987)] to obtain histamine-3 receptor expression cells.

A membrane specimen prepared from the cells having expressed a histamine-3 receptor was incubated in an assay buffer (50 mM Tris buffer, pH 7.4) along with a test compound and 20,000 cpm [$^3$H]N-α-methylhistamine (by NEN) therein, at 25° C. for 2 hours, and then filtered through a glass filter GF/C. After washed with 50 mM Tris buffer (pH 7.4), the radioactivity on the glass filter was determined. The non-specific binding was determined in the presence of 10 μM thioperamide (by Sigma), and the 50% inhibitory concentration (IC$_{50}$) of the test compound to the specific N-α-methylhistamine binding was calculated [see Molecular Pharmacology, Vol. 55, p. 1101 (1999)].

As a result, IC$_{50}$ of the compound of Example 16 was 0.68 nM; and IC$_{50}$ of the compound of Example 89 was 0.33 mM.

As in the above, the compound of Example 16 strongly inhibited the binding of N-alpha-methylhistamine (histamine analogue) to histamine-H3 receptor.

Pharmaceutical Test Example 2

Brain/Cerebrospinal Fluid Migration Test

A test compound was orally or intravenously administered to SD male rats (7 to 10 week-age, 200 to 400 g). While they were anesthetized with ether for a predetermined period of time, the whole blood was collected from them via their abdominal aorta, using a heparin-processed syringe. Then, their occipital skin was cut open, and a dental 30 G needle was stuck into the cervical vertebrae and further into the subarachnoid cavity. Via the tube connected to the dental 30 G needle, from 50 to 100 μL of the cerebrospinal fluid was collected in a 1 mL-syringe, and then the brain was taken out. The blood sample was centrifuged (4° C., 6000 rpm, 10 min), and the resulting plasma was stirred with ethanol of three times (including an internal standard substance) added thereto. The brain sample was homogenized with 2 mL of water added thereto, and a part of it was taken out and stirred with ethanol of three times (including an internal standard substance) added thereto. The cerebrospinal fluid was homogenized with 3 times its volume of ethanol (including an internal standard substance) added thereto. The above samples were left at −20° C. for 20 minutes, then centrifuged (4° C., 12,000 g, 10 min), and the supernatant was analyzed through LC/MS/MS. According to a relative calibration curve method, the concentration of the test compound in the plasma, in the brain and in the cerebrospinal fluid was determined.

As a result, in 30 minutes after its intravenous administration (3 mg/kg), the concentration of the compound of Example 16 was 2.22 nmol/g in the brain, 0.134 μM in the cerebrospinal fluid and 1.36 μM in the plasma.

In 2 hours after its oral administration (10 mg/kg), the concentration of the compound of Example 89 was 1.45 nmol/g in the brain, 0.027 μM in the cerebrospinal fluid and 0.70 μM in the plasma.

INDUSTRIAL APPLICABILITY

The invention provides novel substances having a histamine-H3 receptor antagonistic activity (activity to prevent histamine from binding to histamine-H3 receptor) or a histamine-H3 receptor inverse-agonistic activity (activity to inhibit the homeostatic activity of histamine-H3 receptor); or that is, novel substances acting as a histamine-H3 receptor agonist or antagonist in living bodies.

Quinazoline derivatives of formula (I) or their pharmaceutically-acceptable salts that the invention provides have a strong histamine-H3 receptor antagonistic or inverse-agonistic activity, and are useful for prevention or remedy of metabolic system diseases such as obesity, diabetes, hormone secretion disorder, hyperlipemia, gout, fatty liver; circulatory system diseases such as stenocardia, acute/congestive cardiac insufficiency, cardiac infarction, coronary arteriosclerosis, hypertension, nephropathy, electrolyte abnormality; or central or peripheral nervous system diseases such as sleep disorder, various diseases accompanied by sleep disorder (e.g., idiopathic hypersomnia, repetitive hypersomnnia, true hypersomnia, narcolepsy, sleep periodic acromotion disorder, sleep apnea syndrome, circadian rhythm disorder, chronic fatigue syndrome, REM sleep disorder, senile insomnia, night workers' sleep insanitation, idiopathic insomnia, repetitive insomnia, true insomnia, depression, anxiety, schizophrenia), bulimia, emotional disorder, epilepsy, delirium, dementia, attention deficit/hyperactivity disorder, memory disorder, Alzheimer's disease, Parkinson's disease, cognition disorder, motion disorder, paresthesia, dysosmia, morphine resistance, drug dependency, alcoholism, tremor.

The invention claimed is:

1. A compound of the formula (I):

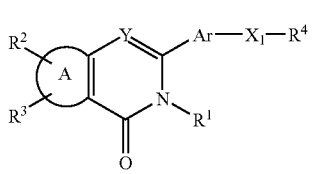

wherein:

$R^1$ is selected from the group consisting of:

an aryl group; a 5- or 6-membered heteroaryl group having, in the ring, from 1 to 4 hetero atoms selected from a group consisting of a nitrogen atom, a sulfur atom and an oxygen atom; a heteroarylalkyl group; a linear or branched lower alkyl group; an aralkyl group; an alkoxy group; an alkoxycarbonyl group; and an alkanoyl group; wherein the aryl group, the heteroaryl group, the heteroarylalkyl group or the aralkyl group may be substituted with a lower alkyl group, a halogen atom or an alkoxy group; and the lower alkyl group may be substituted with a hydroxyl group, a halogen atom or an alkoxy group;

$R^2$ and $R^3$ are the same or different, and each is selected from the group consisting of:

a hydrogen atom; an amino group; an alkylamino group; a dialkylamino group; a nitro group; a cyano group; a hydroxyl group; a lower alkylsulfonyl group; a halogen atom; a lower alkyl group wherein the lower alkyl group may be substituted with a halogen atom; a cycloalkyl group wherein the cycloalkyl group may be substituted with a halogen atom; an alkoxy group wherein the alkoxy group may be substituted with a halogen atom or a hydroxyl group; a cycloalkoxy group wherein the cycloalkoxy group may be substituted with a halogen atom; an aryloxy group; an aralkyloxy group; a heteroaryloxy group; a heteroarylalkyloxy group; an aryl group; a heteroaryl group; an arylcarbamoyl group; a heteroarylcarbamoyl group; an arylalkylcarbamoyl group; a heteroarylalkylcarbamoyl group; a mono- or di-lower alkylcarbamoyl group; an aryloxycarbonylamino group; an arylalkyloxycarbonylamino group; a lower alkyloxycarbonylamino group; an alkylcarbonylamino group; an arylcarbonylamino group; a heteroarylcarbonylamino group; an arylalkylcarbonylamino group; a heteroarylalkylcarbonylamino group; an alkanoyl group; an arylcarbonyl group; an arylalkylcarbonyl group; a formyl group; a hydroxyl group; an alkylthio group; an alkoxycarbonylamino group; a lower alkylsulfonylamino group; an arylsulfonylamino group; an alkylaminosulfonyl group; and an arylaminosulfonyl group;

$R^4$ is a group of the formula (II):

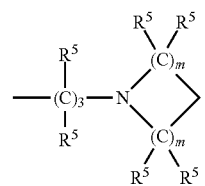

wherein $R^5$ each independently represents a hydrogen atom, a lower alkyl group, a hydroxyl group or a halogen atom; m each independently is an integer from 0 to 4, provided that both m's are not 0 at the same time, or a group of the formula (III):

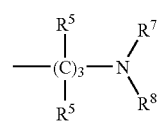

wherein $R^5$ has the same meaning as above; $R^7$ and $R^8$ each independently represent a lower alkyl group, an arylalkyl group, or a heteroarylalkyl group, provided that both $R^7$ and $R^8$ are not a lower alkyl group at the same time, or a group of the formula (IV):

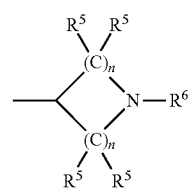

wherein $R^5$ has the same meaning as above; $R^6$ represents a linear or branched lower alkyl group, or a cycloalkyl group, wherein 1 or 2 methylene groups in the cycloalkyl group may be substituted with O, S or N; n each independently is an integer from 0 to 4, provided that both n's are not 0 at the same time, or a group of the formula (V):

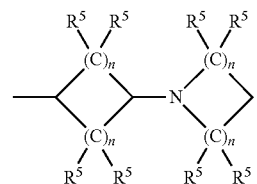

wherein $R^5$ and n have the same meanings as above;

$X_1$ represents NH, O or S;

Y represents N;

Ar represents an aryl group or a heteroaryl group wherein the aryl group or the heteroaryl group may have 1 or 2 substituents of a lower alkyl group, an alkoxy group or a halogen atom on Ar;

the ring A represents a 5- or 6-membered heteroaryl group having 1 or 2 nitrogen atoms or oxygen atoms in the ring, or represents a phenyl group;
or a pharmaceutically acceptable salt thereof.

2. The compound of claim 1 wherein $X_1$ is O and Y is N.

3. The compound of claim 1 wherein $X_1$ is O; Y is N; and Ar is a divalent group derived from benzene or pyridine by removing two hydrogen atoms therefrom, which may be mono- or di-substituted with a lower alkyl group, a lower alkoxy group or a halogen atom.

4. The compound of claim 1 wherein $X_1$ is O; Y is N; Ar is a divalent group derived from benzene or pyridine by removing two hydrogen atoms therefrom, which may be mono- or di-substituted with a lower alkyl group, a lower alkoxy group or a halogen atom; and the ring A is a benzene ring or a pyridine ring.

5. The compound of claim 4 wherein the ring A is a benzene ring.

6. The compound of claim 4 wherein the ring A is a pyridine ring.

7. The compound of claim 4 wherein $R^4$ is a group of the formula (II):

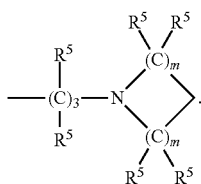

8. The compound of claim 7 wherein each m is 1 or 2.

9. The compound of claim 4 wherein $R^4$ is a group of the formula (IV):

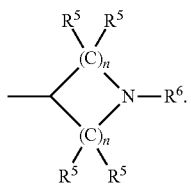

10. The compound of claim 9 wherein each n is 2.

11. The compound of claim 1 wherein $R^1$ is a lower alkyl group.

12. The compound of claim 1 wherein $R^1$ is a methyl group.

13. The compound of claim 1 wherein at least one of $R^2$ and $R^3$ is a hydrogen atom.

14. The compound of claim 1 wherein at least one of $R^2$ and $R^3$ is a hydrogen atom, and the other is a hydrogen atom; a halogen atom; a lower alkyl group wherein the lower alkyl group may be substituted with from 1 to 3, the same or different halogen atoms; a lower alkoxy group wherein the lower alkoxy group may be substituted with from 1 to 3, the same or different halogen atoms; a nitro group; a lower alkylcarbonylamino group wherein the lower alkyl group in the lower alkylcarbonylamino group may be substituted with from 1 to 3, the same or different halogen atoms; or a lower alkylsulfonylamino group.

15. The compound of claim 1 wherein at least one of $R^2$ and $R^3$ is a hydrogen atom, and the other is a hydrogen atom, a lower alkoxy group wherein the lower alkoxy group may be substituted with from 1 to 3, the same or different halogen atoms, or a lower alkyl group wherein the lower alkyl group may be substituted with from 1 to 3, the same or different halogen atoms.

16. A compound which is selected from the group consisting of:
3,8-dimethyl-2-[4-(3-piperidin-1-ylpropoxy)phenyl]-4(3H)-quinazolinone;
3-methyl-2-[4-(3-piperidin-1-ylpropoxy)phenyl]-4(3H)-quinazolinone;
3-ethyl-2-[4-(3-piperidin-1-ylpropoxy)phenyl]-4(3H)-quinazolinone;
3,6-dimethyl-2-[4-(3-piperidin-1-ylpropoxy)phenyl]-4(3H)-quinazolinone;
3,5-dimethyl-2-[4-(3-piperidin-1-ylpropoxy)phenyl]-4(3H)-quinazolinone;
3-propyl-2-[4-(3-piperidin-1-ylpropoxy)phenyl]-4(3H)-quinazolinone;
3-benzyl-2-[4-(3-piperidin-1-ylpropoxy)phenyl]-4(3H)-quinazolinone;
3-ethyl-2-[3-(3-piperidin-1-ylpropoxy)phenyl]-4(3H)-quinazolinone;
3-isopropyl-2-[4-(3-piperidin-1-ylpropoxy)phenyl]-4(3H)-quinazolinone;
2-[4-(3-piperidin-1-ylpropoxy)phenyl]-3-phenyl-4(3H)-quinazolinone;
2-[4-(3-piperidin-1-ylpropoxy)phenyl]-3-(2,2,2-trifluoroethyl)-4(3H)-quinazolinone;
3,8-dimethyl-2-[4-(3-pyrrolidin-1-ylpropoxy)phenyl]-4(3H)-quinazolinone;
2-(2-methoxy-4-{3-[(3S)-3-methylpiperidin-1-yl]propoxy}phenyl)-3-methylquinazolin-4(3H)-one;
8-methoxy-2-(2-methoxy-4-{3-[(3S)-3methylpiperidin-1-yl]propoxy}phenyl)-3-methylquinazolin-4(3H)-one;
3-methyl-2-[4-(3-piperidin-1-ylpropoxy)phenyl]pyrido[2,3-d]-pyrimidin-4(3H)-one;
3-methyl-2-[4-(3-pyrrolidin-1-ylpropoxy)phenyl]-4(3H)-quinazolinone;
3-methyl-2-[4-(1-cyclopentyl-4-piperidinyloxy)phenyl]-4(3H)-quinazolinone;
6-chloro-3-methyl-2-[4-(3-piperidin-1-ylpropoxy)phenyl]pyrido[3,4-d]-pyrimidin-4(3H)-one;
3,7-dimethyl-2-[4-(3-piperidin-1-ylpropoxy)phenyl]-4(3H)-quinazolinone;
3-methyl-2-[4-(3-pyrrolidin-1-ylpropoxy)phenyl]pyrido[2,3-d]-pyrimidin-4(3H)-one;
2-[4-(1-cyclopentyl-4-piperidinyloxy)phenyl]-3-methylpyrido[2,3-d]-pyrimidin-4(3H)-one;
2-[4-(1-cyclobutyl-4-piperidinyloxy)phenyl]-3-methylpyrido[2,3-d]-pyrimidin-4(3H)-one;
2-[4-(1-cyclobutyl-4-piperidinyloxy)phenyl]-3-(2-methoxyethyl)pyrido[2,3-d]pyrimidin-4(3H)-one;
2-{4-[(1-cyclobutylpiperidin-4-yl)oxy]phenyl}-8-methoxyquinazolin-4(3H)-one;
7-bromo-2-{4-[(1-cyclopentylpiperidin-4-yl)oxy]-2-methoxyphenyl}-3-methylpyrido[3,2-d]pyrimidin-4(3H)-one;
7-bromo-2-{4-[(1-cyclobutylpiperidin-4-yl)oxy]-2-methoxyphenyl}-3-methylpyrido[3,2-d]pyrimidin-4(3H)-one;
2-{6-[(1-cyclobutylpiperidin-4-yl)oxy]pyridin-3-yl}-8-methoxy-3-methylquinazolin-4(3H)-one;
6-chloro-2-{4-[(1-cyclopentylpiperidin-4-yl)oxy]phenyl}-3-methylpyrido[3,4-d]pyrimidin-4(3H)-one;
2-{4-[(1-cyclobutylpiperidin-4-yl)oxy]phenyl-8-methoxy-3-methylpyrido[3,4-d]pyrimidin-4(3H)-one;

6-chloro-2-{4-[(1-cyclobutylpiperidin-4-yl)oxy]phenyl}-3-methylpyrido[3,4-d]pyrimidin-4(3H)-one;

6-chloro-2-[2-methoxy-4-(3-pyrrolidin-1-ylpropoxy)phenyl]-3-methylpyrido[3,4-d]pyrimidin-4(3H)-one;

2-{4-[(1-cyclobutylpiperidin-4-yl)oxy]phenyl}-8-methylquinazolin-4(3H)-one;

8-methoxy-3-methyl-2-[4-(3-pyrrolidin-1-ylpropoxy)phenyl]pyrido[3,4-d]pyrimidin-4(3H)-one;

2-{4-[(1-cyclopentylpiperidin-4-yl)oxy]phenyl}-8-methoxy-3-methylpyrido[3,4-d]pyrimidin-4(3H)-one;

8-chloro-2-{4-[(1-cyclobutylpiperidin-4-yl)oxy]phenyl}-3-methylquinazolin-4(3H)-one;

2-{4-[(1-cyclobutylpiperidin-4-yl)oxy]phenyl}-3-methyl-8-(trifluoromethyl)quinazolin-4(3H)-one;

2-{6-[(1-cyclobutylpiperidin-4-yl)oxy]pyridin-3-yl}-3,8-dimethylquinazolin-4(3H)-one;

6-chloro-2-{4-[(1-cyclobutylpiperidin-4-yl)oxy]-2-methoxyphenyl}-3-methylpyrido[3,4-d]pyrimidin-4(3H)-one;

6-chloro-2-{4-[(1-cyclopentylpiperidin-4-yl)oxy]-2-methoxyphenyl}-3-methylpyrido[3,4-d]pyrimidin-4(3H)-one;

2-{4-[(1-cyclobutylpiperidin-4-yl)oxy]phenyl-8-fluoro-3-methylquinazolin-4(3H)-one;

2-{4-[(1-cyclopentylpiperidin-4-yl)oxy]phenyl-8-fluoro-3-methylquinazolin-4(3H)-one;

8-fluoro-2-(2-methoxy-4-{3-[(3S)-3-methylpiperidin-1-yl]propoxy}phenyl)-3-methylquinazolin-4-(3H)-one;

5-fluoro-3-methyl-2-[4-(3-pyrrolidin-1-ylpropoxy)phenyl]quinazolin-4(3H)-one;

2-{4-[(1-cyclobutylpiperidin-4-yl)oxy]phenyl}-5-fluoro-3-methylquinazolin-4(3H)-one;

2-{4-[(1-cyclobutylpiperidin-4-yl)oxy]phenyl}-3,8-dimethylpyrido[4,3-d]pyrimidin-4(3H)-one;

2-{2-[(1-cyclobutylpiperidin-4-yl)oxy]pyrimidin-5-yl}-8-methoxy-3-methylquinazolin-4(3H)-one;

2-{2-[(1-cyclobutylpiperidin-4-yl)oxy]pyrimidin-5-yl}-8-methoxy-3-methylpyrido[3,4-d]pyrimidin-4(3H)-one;

2-{6-[(1-cyclobutylpiperidin-4-yl)oxy]pyridin-3-yl}-8-methoxy-3-methylpyrido[3,4-d]pyrimidin-4(3H)-one;

2-{4-[(1-cyclobutylpiperidin-4-yl)oxy]phenyl}-6-methoxy-3-methylpyrido[3,4-d]pyrimidin-4(3H)-one;

2-{4-[(1-cyclopentylpiperidin-4-yl)oxy]phenyl}-6-methoxy-3-methylpyrido[3,4-d]pyrimidin-4(3H)-one;

3-methyl-2-(4-{3-[(3S)-3-methylpiperidin-1-yl]propoxy}phenyl)pyrido[3,2-d]pyrimidin-4(3H)-one;

2-{4-[(1-cyclobutylpiperidin-4-yl)oxy]phenyl}-3-methylpyrido[3,2-d]pyrimidin-4(3H)-one;

2-{4-[(1-cyclopentylpiperidin-4-yl)oxy]phenyl}-3-methylpyrido[3,2-d]pyrimidin-4(3H)-one;

3,8-dimethyl-2-(4-{3-[(3S)-3-methylpiperidin-1-yl]propoxy}phenyl)pyrido[4,3-d]pyrimidin-4(3H)-one;

7-bromo-3-methyl-2-(4-{3-[(3S)-3methylpiperidin-1-yl]propoxy}phenyl)pyrido[3,2-d]pyrimidin-4(3H)-one;

7-methoxy-3-methyl-2-[4-(3-pyrrolidin-1-ylpropoxy)phenyl]quinazolin-4(3H)-one;

7-methoxy-3-methyl-2-[4-(3-[(3S)-3-methylpiperidin-1-yl]propoxy)phenyl]quinazolin-4(3H)-one;

2-{4-[(1-cyclobutylpiperidin-4-yl)oxy]phenyl}-7-methoxy-3-methylquinazolin-4(3H)-one;

2-{4-[(1-cyclobutylpiperidin-4-yl)oxy]phenyl}-8-methoxy-3-methylpyrido[3,2-d]pyrimidin-4(3H)-one;

7-bromo-2-[2-(2-fluoroethoxy)-4-(3-piperidin-1-ylpropoxy)phenyl]-3-methylquinazolin-4(3H)-one;

6-chloro-2-[2-(2-fluoroethoxy)-4-(3-pyrrolidin-1-ylpropoxy)phenyl]-3-methylpyrido[3,4-d]pyrimidin-4(3H)-one;

2-{4-[(1-cyclobutylpiperidin-4-yl)oxy]phenyl}-4-(2-fluoroethoxy)-8-methoxyquinazoline;

2-{4-[(1-cyclobutylpiperidin-4-yl)oxy]phenyl}-3-methylpyrido[3,4-d]pyrimidin-4(3H)-one;

2-{4-[(1-cyclopentylpiperidin-4-yl)oxy]phenyl}-3-methylpyrido[3,4-d]pyrimidin-4(3H)-one;

2-{4-[(1-cyclobutylpiperidin-4-yl)oxy]phenyl}-7-(2-fluoroethyl)-3-methyl-3,7-dihydropyrido[3,4-d]pyrimidine-4,8-dione;

2-{4-[(1-cyclopentylpiperidin-4-yl)oxy]phenyl}-7-(2-fluoroethyl)-3-methyl-3,7-dihydropyrido[3,4-d]pyrimidine-4,8-dione;

2-{4-[(1-cyclobutylpiperidin-4-yl)oxy]phenyl}-8-(difluoromethoxy)-3-methylpyrido[3,4-d]pyrimidin-4(3H)-one;

2-{4-[(1-cyclobutylpiperidin-4-yl)oxy]phenyl}-7-(difluoromethyl)-3-methyl-3,7-dihydropyrido[3,4-d]pyrimidine-4,8-dione;

3-methyl-2-[4-(3-piperidin-1-ylpropoxy)-phenyl]pyrido[3,4-d]pyrimidin-4(3H)-one;

3-methyl-2-[3-(3-piperidin-1-ylpropoxy)-phenyl]-6-methylsulfonylamino-4(3H)-quinazolinone;

3-methyl-2-[3-(3-piperidin-1-ylpropoxy)-phenyl]-7-methylsulfonylamino-4(3H)-quinazolinone;

3-methyl-7-nitro-2-[3-(3-piperidin-1-ylpropoxy)phenyl]-4(3H)-quinazolinone;

3-methyl-7-methylsulfonylamino-2-[4-(3-pyrrolidin-1-ylpropoxy)phenyl]-4(3H)-quinazolinone;

3-methyl-6-methylsulfonylamino-2-[4-(3-pyrrolidin-1-ylpropoxy)phenyl]-4(3H)-quinazolinone;

6-acetylamino-3-methyl-2-[4-(3-piperidin-1-ylpropoxy)phenyl]-4(3H)-quinazolinone;

3-methyl-2-[4-(3-piperidin-1-ylpropoxy)phenyl]-6-trifluoromethylcarbonylamino-4(3H)-quinazolinone;

3-methyl-2-[2-methyl-4-(3-pyrrolidin-1-ylpropoxy)phenyl]-4(3H)-quinazolinone;

3-methyl-2-[2-fluoro-4-(3-pyrrolidin-1-ylpropoxy)-phenyl]-4(3H)-quinazolinone;

6-bromo-3-methyl-2-[3-methoxy-4-(3-pyrrolidin-1-ylpropoxy)-phenyl]-4(3H)-quinazolinone;

6-bromo-3-methyl-2-[2-methoxy-4-(3-pyrrolidin-1-ylpropoxy)-phenyl]-4(3H)-quinazolinone;

2-[2-methoxy-4-(3-pyrrolidin-1-ylpropoxy)-phenyl]-3-methylpyrido[2,3-d]pyrimidin-4(3H)-one;

8-methoxy-3-methyl-2-[4-(3-pyrrolidin-1-ylpropoxy)phenyl]quinazolin-4(3H)-one;

3-allyl-2-[4-(3-pyrrolidin-ylpropoxy)phenyl]pyrido[2,3-d]pyrimidin-4(3H)-one;

2-[2-methoxy-4-(3-piperidin-1-ylpropoxy)phenyl]-3-methylpyrido[2,3-d]pyrimidin-4(3H)-one;

3-methyl-2-[2-methyl-4-(1-cyclobutyl-4-piperidinyloxy)phenyl]-4(3H)-quinazolinone;

3-methyl-2-[2-methyl-4-(1-cyclopentyl-4-piperidinyloxy)phenyl]-4(3H)-quinazolinone;

3-methyl-2-[2-methyl-4-(1-cyclohexyl-4-piperidinyloxy)phenyl]-4(3H)-quinazolinone;

3-methyl-2-[4-(1-cyclobutyl-4-piperidinyloxy)phenyl]-4(3H)-quinazolinone;

3-methyl-2-[4-(1-cyclopropyl-4-piperidinyloxy)phenyl]-4(3H)-quinazolinone;

8-methoxy-3-methyl-2-[4-(1-cyclobutyl-4-piperidinyloxy)phenyl]-4(3H)-quinazolinone;

6-methoxy-3-methyl-2-[4-(1-cyclobutyl-4-piperidinyloxy)phenyl]-4(3H)-quinazolinone;

5-methoxy-3-methyl-2-[4-(1-cyclobutyl-4-piperidinyloxy)phenyl]-4(3H)-quinazolinone;
8-methoxy-3-methyl-2-[4-(1-cyclopropyl-4-piperidinyloxy)phenyl]-4(3H)-quinazolinone;
5-methoxy-3-methyl-2-[4-(1-cyclobutyl-4-piperidinyloxy)phenyl]-4(3H)-quinazolinone;
2-{4-[(1-cyclobutylpiperidin-4-yl)oxy]phenyl}-3,8-dimethylquinazolin-4(3H)-one;
7-bromo-2-{4[(1-cyclobutylpiperidin-4-yl)oxy]phenyl}-3-methylpyrido[3,2-d]pyrimidin-4(3H)-one;
7-bromo-2-{4-[(1-cyclopentylpiperidin-4-yl)oxy]phenyl}-3-methylpyrido[3,2-d]pyrimidin-4(3H)-one;
2-{4-[(1-cyclobutylpiperidin-4-yl)oxy]-2-methoxyphenyl}-3-methylpyrido[2,3-d]pyrimidin-4(3H)-one;
2-{4-[(1-cyclopentylpiperidin-4-yl)oxy]-2-methoxyphenyl}-3-methylpyrido[2,3-d]pyrimidin-4(3H)-one;
2-{4-[(1-cyclopropylpiperidin-4-yl)oxy]phenyl}-3-ethyl-8-methylquinazolin-4(3H)-one;
2-{4-[(1-cyclobutylpiperidin-4-yl)oxy]phenyl}-3-ethyl-8-methylquinazolin-4(3H)-one;
2-{4-[(1-cyclopentylpiperidin-4-yl)oxy]phenyl}-3-ethyl-8-methylquinazolin-4(3H)-one;
2-{4-[(1-cyclobutylpiperidin-4-yl)oxy]-2-fluorophenyl}-3-methylquinazolin-4(3H)-one;
2-{4-[(1-cyclopentylpiperidin-4-yl)oxy]-2-fluorophenyl}-3-methylquinazolin-4(3H)-one; and
tert-butyl4-oxo-2-[4-(3-piperidin-1-ylpropoxy)phenyl]-[3,4H]-quinazoline-carboxylate;
or a pharmaceutically acceptable salt thereof.

17. A pharmaceutical composition which comprises an inert carrier and a compound of claim 1 or a pharmaceutically acceptable salt thereof.

* * * * *